(12) United States Patent
Ishibashi et al.

(10) Patent No.: US 7,906,532 B2
(45) Date of Patent: Mar. 15, 2011

(54) INDAZOLE DERIVATIVES

(75) Inventors: Asako Ishibashi, Chita-gun (JP); Tomoki Kato, Chita-gun (JP); Kiyoshi Kawamura, Chita-gun (JP); Sachiko Mihara, Chita-gun (JP); Mikio Morita, Chita-gun (JP)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 11/995,179

(22) PCT Filed: Jul. 14, 2006

(86) PCT No.: PCT/IB2006/002120
§ 371 (c)(1),
(2), (4) Date: Apr. 30, 2008

(87) PCT Pub. No.: WO2007/010390
PCT Pub. Date: Jan. 25, 2007

(65) Prior Publication Data
US 2008/0269211 A1   Oct. 30, 2008

Related U.S. Application Data

(60) Provisional application No. 60/701,691, filed on Jul. 22, 2005.

(51) Int. Cl.
*A61K 31/454* (2006.01)
*A61K 31/416* (2006.01)
*C07D 211/56* (2006.01)
*C07D 231/56* (2006.01)

(52) U.S. Cl. ........ 514/322; 514/406; 546/199; 548/362.5

(58) Field of Classification Search .................... None
See application file for complete search history.

(56) References Cited

U.S. PATENT DOCUMENTS

| 5,817,676 | A | | 10/1998 | Catlow et al. | ................. 514/322 |
| 6,069,152 | A | * | 5/2000 | Schaus et al. | ................. 514/322 |
| 6,096,746 | A | | 8/2000 | Suzuki et al. | ............ 514/254.06 |
| 6,117,882 | A | | 9/2000 | Schaus et al. | ................. 514/304 |

FOREIGN PATENT DOCUMENTS

| EP | 0732333 | 9/1996 |
| EP | 0829474 | 3/1998 |
| EP | 0908459 | 4/1999 |
| WO | WO 9917772 | 4/1999 |
| WO | WO 2005061483 | 7/2005 |

OTHER PUBLICATIONS

"Cure," International Dictionary of Homeopathy. Philadelphia: Elsevier Health Sciences, 2000. Credo Reference. Mar. 24, 2009 <http://www.credoreference.com/entry/4411071/.>.*
King et al., Trends in Pharmacological Sciences, vol. 29, No. 9, pp. 482-492.*
"Pain," Merck Manuals Online Medical Library: Home Edition. Accessed Mar. 24, 2009. <http://www.merck.com/mmhe/sec06/ch078/ch078a.html>.*
Stillman, Mark. "Clinical approach to patients with neuropathic pain." Cleveland Clinic Journal of Medicine, 73 (8), pp. 726-730, 733-739.*
International Search Report for PCT/IB2006/002120, 5 pages.
Written Opinion by International Searching Authority for PCT/IB2006/002120, 7 pages.

* cited by examiner

*Primary Examiner* — Rebecca L Anderson
*Assistant Examiner* — Alicia L Otton
(74) *Attorney, Agent, or Firm* — Jennifer A. Kispert; Richard V. Zanzalari

(57) ABSTRACT

This invention relates to compounds of the formula (I):

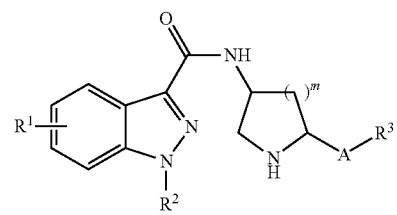

(I)

or pharmaceutically acceptable salts thereof, wherein: $R^1$, $R^2$, $R^3$, A and m are each as described herein and compositions containing such compounds and the use of such compounds in the treatment of a condition mediated by $5-HT_4$ agonistic activity such as, but not limited to, gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageral disease, nausea, central nervous system disease, Alzheimer's disease, cognitive disorder, emesis, migraine, neurological disease, pain, cardiovascular disorders, cardiac failure, heart arrhythmia, diabetes and apnea syndrome.

7 Claims, No Drawings

INDAZOLE DERIVATIVES

BACKGROUND OF THE INVENTION

This invention relates to Indazole Derivatives. These compounds have selective 5-HT$_4$ receptor agonistic activity. The present invention also relates to a pharmaceutical composition, method of treatment and use, comprising the above derivatives for the treatment of disease conditions mediated by 5-HT$_4$ receptor activity; in particular 5-HT$_4$ receptor agonistic activity.

In general, 5-HT$_4$ receptor agonists are found to be useful for the treatment of a variety of diseases such as gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageral disease, nausea, central nervous system disease, Alzheimer's disease, cognitive disorder, emesis, migraine, neurological disease, pain, cardiovascular disorders, cardiac failure, heart arrhythmia, diabetes and apnea syndrome (See TiPs, 1992, 13, 141; Ford A. P. D. W. et al., Med. Res. Rev., 1993, 13, 633; Gullikson G. W. et al., Drug Dev. Res., 1992, 26, 405; Richard M. Eglen et al, TiPS, 1995, 16, 391; Bockaert J. Et al., CNS Drugs, 1, 6; Romanelli M. N. et al., Arzheim Forsch./Drug Res., 1993, 43, 913; Kaumann A. et al., Naunyn-Schmiedeberg's. 1991, 344, 150; and Romanelli M. N. et al., Arzheim Forsch./Drug Res., 1993, 43, 913).

EP908459A1 discloses indazole compounds as 5-HT$_4$ antagonist. Especially, compounds represented by the following formula is disclosed as Example 6:

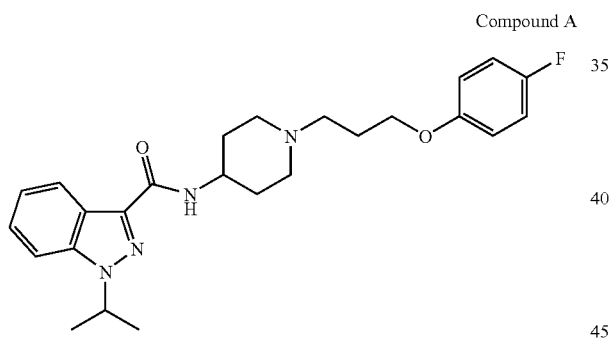

Compound A

There is a need to provide new 5-HT$_4$ agonists that are good drug candidates. In particular, preferred compounds should bind potently to the 5-HT$_4$ receptor whilst showing little affinity for other receptors and show functional activity as agonists. They should be well absorbed from the gastrointestinal tract, be metabolically stable and possess favorable pharmacokinetic properties. When targeted against receptors in the central nervous system, they should cross the blood brain barrier freely and when targeted selectively against receptors in the peripheral nervous system, they should not cross the blood brain barrier. They should be non-toxic and demonstrate few side-effects. Furthermore, the ideal drug candidate will exist in a physical form that is stable, non-hygroscopic and easily formulated.

SUMMARY OF THE INVENTION

In this invention, it has now been found out that the substitution on the carbon adjacent to the nitrogen atom of the central nitrogen-containing ring significantly improves metabolic stability.

Therefore, it has now surprisingly been found that compounds of this invention have greater metabolic stability compared with the prior art, and thus are useful for the treatment of disease conditions mediated by 5-HT$_4$ activity such as gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageral disease, nausea, central nervous system disease, Alzheimer's disease, cognitive disorder, emesis, migraine, neurological disease, pain, cardiovascular disorders, cardiac failure, heart arrhythmia, diabetes and apnea syndrome (hereinafter these diseases are referred to as '5-HT$_4$ Diseases').

The present invention provides a compound of the following formula (I):

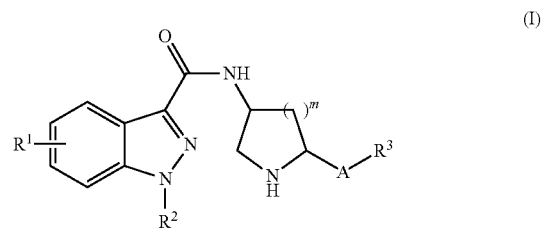

(I)

wherein
R$^1$ is a hydrogen atom, a halogen atom or a C$_1$-C$_6$ alkyl group;
R$^2$ is a C$_1$-C$_6$ alkyl group or a C$_3$-C$_6$ cycloalkyl group;
R$^3$ is a hydroxy group, a mercapt group, —C(=O)—NR$^4$R$^5$, —NR$^6$—R$^7$, a C$_1$-C$_6$ alkoxy group, a C$_3$-C$_6$ cycloalkyl group and heterocyclyl group; the said C$_1$-C$_6$ alkoxy group, the said C$_3$-C$_6$ cycloalkyl group and the said heterocyclyl group being unsubstituted or substituted with 1 to 2 substituents independently selected from the group consisting of a hydroxy group, a mercapt group, —C(=O)—NR$^4$R$^5$ and —NR$^6$—R$^7$;
R$^4$ and R$^5$ are independently a hydrogen atom, a C$_1$-C$_6$ alkyl group or a hydroxy C$_1$-C$_6$ alkyl group; or R$^4$ and R$^5$ being taken together with the nitrogen atom to which they are attached form a 3 to 6 membered heterocyclic ring;
R$^6$ is a hydrogen atom, a C$_1$-C$_6$ alkyl group or a hydroxy C$_1$-C$_6$ alkyl group;
R$^7$ is a C$_1$-C$_6$ alkyl group, a hydroxy C$_1$-C$_6$ alkyl group, a (C$_1$-C$_6$ alkyl)carbonyl group or a (C$_1$-C$_6$ alkyl)sulfonyl group
A is a C$_1$-C$_6$ alkylene group and
m is integer 1 or 2.

Also, the present invention provides the use of a compound of formula (I) or a pharmaceutically acceptable salt thereof, each as described herein, for the manufacture of a medicament for the treatment of a condition mediated by 5-HT$_4$ modulating activity; in particular, 5-HT$_4$ agonistic activity.

Preferably, the present invention also provides the use of a compound of formula (I) or a pharmaceutically acceptable salt thereof, each as described herein, for the manufacture of a medicament for the treatment of diseases selected from 5-HT$_4$ Diseases.

Also, the present invention provides a pharmaceutical composition comprising a compound of formula (I) or a pharmaceutically acceptable salt thereof, each as described herein, together with a pharmaceutically acceptable carrier for said compound.

Also, the present invention provides a pharmaceutical composition comprising a compound of formula (I) or a pharmaceutically acceptable salt thereof, each as described herein, together with a pharmaceutically acceptable carrier for said compound and another pharmacologically active agent.

Further, the present invention provides a method of treatment of a condition mediated by 5-HT$_4$ modulating activity, in a mammalian subject, which comprises administering to a mammal in need of such treatment a therapeutically effective amount of a compound of formula (I) or a pharmaceutically acceptable salt thereof, each as described herein.

Examples of conditions mediated by 5-HT$_4$ modulating activity include, but are not limited to, 5-HT$_4$ Diseases.

The compounds of the present invention may show less toxicity, good absorption, distribution, good solubility, less protein binding affinity other than acid pump, less drug-drug interaction, and good metabolic stability.

DETAILED DESCRIPTION OF THE INVENTION

In the compounds of the present invention:
Where $R^1$, $R^2$, $R^4$, $R^5$, $R^6$ and $R^7$ are the $C_1$-$C_6$ alkyl group, this represents a straight or branched chain alkyl group having one to six carbon atoms, and examples include, but are not limited to, a methyl, ethyl, propyl, isopropyl, butyl, isobutyl, sec-butyl, tert-butyl, pentyl, 4-methylbutyl, 3,3-dimethylpropyl, hexyl, 5-methylpentyl and 4,4-dimethylbutyl. Of these, methyl or ethyl is preferred for $R^1$, $R^4$, $R^5$, $R^6$ and $R^7$; $C_2$-$C_4$ alkyl group is preferred for $R^2$; methyl is more preferred for $R^1$, $R^4$, $R^5$, $R^6$ and $R^7$; isopropyl is more preferred for $R^2$.

Where $R^3$ is the $C_1$-$C_6$ alkoxy group, this represents the oxygen atom substituted with the said $C_1$-$C_6$ alkyl group, and examples include, but are not limited to, a methoxy, ethoxy, propyloxy, isopropyloxy, butyloxy, isobutyloxy, sec-butyloxy, tert-butyloxy, pentyloxy, 4-methylbutyloxy, 3,3-dimethylpropyloxy, hexyloxy, 5-methylpentyloxy and 4,4-dimethylbutyloxy. Of these, $C_1$-$C_2$ alkoxy group is preferred; methoxy is more preferred.

Where A is the $C_1$-$C_6$ alkylene group, this represents a straight or branched chain alkylene group having one to six carbon atoms, and examples include, but are not limited to, a methylene, ethylene, trimethylene, 2-methylethylene, tetramethylene, 3-methyltrimethylene, 2,2-dimethylethylene, pentamethylene, 4-methyltetramethylene, 3,3-dimethyltrimethylene, hexamethylene, 5-methylpentamethylene, 4,4-dimethyltetramethylene and 2,2-diethylethylene. Of these, methylene, ethylene or 2,2-dimethylethylene is preferred; ethylene is more preferred. Where $R^7$ is the ($C_1$-$C_6$ alkyl)carbonyl group, this represents the carbonyl group substituted with the said $C_1$-$C_6$ alkyl group, and examples include, but are not limited to, a acetyl, ethylcarbonyl, propylcarbonyl, isopropylcarbonyl, butylcarbonyl, isobutylcarbonyl, sec-butylcarbonyl, pentylcarbonyl, 4-methylbutylcarbonyl, 3,3-dimethylpropylcarbonly, hexylcarbonyl, 5-methylpentylcarbonyl and 4,4-dimethylbutylcarbony. Of these, a $C_1$-$C_2$ alkylcarbonyl is preferred; acetyl is more preferred. Where $R^7$ is the ($C_1$-$C_6$ alkyl)sulfonyl group, this represents the sulfonyl group substituted with the said $C_1$-$C_6$ alkyl group, and examples include, but are not limited to, a methylsulfonyl, ethylsulfonyl, propylsulfonyl, isopropylsulfonyl, butylsulfonyl, isobutylsulfonyl, sec-butylsulfonyl, pentylsulfonyl, 4-methylbutylsulfonyl, 3,3-dimethylpropylcarbonly, hexylcarbonyl, 5-methylpentylsulfonyl and 4,4-dimethylbutylcarbony. Of these, a $C_1$-$C_2$ alkylsulfonyl is preferred; methylsulfonyl is more preferred.

Where $R^2$ and $R^3$ are the $C_3$-$C_6$ cycloalkyl group, this represents a cycloalkyl group having three to six carbon atoms, and examples include, but are not limited to, a cyclopropyl, cyclobutyl, cyclopenthyl, and cyclohexyl. Of these, $C_3$-$C_5$ cycloalkyl is preferred for $R^2$; $C_4$-$C_6$ cycloalkyl is preferred for $R^3$; cyclobutyl is more preferred for $R^2$; cyclohexyl is more preferred for $R^3$.

Where $R^1$ is the halogen atom, this may be a fluorine, chlorine, bromine or iodine atom. Of these, a fluorine atom is preferred.

Where $R^3$ is the heterocyclyl group, this represents a 3, 4, 5, or 6-membered ring containing at least one hetero atom selected from N, O and S, and examples include, but not limited to, oxyranyl, 1-pyrrolidinyl, 2-pyrrolidinyl, 1-imidazolidinyl, 2-tetrahydrofuranyl, 1-piperidinyl, 2-piperidinyl, 1-piperazinyl, 4-tetrahydropyranyl, 4-morpholinyl, 4-thiomorpholinyl, 2-thienyl, 2-furyl, 2-thiazolyl, 2-oxazolyl, 5-tetrazolyl, 2-pyridyl, 3-pyridyl, 4-pyridyl, 2-pyrazyl and 2-pyrimidinyl. Of these, the heterocyclyl group containing at least one oxygen atom is preferred; 4-tetrahydropyranyl is more preferred.

Where $R^4$ and $R^5$ being taken together with the nitrogen atom to which they are attached form a 3 to 6 membered heterocyclic ring, this heterocyclic ring is the same as the said heterocyclyl group, with the proviso at least one nitrogen atom is included. Of these, 1-pyrrolidinyl, 1-piperidinyl and 4-morpholinyl are preferred.

Where $R^4$, $R^5$, $R^6$ and $R^7$ are the hydroxy $C_1$-$C_6$ alkyl group, this represents the said $C_1$-$C_6$ alkyl group substituted with a hydroxy group, and examples include, but are not limited to, a hydroxymethyl, 2-hydroxyethyl, 3-hydroxypropyl, 2-hydroxy-2-propyl, 4-hydroxybutyl, 5-hydroxypentyl, 4-hydroxy-4-methylbutyl, 6-hydroxyhexyl and 5-hydroxy-5-methylpentyl. Of these, hydroxymethyl or 2-hydroxyethyl is preferred; hydroxymethyl is more preferred.

The term "treating" and "treatment", as used herein, refers to curative, palliative and prophylactic treatment, including reversing, alleviating, inhibiting the progress of, or preventing the disorder or condition to which such term applies, or one or more symptoms of such disorder or condition.

Preferred compounds of the present invention are those compounds of formula (I) or a pharmaceutically acceptable salt thereof, each as described herein, in which:
(A) $R^1$ is a hydrogen atom or a halogen atom; $R^2$ is a $C_2$-$C_4$ alkyl group; $R^3$ is a hydroxy group, a $C_3$-$C_6$ cycloalkyl group and heterocyclyl group; the said $C_3$-$C_6$ cycloalkyl group and the said heterocyclyl group being unsubstituted or substituted with 1 to 2 substituents independently selected from the group consisting of a hydroxy group and a mercapt group; A is a $C_1$-$C_6$ alkylene group and m is integer 1 or 2;
(B) $R^1$ is a hydrogen atom or a fluorine atom; $R^2$ is an ethyl group or an isopropyl group; $R^3$ is a hydroxy group, a $C_3$-$C_6$ cycloalkyl group and heterocyclyl group; the said $C_3$-$C_6$ cycloalkyl group and the said heterocyclyl group being substituted with a hydroxy group; A is a $C_1$-$C_6$ alkylene group and m is integer 1 or 2;
(C) $R^1$ is a hydrogen atom or a fluorine atom; $R^2$ is a $C_2$-$C_4$ alkyl group; $R^3$ is a hydroxy group, a $C_3$-$C_6$ cycloalkyl group and heterocyclyl group; the said $C_3$-$C_6$ cycloalkyl group and the said heterocyclyl group being unsubstituted or substituted with 1 to 2 substituents independently selected from the group consisting of a hydroxy group and a mercapt group; A is a $C_1$-$C_6$ alkylene group and m is integer 1 or 2;

(D) $R^1$ is a hydrogen atom or a halogen atom; $R^2$ is a $C_2$-$C_4$ alkyl group; $R^3$ is a hydroxy group, a $C_3$-$C_6$ cycloalkyl group and heterocyclyl group; the said $C_3$-$C_6$ cycloalkyl group and the said heterocyclyl group being unsubstituted or substituted with 1 to 2 substituents independently selected from the group consisting of a hydroxy group and a mercapt group; A is a $C_1$-$C_6$ alkylene group and m is integer 2;

(E) $R^1$ is a hydrogen atom or a fluorine atom; $R^2$ is an ethyl group or an isopropyl group; $R^3$ is a hydroxy group, a $C_3$-$C_6$ cycloalkyl group and heterocyclyl group; the said $C_3$-$C_6$ cycloalkyl group and the said heterocyclyl group being substituted with a hydroxy group; A is a $C_1$-$C_6$ alkylene group and m is integer 2;

(F) $R^1$ is a hydrogen atom or a halogen atom; $R^2$ is a $C_2$-$C_4$ alkyl group; $R^3$ is a hydroxy group, a $C_3$-$C_6$ cycloalkyl group and heterocyclyl group; the said $C_3$-$C_6$ cycloalkyl group and the said heterocyclyl group being unsubstituted or substituted with 1 to 2 substituents independently selected from the group consisting of a hydroxy group and a mercapt group; A is a $C_1$-$C_6$ alkylene group and m is integer 1;

(G) $R^1$ is a hydrogen atom or a fluorine atom; $R^2$ is an ethyl group or an isopropyl group; $R^3$ is a hydroxy group, a $C_3$-$C_6$ cycloalkyl group and heterocyclyl group; the said $C_3$-$C_6$ cycloalkyl group and the said heterocyclyl group being substituted with a hydroxy group; A is a $C_1$-$C_6$ alkylene group and m is integer 1;

Preferred class of compounds of the present invention are those compounds of formula (I) or a pharmaceutically acceptable salt thereof, each as described herein, in which:

(a) $R^1$ is a hydrogen atom or a halogen atom;
(b) $R^1$ is a hydrogen atom or a fluorine atom;
(c) $R^2$ is a $C_2$-$C_4$ alkyl group;
(d) $R^2$ is an ethyl group or an isopropyl group;
(e) $R^3$ is a hydroxy group, a $C_3$-$C_6$ cycloalkyl group and heterocyclyl group; the said $C_3$-$C_6$ cycloalkyl group and the said heterocyclyl group being unsubstituted or substituted with 1 to 2 substituents independently selected from the group consisting of a hydroxy group and a mercapt group;
(f) $R^3$ is a hydroxy group, a $C_3$-$C_6$ cycloalkyl group and heterocyclyl group; the said $C_3$-$C_6$ cycloalkyl group and the said heterocyclyl group being substituted with a hydroxy group;
(g) A is a methylene group, an ethylene group or a 2,2-dimethylethylene group;
(h) A is an ethylene group;
(i) m is 1;
(j) m is 2.
(k) the configuration of the compound is as shown in the following formula (1')

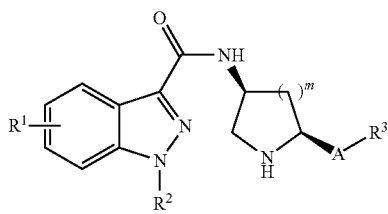

Of these classes of compounds, any combination among (a) to (k) is also preferred.

Pharmaceutically acceptable salts of a compound of formula (I) include the acid addition salts (including disalts) thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

For a review on suitable salts, see "Handbook of Pharmaceutical Salts: Properties, Selection, and Use" by Stahl and Wermuth (Wiley-VCH, Weinheim, Germany, 2002). A pharmaceutically acceptable salt of a compound of formula (I) may be readily prepared by mixing together solutions of the compound of formula (I) and the desired acid, as appropriate. The salt may precipitate from solution and be collected by filtration or may be recovered by evaporation of the solvent. The degree of ionisation in the salt may vary from completely ionised to almost non-ionised.

The compounds of the invention may exist in both unsolvated and solvated forms. The term 'solvate' is used herein to describe a molecular complex comprising a compound of the invention and one or more pharmaceutically acceptable solvent molecules, for example, ethanol. The term 'hydrate' is employed when said solvent is water.

Pharmaceutically acceptable solvates in accordance with the invention include hydrates and solvates wherein the solvent of crystallization may be isotopically substituted, e.g. $D_2O$, $d_6$-acetone, $d_6$-DMSO Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see *J Pharm Sci*, 64 (8), 1269-1288 by Haleblian (August 1975).

Hereinafter all references to a compound of formula (I) include references to salts and complexes thereof and to solvates and complexes of salts thereof.

The term "compound of the invention" or "compounds of the invention" refers to, unless indicated otherwise, a compound of formula (I) as hereinbefore defined, polymorphs, prodrugs, and isomers thereof (including optical, geometric isomers) as hereinafter defined and isotopically-labeled compounds of formula (I).

Also within the scope of the invention are so-called 'prodrugs' of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H Bundgaard (Elsevier, 1985). Some examples of prodrugs in accordance with the invention include:

(i) where the compound of formula (I) contains an alcohol functionality (—OH), an ether thereof, for example, replacement of the hydrogen with $(C_1-C_6)$alkanoyloxymethyl;

(ii) where the compound of formula (I) contains a secondary amino functionality (—$NH_2$ or —NHR where R≠H), an amide thereof, for example, replacement of one or both hydrogens with $(C_1-C_{10})$alkanoyl.

Further examples of replacement groups in accordance with the foregoing examples and examples of other prodrug types may be found in the aforementioned references.

Finally, certain compounds of formula (I) may themselves act as prodrugs of other compounds of formula (I).

Compounds of formula (I) containing one or more asymmetric carbon atoms can exist as two or more stereoisomers. It follows that a single compound may exhibit more than one type of isomerism.

Included within the scope of the present invention are all stereoisomers and geometric isomers of the compounds of formula (I), including compounds exhibiting more than one type of isomerism, and mixtures of one or more thereof. Also included are acid addition salts wherein the counterion is optically active, for example, D-lactate or racemic, for example, DL-tartrate or DL-arginine.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, New York, 1994).

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

All of the compounds of the formula (I) can be prepared by the specific methods described in the Examples section, or by routine modifications thereof. The present invention also encompasses any one or more of these processes for preparing the compounds of formula (I), in addition to any novel intermediates used therein.

General Synthesis

The compounds of the present invention may be prepared by a variety of processes well known for the preparation of compounds of this type, for example as shown in the following Methods A to D.

The following Methods A and B illustrate the preparation of compounds of formula (I). Methods C through D illustrate the preparation of various intermediates.

Unless otherwise indicated, $R^1$, $R^2$, $R^3$ and A in the following Methods are as defined above. The term "protecting group", as used hereinafter, means a hydroxy, carboxy or amino-protecting group which is selected from typical hydroxy, carboxy or amino-protecting groups described in *Protective Groups in Organic Synthesis* edited by T. W. Greene et al. (John Wiley & Sons, 1999). All starting materials in the following general syntheses may be commercially available or obtained by conventional methods known to those skilled in the art, such as *Heterocycles*, 60(5), 1203-1209 and the disclosures of which are incorporated herein by references.

Method A

This illustrates the preparation of compounds of formula (I).

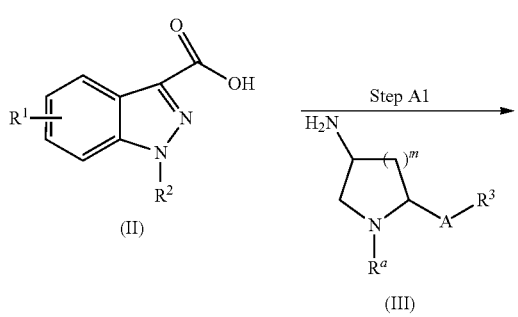

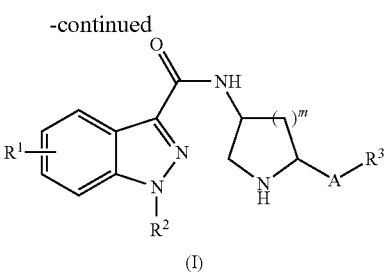

(I)

In Reaction Scheme A, $R^a$ is an amino-protecting group.

The term "amino-protecting group", as used herein, signifies a protecting group which is stable under the reaction condition and capable of being cleaved by chemical means, such as hydrogenolysis, hydrolysis, electrolysis or photolysis, and such amino-protecting groups are described in Protective Groups in Organic Synthesis edited by T. W. Greene et al. (John Wiley & Sons, 1999). Typical amino-protecting groups include, but are not limited to: benzyl, $C_2H_5O$ (C=O)—, $CH_3$(C=O)—, t-butyldimethylsilyl, t-butyldiphenylsilyl, benzyloxycarbonyl and t-buthoxycarbonyl. Of these groups, t-buthoxycarbonyl or benzyloxycarbonyl is preferred.

Step A1

In this step, the desired compound of formula (I) of the present invention is prepared by amidation of the compound of formula (II) with the compound of formula (III) (A1-a), followed by deprotection of amino-protecting group (A1-b). The compound of formula (II) is commercially available or can be prepared according to the Method C set forth below. The compound of formula (III) can be prepared according to Method D set forth below.

(A1-a) Amidation

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; aromatic hydrocarbons, such as benzene, toluene and nitrobenzene; ethers, such as diethyl ether, diisopropyl ether, tetrahydrofuran and dioxane; and amides, such as N,N-dimethylformamide and N,N-dimethylacetamide. Of these solvents, N,N-dimethylformamide is preferred.

The reaction is carried out in the presence of a condensing agent. There is likewise no particular restriction on the nature of the condensing agents used, and any condensing agent commonly used in reactions of this type may equally be used here. Examples of such condensing agents include: azodicarboxylic acid di-lower alkyl ester-triphenylphosphines, such as diethyl azodicarboxylate-triphenylphosphine; 2-halo-1-lower alkyl pyridinium halides, such as 2-chloro-1-methyl pyridinium iodide; diarylphosphorylazides, such as diphenylphosphorylazide (DPPA); chloroformates, such as ethyl chloroformate and isobutyl chloroformate; phosphoryl chlorides, such as diethyl phosphoryl chloride; phosphorocyanidates, such as diethyl cyanophosphonate (DEPC); imidazole derivatives, such as N,N'-carbonyldiimidazole (CDI); carbodiimide derivatives, such as N,N'-dicyclohexylcarbodiimide (DCC) and 1-ethyl-3-(3-dimethylaminopropyl)carbodiimide hydrochloride (EDAPC); and sulfonyl chloride derivatives, such as 2,4,6-triisopropylbenzenesulfonyl chloride. Of these, DEPC is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

(A1-b) Deprotection

This reaction is described in detail by T. W. Greene et al., Protective Groups in Organic Synthesis, 369-453, (1999), the disclosures of which are incorporated herein by reference. The following exemplifies a typical reaction involving the benzyl group deprotection.

The deprotection reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: alcohols, such as methanol, ethanol, propanol, 2-propanol and butanol; and aromatic hydrocarbons, such as benzene, toluene and nitrobenzene. Of these solvents, alcohols are preferred, and methanol is more preferred.

The deprotection reaction is carried out in the presence of a palladium catalyst and hydrogen gas. There is likewise no particular restriction on the nature of the catalysts used, and any acid commonly used in reactions of this type may equally be used here. Examples of such catalysts include, but are not limited to: acids, such as palladium-carbon, palladium hydroxide, palladium chloride, palladium (II) acetate and tris(dibenzylideneacetone)dipalladiumchloroform. Of these, palladium-carbon is preferred.

The deprotection reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Method B

This illustrates the preparation of compounds of formula (I).

Reaction Scheme B

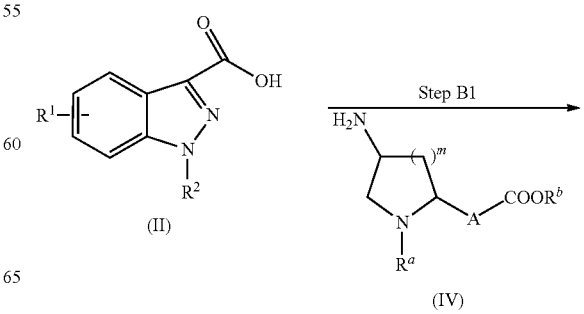

-continued

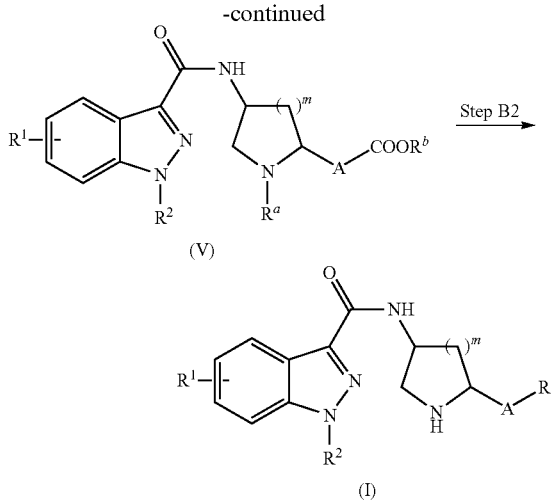

(V)

(I)

In Reaction Scheme B, $R^a$ is as defined above; $R^b$ is a $C_1$-$C_6$ alkyl group or a $C_7$-$C_{12}$ aralkyl group.

Step B1

In this step, the compound of formula (V) is prepared by the amidation of the compound of formula (II) with the compound of formula (IV). The compound of formula (II) is commercially available or can be prepared according to the Method C set forth below. The compound of formula (IV) can be prepared according to Method D set forth below. The reaction may be carried out under the same conditions as described in Step A1-a of Method A.

Step B2

In this step, the desired compound of formula (I) is prepared by the reduction to yield alcohol (B2-a), the Grignard reaction to yield alcohol (B2-b), the hydrolysis followed by amidation to yield amide (B2-c) or the amidation after the reduction and nucleophilic substitution to yield amide (B2-d) of the compound of formula (V) prepared as described in StepB1. If required, the deprotection of the amino-protecting group might follow as described in Step A1-b of Method A.

(B2-a) The Reduction

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; ethers, such as diethyl ether, diisopropyl ether, dimethoxyethane, tetrahydrofuran and dioxane; alcohols, such as methanol, ethanol, propanol, 2-propanol and butanol; acetic acid; and water. Of these solvents, ethers are preferred.

The reaction is carried out in the presence of a reducing reagent. There is likewise no particular restriction on the nature of the reducing reagents used, and any reducing reagent commonly used in reactions of this type may equally be used here. Examples of such reducing reagent include, but are not limited to: hydride compounds such as lithium aluminum hydride, sodium borohydride, lithium borohydride and diisobutyl aluminum hydride; tin reagent, such as $SnCl_2$; and borane reagents, such as boran-tetrahydrofuran complex, boran-dimethyl sulfide complex (BMS) and 9-borabicyclo[3,3,1]nonane (9-BBN). Of these, lithium borohydride is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −20° C. to about 60° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

(B2-b) The Grignard Reaction

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; ethers, such as diethyl ether, diisopropyl ether, dimethoxyethane, tetrahydrofuran and dioxane; alcohols, such as methanol, ethanol, propanol, 2-propanol and butanol; acetic acid; and water. Of these solvents, ethers are preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry but the reaction at a temperature of from about −20° C. to about 60° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

(B2-c) The Hydrolysis Followed by Amidation to Yield Amide

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: alcohols, such as methanol, ethanol, propanol, 2-propanol and butanol; water; and the mixture of water and alcohol. Of these solvents, the mixture of water and alcohol is preferred.

The reaction is carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide and potassium hydroxide; and alkali metal alkoxides, such as sodium methoxide, sodium ethoxide and potassium t-butoxide. Of these, sodium hydroxide is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −20° C. to about 60° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

After the completion of the above hydrolysis, the amidation reaction follows. The reaction may be carried out under the same conditions as described in Step A1-a.

(B2-d) The Amidation after the Reduction and Nucleophilic Substitution

This reaction is carried out with the resulting compound of Step B2-a or Step A1-a (in the case $R^3$ is a hydroxy group). The resulting alcohol is converted to the amine by the nucleophilic substitution with sodium azide or sodium cyanide followed by the reduction, and then amidated under the same conditions as described in Step A1-a The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; ethers, such as diethyl ether, diisopropyl ether, tetrahydrofuran and dioxane; amides, such as formamide, N,N-dimethylformamide, N,N-dimethylacetamide and hexamethylphosphoric triamide; and sulfoxide such as dimethyl sulfoxide and sulfolane. Of these solvents, N,N-dimethylformamide is preferred.

Before adding sodium azide, the hydroxy group is converted to a leaving group, such as a methylsulfonyl group, a trifluoromethylsulfonyl group and 4-methyl phenylsulfonyl group by adding reagents, such as trifluoromethanelsulfonyl-chloride, mesyl chloride and tosyl chloride. Of these reagents, mesyl chloride is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

After the completion of the above nucleophilic substitution, the reduction follows. The reaction may be carried out under the same conditions as described in Step B2-a.

Method C

This illustrates the preparation of compounds of formula (II).

Reaction Scheme C

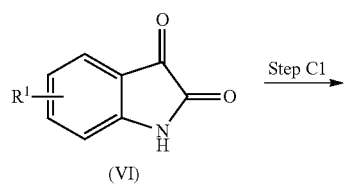

(VI)

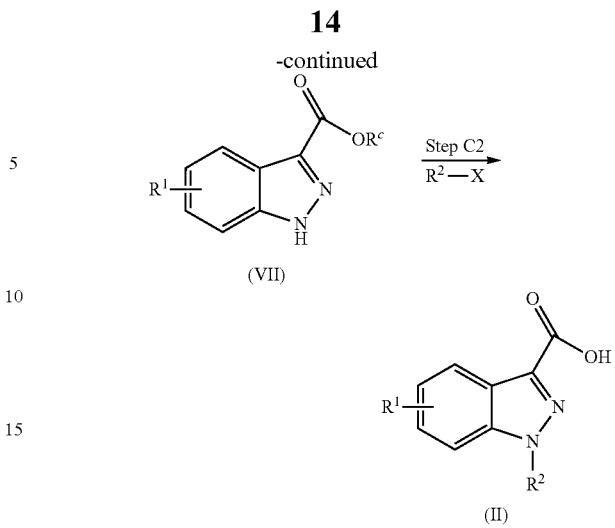

In Reaction Scheme C, $R^c$ is a $C_1$-$C_6$ alkyl group or a $C_7$-$C_{12}$ aralkyl group, preferably methyl or ethyl; X is halogen atom, preferably chlorine or bromine.

Step C1

In this step, the compound of formula (VII) is prepared by hydrolysis (C1-a) of the compound of formula (VI) followed by diazotization under the presence of sodium nitrite (C1-b), the ring closure under reductive condition (C1-c), and esterification with corresponding alcohol (C1-d) of the resulting compound.

The compound of formula (VI) is commercially available.

($C_1$-a) Hydrolysis

The reaction may be carried out under the same conditions as described in Step B2-c.

(C1-b) Diazotization

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: alcohols, such as methanol, ethanol, propanol, 2-propanol and butanol; water; and the mixture of water and alcohol. Of these solvents, water is preferred.

The reaction is carried out in the presence of an acid. There is likewise no particular restriction on the nature of the acids used, and any acid commonly used in reactions of this type may equally be used here. Examples of such acids include: acids, such as hydrochloric acid, sulfuric acid, or p-toluenesulfonic acid. Of these, sulfuric acid is preferred.

(C1-c) The Ring Closure Under Reductive Condition

The reaction may be carried out under the same conditions as described in Step B2-a.

($C_1$-d) Esterification

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; ethers, such as diethyl ether, diisopropyl ether, tetrahydrofuran and dioxane; amides, such as formamide, N,N-dimethylformamide, N,N-dimethylacetamide and hexamethylphosphoric triamide. Of these solvents, N,N-dimethylformamide is preferred.

The reaction is carried out in the presence of a condensing agent. There is likewise no particular restriction on the nature of the condensing agents used, and any condensing agent commonly used in reactions of this type may equally be used here. Examples of such condensing agents include: azodicarboxylic acid di-lower alkyl ester-triphenylphosphines, such as diethyl azodicarboxylate-triphenylphosphine; 2-halo-1-lower alkyl pyridinium halides, such as 2-chloro-1-methyl pyridinium iodide; diarylphosphorylazides, such as diphenylphosphorylazide (DPPA); chloroformates, such as ethyl chloroformate and isobutyl chloroformate; phosphoryl chlorides, such as diethyl phosphoryl chloride; phosphorocyanidates, such as diethyl phosphorocyanidate (DEPC); imidazole derivatives, such as N,N'-carbonyldiimidazole (CDI); carbodiimide derivatives, such as N,N'-dicyclohexylcarbodiimide (DCC) and 1-ethyl-3-(3-dimethylaminopropyl)carbodiimide hydrochloride (EDAPC); and sulfonyl chloride derivatives, such as 2,4,6-triisopropylbenzenesulfonyl chloride. Of these, DEPC is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

Step C2

In this step, the compound of formula (II) is prepared by alkylation of the compound of formula (VII) with the compounds of formula $R^2$—X followed by hydrolysis. The hydrolysis may be carried out under the same conditions as described in Step B2-c.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; amides, such as formamide, N,N-dimethylformamide, N,N-dimethylacetamide and hexamethylphosphoric triamide; and sulfoxides, such as dimethyl sulfoxide and sulfolane. Of these solvents, N,N-dimethylformamide is preferred.

The reaction is carried out in the presence of a base. There is likewise no particular restriction on the nature of the bases used, and any base commonly used in reactions of this type may equally be used here. Examples of such bases include: alkali metal hydrides, such as lithium hydride, sodium hydride and potassium hydride; alkali metal alkoxides, such as sodium methoxide, sodium ethoxide and potassium t-butoxide; alkali metal carbonates, such as lithium carbonate, sodium carbonate and potassium carbonate; and alkali metal amides, such as lithium amide, sodium amide, potassium amide, lithium diiropropyl amide, potassium diisopropyl amide, sodium diiropropyl amide, lithium bis(trimethylsilyl) amide and potassium bis(trimethylsilyl)amide. Of these, sodium hydride is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 50° C. to about 200° C. The time required for the reaction may also vary widely, depending on many factors, notably the reaction temperature and the nature of the starting materials and solvent employed. However, provided that the reaction is effected under the preferred conditions outlined above, a period of from about 10 minutes to about 24 hours, will usually suffice.

Method D

This illustrates the preparation of compounds of formula (III) and (IV).

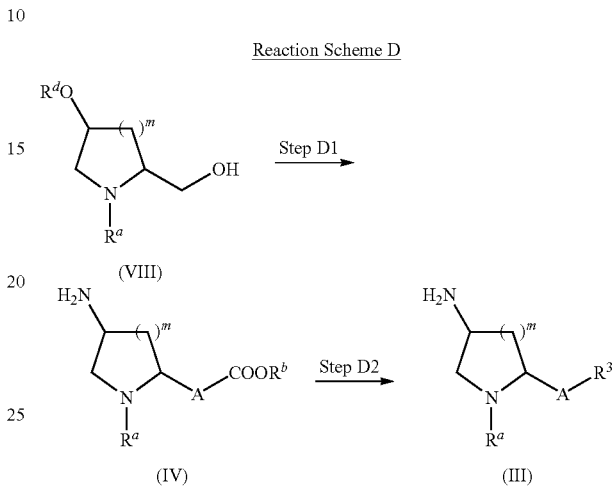

Reaction Scheme D

In Reaction Scheme D, $R^a$ and $R^b$ are each as defined above; $R^d$ is the hydroxy-protecting group.

The term "hydroxy-protecting group", as used herein, signifies a protecting group which is stable under the reaction condition and capable of being cleaved by chemical means, such as hydrogenolysis, hydrolysis, electrolysis or photolysis, and such hydroxy-protecting groups are described in *Protective Groups in Organic Synthesis* edited by T. W. Greene et al. (John Wiley & Sons, 1999). Typical carboxy-protecting groups include, but are not limited to: t-butyloxycarbonyl, methoxymethyl, benzyl, diphenylmethyl, trimethylsilyl, t-butyldimethylsilyl and allyl. Of these groups, t-butyldimethylsilyl is preferred.

Step D1

In this step, the compound of formula (IV) is prepared by conversion of the hydroxy group into formula -A-COOR$^b$ (D1-a) and deprotection of the hydroxy-protecting group followed by conversion to amino group (D1-b) of formula (VIII). The compound of formula (VIII) is commercially available or known in the literature (*Heterocycles* (2003), 60(5), 1203-1209).

(D1-γ) Conversion of the Hydroxy Group

This step comprises the nucleophilic substitution with sodium cyanide followed by hydrolysis and the esterificaton of the resulting carboxy group. The nucleophilic substitution and hydrolysis may be carried out the method under the same conditions as described in Step B2-d and Step B2-c respectively. The esterification may be carried out the method under the same conditions as described in Step C1-d.

(D1-b) Deprotection

This step comprises the deprotection of the hydroxy-protecting group followed by nucleophilic substitution with sodium azide and the reduction of the resulting azide group. The nucleophilic substitution and reduction may be carried out the method under the same conditions as described in Step B2-d.

The deprotection reaction is described in detail by T. W. Greene et al., Protective Groups in Organic Synthesis, 17-245, (1999), the disclosures of which are incorporated herein by reference. The following exemplifies a typical reaction involving the protecting group t-butyldimethylsilyl.

The deprotection reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: ethers, such as diethyl ether, diisopropyl ether, tetrahydrofuran and dioxane; and aromatic hydrocarbons, such as benzene, toluene and nitrobenzene. Of these solvents, ethers are preferred.

The deprotection reaction is carried out in the presence of an acid. There is likewise no particular restriction on the nature of the acids used, and any acid commonly used in reactions of this type may equally be used here. Examples of such acids include, but are not limited to: acids, such as hydrochloric acid, acetic acid p-toluenesulfonic acid or trifluoroacetic acid. Of these, trifluoroacetic acid is preferred.

The deprotection reaction may be carried out in the presence of a radical scavenger. There is likewise no particular restriction on the nature of the radical scavenger used, and any radical scavenger commonly used in reactions of this type may equally be used here. Examples of such radical scavengers include, but are not limited to: HBr, dimethylsulfoxide or $(CH_3CH_2)_3SiH$. Of these, $(CH_3CH_2)_3SiH$ is preferred.

The deprotection reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 10° C., more preferably from about 0° C. to about 50° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, more preferably from about 1 hour to about 24 hours, will usually suffice.

Step D2

In this step, the compound of formula (III) is prepared by conversion of ester into $R^3$ from the compound of formula (IV). The amino moiety of the compound of formula (IV) may be protected (D2-a) and deprotected (D2-b) according to the condition requirement. The conversion may be carried out under the same conditions as described in Step B2 of Method B.

(D2-a) Protection

This reaction is described in detail by T. W. Greene et al. [Protective *Groups in Organic Synthesis*, 494-653, (1999)], the disclosures of which are incorporated herein by reference. The following exemplifies a typical reaction involving the protecting group t-buthoxycarbonyl.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: water; ethers, such as diethyl ether, diisopropyl ether, tetrahydrofuran and dioxane; and sulfoxide such as dimethyl sulfoxide and sulfolane. Of these solvents, tetrahydrofuran is preferred.

The reaction is carried out in the presence of reagent. There is likewise no particular restriction on the nature of the reagents used, and any reagent commonly used in reactions of this type may equally be used here. Examples of such reagents include, but are not limited to: di-t-butyl carbonate and 1-(t-butoxycarbonyl)benztriazole. Of these, di-t-butyl carbonate is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C., more preferably from about 20° C. to about 80° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, more preferably from about 60 minutes to about 12 hours, will usually suffice.

(D2-b) Deprotection:

This method is described in detail by T. W. Greene et al., *Protective Groups in Organic Synthesis*, 494-653, (1999), the disclosures of which are incorporated herein by reference. The following exemplifies a typical method involving the benzyl protecting group in the presence of combinations of hydrogen gas and a catalyst such as palladium-carbon or platinum.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; alcohols, such as methanol, ethanol, propanol, 2-propanol and butanol; and ethers, such as diethyl ether, diisopropyl ether, tetrahydrofuran and dioxane. Of these solvents, methanol is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a pharmaceutical composition or formulation in association with one or more pharmaceutically acceptable carriers or excipients. The term "carrier" or "excipient" is used herein to describe any ingredient other than the compound(s) of the invention. The choice of carrier or excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as, for example, tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include, for example, suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in *Expert Opinion in Therapeutic Patents*, 11 (6), 981-986 by Liang and Chen (2001).

For tablet dosage forms, depending on dose, the drug may make up from about 1 wt % to about 80 wt % of the dosage form, more typically from about 5 wt % to about 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from about 1 wt % to about 25 wt %, preferably from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from about 0.25 wt % to about 10 wt %, preferably from about 0.5 wt % to about 3 wt % of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "*Pharmaceutical Dosage Forms: Tablets, Vol. 1*", by H. Lieberman and L. Lachman, Marcel Dekker, N.Y., N.Y., 1980 (ISBN 0-8247-6918-X).

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, *Pharmaceutical Technology On-line*, 25(2), 1-14 (2001). The use of chewing gum to achieve controlled release is described in WO 00/35298.

Kit-of-Parts

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Dosage

For administration to human patients, the total daily dose of the compounds of the invention is typically in the range of about 0.05 mg to about 100 mg depending, of course, on the mode of administration, preferred in the range of about 0.1 mg to about 50 mg and more preferred in the range of about 0.5 mg to about 20 mg. For example, oral administration may require a total daily dose of from about 1 mg to about 20 mg, while an intravenous dose may only require from about 0.5 mg to about 10 mg. The total daily dose may be administered in single or divided doses.

These dosages are based on an average human subject having a weight of about 65 kg to about 70 kg. The physician will readily be able to determine doses for subjects whose weight falls outside this range, such as infants and the elderly.

Combination

As discussed above, a compound of the invention exhibits 5-HT$_4$ agonist activity. A 5-HT$_4$ agonist of the present invention may be usefully combined with at least one other pharmacologically active agent or compound, particularly in the treatment of gastroesophageal reflux disease. For example, a 5-HT$_4$ agonist, particularly a compound of the formula (I), or a pharmaceutically acceptable salt or solvate thereof, as defined above, may be administered simultaneously, sequentially or separately in combination with one or more pharmacologically active agents selected from:

(i) histamine H$_2$ receptor antagonists, e.g. ranitidine, lafutidine, nizatidine, cimetidine, famotidine and roxatidine;

(ii) proton pump inhibitors, e.g. omeprazole, esomeprazole, pantoprazole, rabeprazole, tenatoprazole, ilaprazole and lansoprazole;

(iii) Acid pump antagonists, e.g. soraprazan, revaprazan (YH-1885), AZD-0865, CS-526, AU-2064 and YJA-20379-8;

(iv) oral antacid mixtures, e.g. Maalox®, Aludrox® and Gaviscon®;

(v) mucosal protective agents, e.g. polaprezinc, ecabet sodium, rebamipide, teprenone, cetraxate, sucralfate, chloropylline-copper and plaunotol;

(vi) GABA$_B$ agonists, e.g. baclofen and AZD-3355;

(vii) α2 agonists, e.g. clonidine, medetomidine, lofexidine, moxonidine, tizanidine, guanfacine, guanabenz, talipexole and dexmedetomidine;

(viii) Xanthin derivatives, e.g. Theophylline, aminophylline and doxofylline;

(ix) calcium channel blockers, e.g. aranidipine, lacidipine, falodipine, azelnidipine, clinidipine, lomerizine, diltiazem, gallopamil, efonidipine, nisoldipine, amlodipine, lercanidipine, bevantolol, nicardipine, isradipine, benidipine, verapamil, nitrendipine, barnidipine, propafenone, manidipine, bepridil, nifedipine, nilvadipine, nimodipine, and fasudil;

(x) benzodiazepine agonists, e.g. diazepam, zaleplon, zolpidem, haloxazolam, clonazepam, prazepam, quazepam, flutazolam, triazolam, lormetazepam, midazolam, tofisopam, clobazam, flunitrazepam and flutoprazepam;

(xi) prostaglandin analogues, e.g. Prostaglandin, misoprostol, treprostinil, esoprostenol, latanoprost, iloprost, beraprost, enprostil, ibudilast and ozagrel;

(xii) histamine H$_3$ agonists, e.g. R-alpha-methylhistamine and BP-294;

(xiii) anti-gastric agents, e.g. Anti-gastrin vaccine, itriglumide and Z-360;

(xiv) 5-HT$_3$ antagonists, e.g. dolasetron, palonosetron, alosetron, azasetron, ramosetron, mitrazapine, granisetron, tropisetron, E-3620, ondansetron and indisetron;

(xv) tricyclic antidepressants, e.g. imipramine, amitriptyline, clomipramine, amoxapine and lofepramine;

(xvi) GABA agonists, e.g. gabapentin, topiramate, cinolazepam, clonazepam, progabide, brotizolam, zopiclone, pregabalin and eszopiclone;

(xvii) opioid analgesics, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine and pentazocine;

(xviii) somatostatin analogues, e.g. octreotide, AN-238 and PTR-3173;

(xix) Cl Channel activator: e.g. lubiprostone;

(xx) selective serotonin reuptake inhibitors, e.g. sertraline, escitalopram, fluoxetine, nefazodone, fluvoxamine, citalopram, milnacipran, paroxetine, venlafaxine, tramadol, sibutramine, duloxetine, desvenlafaxine and dapoxetine;

(xxi) anticholinergics, e.g. dicyclomine and hyoscyamine;

(xxii) laxatives, e.g. Trifyba®, Fybogel®, Konsyl®, Isogel®, Regulan®, Celevac® and Normacol®;

(xxiii) fiber products, e.g. Metamucil;

(xxiv) antispasmodics, e.g.: mebeverine;

(xxv) dopamine antagonists, e.g. metoclopramide, domperidone and levosulpiride;

(xxvi) cholinergics, e.g. neostigmine (xxvii) AChE inhibitors, e.g. galantamine, metrifonate, rivastigmine, itopride and donepezil;

(xxviii) Tachykinin (NK) antagonists, particularly NK-3, NK-2 and NK-1 antagonists e.g. nepadutant, saredutant, talnetant, (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)phenyl]methylamino]-2-phenyl-piperidine (2S,3S).

Method for Assessing Biological Activities:

The 5-HT$_4$ receptor binding affinities of the compounds of this invention are determined by the following procedures.

Human 5-HT$_4$ Binding(1)

Human 5-HT$_{4(d)}$ transfected HEK293 cells were prepared and grown in-house. The collected cells were suspended in 50 mM HEPES (pH 7.4 at 4° C.) supplemented with protease inhibitor cocktail (Boehringer, 1:1000 dilution) and homogenized using a hand held Polytron PT 1200 disruptor set at full power for 30 sec on ice. The homogenates were centrifuged at 40,000×g at 4° C. for 30 min. The pellets were then resuspended in 50 mM HEPES (pH 7.4 at 4° C.) and centrifuged once more in the same manner. The final pellets were resuspended in an appropriate volume of 50 mM HEPES (pH 7.4 at 25° C.), homogenized, aliquoted and stored at −80° C. until use. An aliquot of membrane fractions was used for protein concentration determination using BCA protein assay kit (PIERCE) and ARVOsx plate reader (Wallac).

For the binding experiments, 25 µl of test compounds were incubated with 25 µl of [$^3$H]-GR113808 (Amersham, final 0.2 nM) and 150 µl of membrane homogenate and WGA-SPA beads (Amersham) suspension solutions (10 µg protein and 1 mg SPA beads/well) for 60 minutes at room temperature. Nonspecific binding was determined by 1 µM GR113808 (Tocris) at the final concentration. Incubation was terminated by centrifugation at 1000 rpm.

Receptor-bound radioactivity was quantified by counting with MicroBeta plate counter (Wallac).

All compounds of Examples showed 5HT$_4$ receptor affinity.

Human 5-HT$_4$ Binding(2)

Human 5-HT$_{4(d)}$ transfected HEK293 cells were prepared and grown in-house. The collected cells were suspended in 50 mM Tris buffer (pH 7.4 at 4° C.) supplemented with protease inhibitor cocktail (Boehringer, 1:1000 dilution) and homogenized using a hand held Polytron PT 1200 disruptor set at full power for 30 sec on ice. The homogenates were centrifuged at 40,000×g at 4° C. for 10 min. The pellets were then resuspended in 50 mM Tris buffer (pH 7.4 at 4° C.) and centrifuged once more in the same manner. The final pellets were resuspended in an appropriate volume of 50 mM Tris buffer (pH 7.4 at 25° C.) containing 10 mM MgCl$_2$, homogenized, aliquoted and stored at −80° C. until use. An aliquot of membrane fractions was used for protein concentration determination using BCA protein assay kit (PIERCE) and ARVOsx plate reader (Wallac).

For the binding experiments, 50 μl of test compounds were incubated with 50 μl of [$^3$H] 5-HT (Amersham, final 8.0 nM) and 400 μl of membrane homogenate (300 μg protein/tube) for 60 minutes at room temperature. Nonspecific binding was determined by 50 μM GR113808 (Tocris) at the final concentration. All incubations were terminated by rapid vacuum filtration over 0.2% PEI soaked glass fiber filter papers using BRANDEL harvester followed by three washes with 50 mM Tris buffer (pH 7.4 at 25° C.). Receptor-bound radioactivity was quantified by liquid scintillation counting using Packard LS counter.

All compounds of Examples showed 5HT$_4$ receptor affinity.

Agonist-induced cAMP Elevation in Human 5-HT$_{4(d)}$ Transfected HEK293 Cells

Human 5-HT$_{4(d)}$ transfected HEK293 cells were established in-house. The cells were grown at 37° C. and 5% CO$_2$ in DMEM supplemented with 10% FCS, 20 mM HEPES (pH 7.4), 200 μg/ml hygromycin B (Gibco), 100 units/ml penicillin and 100 μg/ml streptomycin.

The cells were grown to 60-80% confluence. On the previous day before treatment with compounds dialyzed FCS (Gibco) was substituted for normal and the cells were incubated overnight.

Compounds were prepared in 96-well plates (12.5 μl/well). The cells were harvested with PBS/1 mM EDTA, centrifuged and washed with PBS. At the beginning of the assay, cell pellet was resuspended in DMEM supplemented with 20 mM HEPES, 10 μM pargyline (Sigma) and 1 mM 3-isobutyl-1-methylxanthine (Sigma) at the concentration of 1.6×10$^5$ cells/ml and left for 15 minutes at room temperature. The reaction was initiated by addition of the cells into plates (12.5 μl/well). After incubation for 15 minutes at room temperature, 1% Triton X-100 was added to stop the reaction (25 μl/well) and the plates were left for 30 minutes at room temperature. Homogenous time-resolved fluorescence-based cAMP (Schering) detection was made according to the manufacturer's instruction. ARVOsx multilabel counter (Wallac) was used to measure HTRF (excitation 320 nm, emission 665 nm/620 nm, delay time 50 μs, window time 400 μs). Data was analyzed based on the ratio of fluorescence intensity of each well at 620 nm and 665 nm followed by cAMP quantification using cAMP standard curve. Enhancement of cAMP production elicited by each compound was normalized to the amount of cAMP produced by 1000 nM serotonin (Sigma).

All compounds of Examples showed 5HT$_4$ receptor agonistic activity.

Half-Life in Human Liver Microsomes (HLM)

Test compounds (1 μM) were incubated with 3.3 mM MgCl$_2$ and 0.78 mg/mL HLM (HL101) in 100 mM potassium phosphate buffer (pH 7.4) at 37° C. on the 96-deep well plate. The reaction mixture was split into two groups, a non-P450 and a P450 group. NADPH was only added to the reaction mixture of the P450 group. An aliquot of samples of P450 group was collected at 0, 10, 30, and 60 min time point, where 0 min time point indicated the time when NADPH was added into the reaction mixture of P450 group. An aliquot of samples of non-P450 group was collected at −10 and 65 min time point. Collected aliquots were extracted with acetonitrile solution containing an internal standard. The precipitated protein was spun down in centrifuge (2000 rpm, 15 min). The compound concentration in supernatant was measured by LC/MS/MS system.

The half-life value was obtained by plotting the natural logarithm of the peak area ratio of compounds/internal standard versus time. The slope of the line of best fit through the points yields the rate of metabolism (k). This was converted to a half-life value using following equations:

Half-life=ln 2/k

EXAMPLES

The invention is illustrated in the following non-limiting examples in which, unless stated otherwise: all operations were carried out at room or ambient temperature, that is, in the range of 18-25° C.; evaporation of solvent was carried out using a rotary evaporator under reduced pressure with a bath temperature of up to 60° C.; reactions were monitored by thin layer chromatography (TLC) and reaction times are given for illustration only; melting points (mp) given are uncorrected (polymorphism may result in different melting points); the structure and purity of all isolated compounds were assured by at least one of the following techniques: TLC (Merck silica gel 60 F$_{254}$ precoated TLC plates or Merck NH$_2$ gel (an amine coated silica gel) F$_{254a}$ precoated TLC plates), mass spectrometry, nuclear magnetic resonance spectra (NMR), infrared absorption spectra (IR) or microanalysis. Yields are given for illustrative purposes only. Workup with a cation-exchange column was carried out using SCX cartridge (Varian Bond-Elute), which was preconditioned with methanol. Flash column chromatography was carried out using Merck silica gel 60 (63-200 μm), Wako silica gel 300HG (40-60 μm), Fuji Silysia NH gel (an amine coated silica gel) (30-50 μm), Biotage KP-SIL (32-63 μm) or Biotage AMINOSILICA (an amine coated silica gel) (40-75 μm). Preparative TLC was carried out using Merck silica gel 60 F$_{254}$ precoated TLC plates (0.5 or 1.0 mm thickness). Low-resolution mass spectral data (EI) were obtained on an Integrity (Waters) mass spectrometer. Low-resolution mass spectral data (ESI) were obtained on ZMD™ or ZQ™ (Waters) and mass spectrometer. NMR data were determined at 270 MHz (JEOL JNM-LA 270 spectrometer), 300 MHz (JEOL JNM-LA300 spectrometer) or 600 MHz (Bruker AVANCE 600 spectrometer) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, quint=quintet, m=multiplet, br.=broad, etc. IR spectra were measured by a Fourier transform infrared spectrophotometer (Shimazu FTIR-8300). Chemical symbols have their usual meanings; bp (boiling point), mp (melting point), rt (room temperature), L (liter(s)), mL (milliliter(s)), g (gram(s)), mg (milligram(s)), mol (moles), mmol (millimoles), eq. (equivalent(s)), quant. (quantitative yield).

Example 1

N-[Cis-6-(2-hydroxyethyl)piperidin-3-Yl]-1-isopropyl-1H-indazole-3-carboxamide

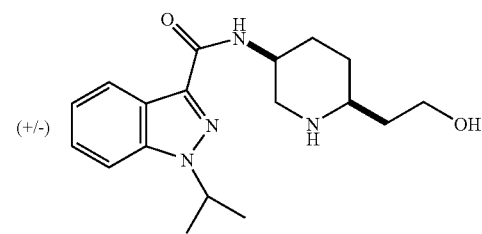

Step 1. tert-Butyl ethyl (5-nitropyridin-2-yl)malonate

To a stirred suspension of 2-chloro-5-nitropyridine (7.66 g, 48.3 mmol), sodium hydride (60% in mineral oil, 2.13 g, 53.1 mmol) in N,N-dimethylformamide (100 mL) was added tert-butyl ethyl malonate (10.0 g, 53.1 mmol) dropwise at room temperature, and the mixture was stirred at room temperature for 20 h. The mixture was washed with water (300 mL×5), brine (100 mL), dried over magnesium sulfate and concentrated under reduced pressure. The resulting residue was chromatographed on a column of silica gel eluting with n-hexane/ethyl acetate (5:1) to give 12.3 g (82%) of the title compound as a brown oil.

$^1$H NMR (CDCl$_3$) δ 9.38 (1H, dd, J=2.8, 0.6 Hz), 8.51 (1H, dd, J=8.8, 2.8 Hz), 7.77 (1H, dd, J=8.8, 0.6 Hz), 4.99 (1H, s), 4.33-4.21 (2H, m), 1.48 (9H, s), 1.30 (3H, t, J=7.2 Hz).

Step 2. Ethyl (5-nitropyridin-2-yl)acetate

To a stirred solution of tert-butyl ethyl (5-nitropyridin-2-yl)malonate (6.93 g, 22.3 mmol, step 1 of Example 1) in dichloromethane (75 mL) was added trifluoroacetic acid (7.64 g, 67.0 mmol) at room temperature, and the mixture was stirred at room temperature for 20 h. The mixture was washed with saturated aqueous sodium hydrogencarbonate solution, dried over magnesium sulfate and concentrated under reduced pressure. The resulting residue was chromatographed on a column of silica gel eluting with n-hexane/ethyl acetate (5:1 to 4:1) to give 3.27 g (70%) of the title compound as an orange oil.

$^1$H NMR (CDCl$_3$) δ 9.38 (1H, d, J=2.6 Hz), 8.47 (1H, dd, J=8.6, 2.6 Hz), 7.55 (1H, d, J=8.6 Hz), 4.22 (2H, q, J=7.2 Hz), 3.99 (2H, s), 1.28 (3H, t, J=7.2 Hz).

Step 3. Ethyl (5-aminopyridin-2-yl)acetate

The mixture of ethyl (5-nitropyridin-2-yl)acetate (3.27 g, 15.6 mmol, step 2 of Example 1) and 5 wt. % palladium on carbon (320 mg) in methanol (25 mL) was stirred under hydrogen (1 atom) at room temperature for 4 h. The mixture was filtered through a pad of Celite washing with methanol and the filtrate was concentrated to give 2.98 g (quant.) of the title compound as a yellow oil.

$^1$H NMR (CDCl$_3$) δ 8.04 (1H, d, J=2.8 Hz), 7.08 (1H, d, J=8.3 Hz), 6.96 (1H, dd, J=8.3, 2.8 Hz), 4.17 (2H, q, J=7.2 Hz), 3.72 (2H, s), 3.69 (2H, br.), 1.25 (3H, t, J=7.2 Hz).

Step 4. Ethyl {5-[(tert-butoxycarbonyl)amino]pyridin-2-yl}acetate

To a stirred solution of ethyl (5-aminopyridin-2-yl)acetate (2.80 g, 15.6 mmol, step 3 of Example 1) in 1,4-dioxane (22 mL) was added di-tert-butyl dicarbonate (4.08 g, 18.7 mmol) at room temperature. The mixture was refluxed for 18 h. After cooling, the mixture was quenched with water (200 mL), extracted with ethyl acetate (60 mL×5). The combined organic layer was washed with water (60 mL×5), brine (50 mL), dried over magnesium sulfate and concentrated under reduced pressure. The resulting residue was chromatographed on a column of silica gel eluting with n-hexane/ethyl acetate (2:1) to give 3.72 g (85%) of the title compound as a yellow crystal.

$^1$H NMR (CDCl$_3$) δ 8.36 (1H, d, J=2.6 Hz), 8.03-7.91 (1H, m), 7.24 (1H, d, J=8.4 Hz), 6.67 (1H, br.), 4.18 (2H, q, J=7.1 Hz), 3.79 (2H, s), 1.52 (9H, s), 1.25 (3H, t, J=7.1 Hz).

Step 5. Ethyl {cis-5-[(tert-butoxycarbonyl)amino]piperidin-2-yl}acetate

The mixture of ethyl {5-[(tert-butoxycarbonyl)amino]pyridin-2-yl}acetate (3.72 g, 15.6 mmol, step 4 of Example 1) and platinum oxide (300 mg) in ethanol (6 mL) and acetic acid (6 mL) was stirred under hydrogen (4 atom) at room temperature for 8 h. The mixture was filtered through a pad of Celite washing with ethanol and the filtrate was concentrated. The resulting residue was diluted with 2N aqueous sodium hydroxide solution (100 mL), and extracted with dichloromethane (100 mL×3). The combined organic layer was dried over magnesium sulfate, and concentrated under reduced pressure. The resulting residue was chromatographed on a column of silica gel eluting with dichloromethane/methanol (20:1) to give 2.48 g (65%) of the title compound as a colorless oil. (trans isomer 559 mg, 15% yield)

MS (ESI) m/z: 287 (M+H)$^+$.

Step 6. Ethyl {cis-1-benzyl-5-[(tert-butoxycarbonyl)amino]piperidin-2-yl}acetate To a stirred solution of ethyl {cis-5-[(tert-butoxycarbonyl)amino]piperidin-2-yl}acetate (2.25 g, 7.86 mmol, step 5 of Example 1), N,N-diisopropylethylamine (1.12 g, 8.64 mmol) in acetonitrile (45 mL) was added benzyl bromide (1.48 g, 8.64 mmol) at room temperature. After stirring at room temperature for 28 h, the mixture was concentrated under reduced pressure. The resulting residue was dissolved in ethyl acetate (250 mL). The organic solution was washed with water (100 mL×3), brine (50 mL), dried over magnesium sulfate, and concentrated under reduced pressure. The resulting residue was chromatographed on a column of silica gel eluting with n-hexane/ethyl acetate (4:1) to give 2.44 g (82%) of the title compound as a colorless oil.

MS (ESI) m/z: 377 (M+H)$^+$.

$^1$H NMR (CDCl$_3$) δ 7.34-7.20 (5H, m), 4.94-4.80 (1H, m), 4.14 (2H, q, J=7.3 Hz), 3.88-3.83 (1H, m), 3.76-3.61 (1H, m), 3.32 (1H, d, J=13.4 Hz), 3.00-2.85 (1H, m), 2.69 (1H, dd, J=14.7, 4.9 Hz), 2.58-2.35 (3H, m), 1.76-1.59 (4H, m), 1.41 (9H, s), 1.25 (3H, t, J=7.3 Hz).

Step 7. Ethyl (cis-5-amino-1-benzylpiperidin-2-yl)acetate

A mixture of ethyl {cis-1-benzyl-5-[(tert-butoxycarbonyl)amino]piperidin-2-yl}acetate (2.0 g, 5.31 mmol, step 6 of Example 1) and 10% hydrochloric acid in methanol was stirred at room temperature for 20 h. The mixture was concentrated under reduced pressure. The resulting residue was dissolved in dichloromethane/methanol (10/1, 10 mL). The solution was filtered through amine-silica gel washing with dichloromethane/methanol (10/1, 200 mL). The filtrate was concentrated under reduced pressure to give 1.65 g (quant.) of the title compound as a brown amorphous solid.

MS (ESI) m/z: 277 (M+H)$^+$.

$^1$H NMR (CDCl$_3$) δ 7.38-7.19 (5H, m), 4.08 (2H, q, J=7.1 Hz), 3.83-3.57 (3H, m), 3.55-3.42 (1H, m), 3.19-3.04 (1H, m), 2.95-2.66 (3H, m), 2.63-2.47 (1H, m), 2.07-1.69 (4H, m), 1.38-1.25 (1H, m), 1.20 (3H, t, J=7.1 Hz).

Step 8. 2-[cis-5-Amino-1-benzylpiperidin-2-yl]ethanol

To a stirred suspension of lithium aluminum hydride (97 mg, 2.55 mmol) in tetrahydrofuran (5 mL) was added a solution of ethyl [cis-5-amino-1-benzylpiperidin-2-yl]acetate (352 mg, 1.27 mmol, step 7 of Example 1) in tetrahydrofuran (4 mL) at 0° C., and the mixture was stirred at 0° C. for 1 h, then stirred at room temperature for 1 h. The mixture was quenched with water (0.1 mL) at 0° C., and stirred for 30 min at 0° C. 15% aqueous sodium hydroxide solution (0.1 mL) was added at 0° C., and the mixture was stirred at room temperature for 30 min. Water (0.3 mL) was added, and the mixture was stirred at room temperature for 30 min. The mixture was filtered through Celte pad washing with tetrahydrofuran (100 mL). The filtrate was concentrated under reduced pressure to give 322 mg (quant.) of the title compound as a slightly yellow oil.

$^1$H NMR (CDCl$_3$) δ 7.48-7.24 (5H, m), 4.07-3.65 (4H, m), 3.13-2.82 (2H, m), 2.79-2.52 (2H, m), 2.38-1.76 (6H, m), 1.58-1.40 (3H, m).

Step 9. N-[cis-1-Benzyl-6-(2-hydroxyethyl)piperidin-3-yl]-1-isopropyl-1H-indazole-3-carboxamide To a stirred solution of 1-isopropyl-1H-indazole-3-carboxylic acid (235 mg, 1.15 mmol), 2-[cis-5-amino-1-benzylpiperidin-2-yl]ethanol (322 mg, 1.37 mmol, step 8 of Example 1), N,N-diisopropylethylamine (177 mg, 1.37 mmol) in N,N-dimethylformamide (3 mL) was added diethyl cyanophosphonate (223 mg, 1.37 mmol) at room temperature. After stirring at room temperature for 20 h, the mixture was concentrated under reduced pressure. The resulting residue was chromatographed on a column of silica gel eluting with dichloromethane/methanol/25% ammonium hydroxide (10:1:0.2) to give 276 mg (52%) of the title compound as a colorless oil.

MS (ESI) m/z: 421 (M+H)$^+$.

$^1$H NMR (CDCl$_3$) δ 8.36 (1H, d, J=8.3 Hz), 7.47-7.19 (9H, m), 4.89 (1H, septet, J=6.6 Hz), 4.43-4.32 (1H, m), 4.17 (1H, d, J=13.2 Hz), 3.91-3.84 (1H, m), 3.79-3.65 (2H, m), 2.96 (1H, dd, J=13.2, 8.6 Hz), 2.86-2.79 (1H, m), 2.68 (1H, dd, J=12.7, 3.5 Hz), 2.23-2.10 (1H, m), 2.03-1.80 (3H, m), 1.65-1.62 (9H, m).

Step 10. N-[cis-6-(2-Hydroxyethyl)piperidin-3-yl]-1-isopropyl-1H-indazole-3-carboxamide The mixture of N-[cis-1-benzyl-6-(2-hydroxyethyl)piperidin-3-yl]-1-isopropyl-1H-indazole-3-carboxamide (276 mg, 0.66 mmol, step 9 of Example 1) and 10 wt. % palladium on carbon (30 mg) in methanol (5 mL) was stirred under hydrogen (1 atom) at room temperature for 4 h. The mixture was filtered through a pad of Celite washing with methanol and the filtrate was concentrated under reduced pressure. The resulting residue was chromatographed on a column of silica gel eluting with dichloromethane/methanol/25% ammonium hydroxide (10:1:0.2) to give 146 mg (67%) of the title compound as a white crystal.

MS (ESI) m/z: 331 (M+H)$^+$.

IR (KBr) ν: 3300, 1654, 1534, 1202, 1088, 1055, 951, 877, 774 cm$^{-1}$ $^1$H NMR (CDCl$_3$) δ 8.38 (1H, d, J=7.9 Hz), 7.58 (1H, d, J=7.9 Hz), 7.48-7.36 (2H, m), 7.29-7.24 (1H, m), 4.89 (1H, septet, J=6.6 Hz), 4.27-4.22 (1H, m), 3.94-3.75 (2H, m), 3.19-3.13 (1H, m), 2.98-2.87 (2H, m), 2.08-2.01 (1H, m), 1.86-1.55 (5H, m), 1.63 (6H, d, J=6.6 Hz). Signals due to NH, OH were not observed.

Anal. Calcd. for C$_{18}$H$_{26}$N$_4$O$_2$.0.1 H$_2$O: C, 65.07; H, 7.95; N, 16.86. Found: C, 64.86; H, 7.86; N, 16.84.

Example 2

N-{Cis-6-[(4-hydroxytetrahydro-2H-pyran-4-Yl)methyl]piperidin-3-Yl}-1-isopropyl-1H-indazole-3-carboxamide

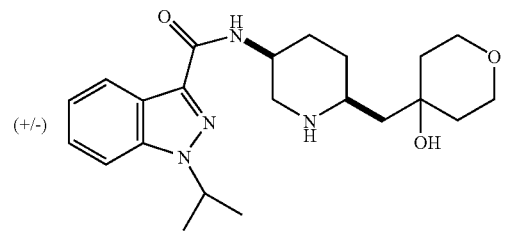

(+/-)

Step 1. 6-[(4-Hydroxytetrahydro-2H-pyran-4-yl)methyl]pyridin-3-ol

To a stirred suspension of 6-methylpyridin-3-ol (5.01 g, 45.9 mmol) in tetrahydrofuran (200 mL) was added n-butyllithium solution (1.6 M in n-hexane, 63 mL, 101 mmol) dropwise at −20° C. After addition, the mixture was allowed to warm to room temperature and stirred at the same temperature for 1 h. Then the mixture was cooled to −78° C., and tetrahydro-4H-pyran-4-one (5.06 g, 50.5 mmol) was added dropwise. The mixture was allowed to warm to room temperature over 20 h. The mixture was quenched with acetic acid (11.6 mL) and concentrated under reduced pressure. The resulting residue was chromatographed on a column of silica gel eluting with acetone/n-hexane (1:1 to 2:1) to give 7.87 g (82%) of the title compound as a yellow oil.

$^1$H NMR (CDCl$_3$) δ 8.14 (1H, d, J=2.8 Hz), 7.19 (1H, dd, J=8.3, 2.8 Hz), 7.05 (1H, d, J=8.4 Hz), 6.38 (1H, br.), 3.87-3.71 (4H, m), 2.88 (2H, s), 1.73-1.64 (2H, m), 1.55-1.51 (2H, m).

A signal due to OH was not observed.

Step 2. tert-Butyl 5-hydroxy-2-[(4-hydroxytetrahydro-2H-pyran-4-yl)methyl]piperidine-1-carboxylate The mixture of 6-[(4-hydroxytetrahydro-2H-pyran-4-yl)methyl]pyridin-3-ol (4.13 g, 19.74 mmol, step 1 of Example 2) and platinum oxide (409 mg) in acetic acid (17.6 mL) was stirred under hydrogen (4 atom) at room temperature for 8 h. The mixture was filtered through a pad of Celite washing with acetic acid (50 mL) and the filtrate was concentrated under reduced pressure. The resulting residue was dissolved in methanol (100 mL). To the resulting solution were added triethylamine (9.99 g, 98.7 mmol), di-tert-butyl dicarbonate (6.46 g, 29.6 mmol) and the mixture was stirred at room temperature for 16 h.

The mixture was concentrated under reduced pressure and the resulting residue was chromatographed on a column of silica gel eluting with n-hexane/ethyl acetate (1:2) to give 2.32 g (37%) of the title compound as a colorless oil.

MS (ESI) m/z: 216 (M+H)$^+$ (−BOC).

Step 3. tert-Butyl trans-2-[(4-hydroxytetrahydro-2H-pyran-4-yl)methyl]-5-[(methylsulfonyl)oxy]piperidine-1-carboxylate To a stirred solution of tert-butyl 5-hydroxy-2-[(4-hydroxytetrahydro-2H-pyran-4-yl)methyl]piperidine-1-carboxylate (1.92 g, 6.09 mmol, step 2 of Example 2), triethylamine (739 mg, 7.30 mmol) in dichloromethane (27 mL) was added methanesulfonyl chloride (836 mg, 7.30 mmol) at 0° C., and the mixture was allowed to warm to room temperature over 20 h. The mixture was quenched with water (50 mL). The organic layer was separated and the aqueous layer was extracted with dichloromethane (50 mL×3). The combined organic layer was dried over magnesium sulfate and concentrated under reduced pressure. The resulting residue was chromatographed on a column of silica gel eluting with n-hexane/ethyl acetate (1:5) to give 673 mg (28%) of the title compound as a white crystal. (cis isomer, 634 mg, 26% yield)

MS (ESI) m/z: 294 (M+H)$^+$ (−BOC).

$^1$H NMR (CDCl$_3$) δ 4.87 (1H, br.), 4.71-4.57 (1H, m), 4.43-4.29 (1H, m), 3.89-3.44 (5H, m), 3.15-3.08 (1H, m), 3.05 (3H, s), 2.20-1.81 (4H, m), 1.72-1.55 (4H, m), 1.47 (9H, s), 1.42-1.30 (2H, m).

Step 4. tert-Butyl cis-5-azido-2-[(4-hydroxytetrahydro-2H-pyran-4-yl)methyl]piperidine-1-carboxylate To a stirred solution of tert-butyl trans-2-[(4-hydroxytetrahydro-2H-pyran-4-yl)methyl]-5-[(methylsulfonyl)oxy]piperidine-1-carboxylate (673 mg, 1.71 mmol, step 3 of Example 2) in N,N-dimethylformamide (4 mL) was added sodium azide (334 mg, 5.13 mmol) at room temperature and the mixture was stirred at 80° C. for 24 h. After cooling, the mixture was quenched with water (50 mL), and extracted with ethyl acetate (50 mL×4). The combined organic layer was washed with water (50 mL×4), brine (30 mL), dried over magnesium sulfate and concentrated under reduced pressure. The resulting residue was chromatographed on a column of silica gel eluting with n-hexane/ethyl acetate (2:1) to give 480 mg (82%) of the title compound as a white crystal.

MS (ESI) m/z: 241 (M+H)$^+$ (−BOC).

$^1$H NMR (CDCl$_3$) δ 4.54 (1H, br.), 4.16-4.03 (1H, m), 3.92-3.59 (5H, m), 3.43-3.31 (1H, m), 2.71-2.62 (1H, m), 2.05-1.94 (2H, m), 1.85-1.33 (7H, m), 1.46 (9H, s). A signal due to OH was not observed.

Step 5. tert-Butyl cis-5-amino-2-[(4-hydroxytetrahydro-2H-pyran-4-yl)methyl]piperidine-1-carboxylate The mixture of tert-butyl cis-5-azido-2-[(4-hydroxytetrahydro-2H-pyran-4-yl)methyl]piperidine-1-carboxylate (253 mg, 0.743 mmol, step 4 of Example 2) and 10 wt. % palladium on carbon (50 mg) in methanol (5 mL) was stirred under hydrogen (4 atom) at room temperature for 7 h. The mixture was filtered through a pad of Celite washing with methanol and the filtrate was concentrated to give 244 mg (quant.) of the title compound as a colorless oil.

MS (ESI) m/z: 215 (M+H)$^+$ (−BOC).

$^1$H NMR (CDCl$_3$) δ 4.50 (1H, br.), 4.00-3.64 (6H, m), 2.74 (1H, br.), 2.53-2.44 (1H, m), 2.05-1.50 (7H, m), 1.45 (9H, s), 1.38-1.08 (5H, m).

Step 6. tert-Butyl cis-2-[(4-hydroxytetrahydro-2H-pyran-4-yl)methyl]-5-{[(1-isopropyl-1H-indazol-3-yl)carbonyl]amino}piperidine-1-carboxylate To a stirred solution of 1-isopropyl-1H-indazole-3-carboxylic acid (126 mg, 0.619 mmol), tert-butyl cis-5-amino-2-[(4-hydroxytetrahydro-2H-pyran-4-yl)methyl]piperidine-1-carboxylate (234 mg, 0.743 mmol, step 5 of Example 2), N,N-diisopropylethylamine (96 mg, 0.743 mmol) in N,N-dimethylformamide (3 mL) was added diethyl cyanophosphonate (121 mg, 0.743 mmol) at room temperature, and the mixture was stirred at the same temperature for 18 h. The mixture was concentrated under reduced pressure and the resulting residue was chromatographed on a column of silica gel eluting with n-hexane/ethyl acetate (1:1) to give 292 mg (94%) of the title compound as a colorless oil.

$^1$H NMR (CDCl$_3$) δ 8.39 (1H, d, J=8.6 Hz), 7.49-7.39 (2H, m), 7.31-7.26 (1H, m), 6.87 (1H, d, J=8.6 Hz), 4.89 (1H, septet, J=6.6 Hz), 4.61 (1H, br.), 4.38-4.03 (3H, m), 3.92-3.63 (5H, m), 2.79 (1H, t, J=12.5 Hz), 2.14-1.85 (3H, m), 1.71-1.58 (10H, m), 1.47 (9H, s), 1.45-1.37 (1H, m).

A signal due to OH was not observed.

Step 7. N-{cis-6-[(4-Hydroxytetrahydro-2H-pyran-4-yl)methyl]piperidin-3-yl}-1-isopropyl-1H-indazole-3-carboxamide The mixture of tert-butyl cis-2-[(4-hydroxytetrahydro-2H-pyran-4-yl)methyl]-5-{[(1-isopropyl-1H-indazol-3-yl)carbonyl]amino}piperidine-1-carboxylate (292 mg, 0.583 mmol, step 6 of Example 2) and 10% hydrochloric acid in methanol (3 mL) was stirred at room temperature for 20 h. The mixture was concentrated under reduced pressure and the resulting residue was dissolved in dichloromethane/methanol (10/1, 10 mL). The solution was filtered through amine-silica gel washing with dichloromethane/methanol (10/1, 200 mL). The filtrate was concentrated under reduced pressure and the resulting residue was chromatographed on a column of silica gel eluting with dichloromethane/methanol/25% ammonium hydroxide (10:1:0.2) to give 249 mg (99%) of the title compound as a white crystal.

MS (ESI) m/z: 401 (M+H)$^+$, 399 (M−H)$^-$.

IR (KBr) ν: 3298, 1641, 1533, 1366, 1195, 1099, 1016, 818, 776 cm$^{-1}$ $^1$H NMR (CDCl$_3$) δ 8.37 (1H, d, J=8.6 Hz), 7.49-7.38 (2H, m), 7.30-7.25 (1H, m), 7.17-7.15 (1H, m), 4.90 (1H, septet, J=6.6 Hz), 4.16-4.07 (1H, m), 3.91-3.67 (4H, m), 3.21-3.08 (2H, m), 2.94 (1H, dd, J=13.8, 3.0 Hz), 2.01-1.95 (2H, m), 1.79-1.40 (10H, m), 1.64 (6H, d, J=6.6 Hz).

Anal. Calcd. for $C_{22}H_{32}N_4O_3$: C, 65.97; H, 8.05; N, 13.99. Found: C, 65.72; H, 8.08; N, 13.72.

The fraction-1 (62 mg) and fraction-2 (48 mg) were prepared from racemic N-{cis-6-[(4-hydroxytetrahydro-2H-pyran-4-yl)methyl]piperidin-3-yl}-1-isopropyl-1H-indazole-3-carboxamide (150 mg) by HPLC as follows.

Isolation Condition

Column: CHIRALPAK® AS-H (20 mm I.D.×250 mm, DAICEL)

Mobile phase: n-hexane/2-propanol/diethylamine (90/10/0.1)

flow rate: 18.9 mL/min (+)-N-{cis-6-[(4-hydroxytetrahydro-2H-Pyran-4-yl)methyl]piperidin-3-yl}-1-isopropyl-1H-indazole-3-carboxamide (Fraction-1)

NMR: spectrum data were identical with those of the racemate optical rotation: $[\alpha]_D^{23}$=+10.8° (C=0.25, Methanol)

retention time: 17 min (−)—N-{cis-6-[(4-hydroxytetrahydro-2H-pyran-4-yl)methyl]piperidin-3-yl}-1-isopropyl-1H-indazole-3-carboxamide (Fraction-2)

NMR: spectrum data were identical with those of the racemate optical rotation: $[\alpha]_D^{23}$=−10.8° (C=0.25, Methanol)

retention time: 21 min

Example 3

N-[Cis-6-(2-Hydroxy-2-Methylpropyl)Piperidin-3-YL]-1-Isopropyl-1H-Indazole-3-Carboxamide

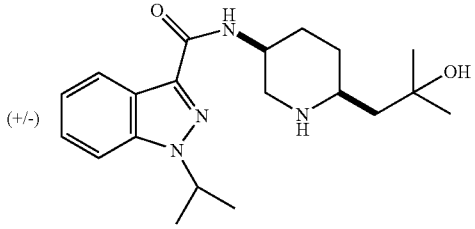

(+/-)

Step 1. 6-(2-Hydroxy-2-methylpropyl)pyridin-3-ol

To a stirred suspension of 6-methylpyridin-3-ol (2.54 g, 23.3 mmol) in tetrahydrofuran (100 mL) was added n-butyl-lithium solution (1.6 M in n-hexane, 32 mL, 51.2 mmol) dropwise at −20° C. After addition, the mixture was allowed to warm to room temperature and stirred at the same temperature for 1 h. Then the mixture was cooled to −78° C., and acetone (2.03 g, 35.0 mmol) was added dropwise. The resulting mixture was allowed to warm to room temperature over 20 h. The mixture was quenched with acetic acid (5.8 mL) and concentrated under reduced pressure. The resulting residue was chromatographed on a column of silica gel eluting with acetone/n-hexane (1:1) to give 3.90 g (quant.) of the title compound as a yellow oil.

MS (ESI) m/z: 168 (M+H)$^+$, 166 (M−H)$^-$.

$^1$H NMR (CDCl$_3$) δ 8.15 (1H, d, J=2.8 Hz), 7.21 (1H, dd, J=8.4, 2.8 Hz), 7.04 (1H, d, J=8.4 Hz), 6.30 (2H, br.), 2.86 (2H, s), 1.25 (6H, s).

Step 2. tert-Butyl 5-hydroxy-2-(2-hydroxy-2-methylpropyl)piperidine-1-carboxylate The title compound was prepared according to the procedure described in step 2 of Example 2 from 6-(2-hydroxy-2-methylpropyl)pyridin-3-ol (step 1 of Example 3).

MS (ESI) m/z: 174 (M+H)$^+$ (−BOC).

Step 3. tert-Butyl tans-2-(2-hydroxy-2-methylpropyl)-5-[(methylsulfonyl)oxy]piperidine-1-carboxylate The title compound was prepared according to the procedure described in step 3 of Example 2 from tert-butyl 5-hydroxy-2-(2-hydroxy-2-methylpropyl)piperidine-1-carboxylate (step 2 of Example 3).

MS (ESI) m/z: 252 (M+H)$^+$ (−BOC).

$^1$H NMR (CDCl$_3$) δ 4.86 (1H, br.), 4.59 (1H, br.), 4.45-4.26 (1H, m), 3.30-3.08 (1H, m), 3.05 (3H, s), 2.18-1.67 (5H, m), 1.46 (9H, s), 1.40 (1H, br.), 1.26 (3H, s), 1.19 (3H, s).

A signal due to OH was not observed.

Step 4. tert-Butyl cis-5-azido-2-(2-hydroxy-2-methylpropyl)piperidine-1-carboxylate The title compound was prepared according to the procedure described in step 4 of Example 2 from tert-butyl tans-2-(2-hydroxy-2-methylpropyl)-5-[(methylsulfonyl)oxy]piperidine-1-carboxylate (step 3 of Example 3).

$^1$H NMR (CDCl$_3$) δ 4.57-4.00 (3H, m), 3.44-3.26 (2H, m), 2.72-2.64 (1H, m), 2.04-1.87 (2H, m), 1.83-1.58 (2H, m), 1.47 (9H, s), 1.27 (3H, s), 1.19 (3H, s). A signal due to OH was not observed.

Step 5. tert-Butyl cis-5-amino-2-(2-hydroxy-2-methylpropyl)piperidine-1-carboxylate The title compound was prepared according to the procedure described in step 5 of Example 2 from tert-butyl cis-5-azido-2-(2-hydroxy-2-methylpropyl)piperidine-1-carboxylate (step 4 of Example 3).

$^1$H NMR (CDCl$_3$) δ 4.50 (2H, br.), 3.86-3.81 (1H, m), 3.10-3.07 (2H, m), 2.11-1.94 (2H, m), 1.81 (1H, tt, J=13.8, 3.9 Hz), 1.68-1.30 (2H, m), 1.47 (9H, s), 1.26 (3H, s), 1.19 (3H, s).

A signal due to NH$_2$, OH were not observed.

Step 6. tert-Butyl cis-2-(2-hydroxy-2-methylpropyl)-5-{[(1-isopropyl-1H-indazol-3-yl)carbonyl]amino}piperidine-1-carboxylate The title compound was prepared according to the procedure described in step 6 of Example 2 from tert-butyl cis-5-amino-2-(2-hydroxy-2-methylpropyl)piperidine-1-carboxylate (step 5 of Example 3).

MS (ESI) m/z: 359 (M+H)$^+$ (−BOC).

$^1$H NMR (CDCl$_3$) δ 8.39 (1H, d, J=8.1 Hz), 7.48-7.39 (2H, m), 7.31-7.26 (1H, m), 6.88 (1H, d, J=8.1 Hz), 4.89 (1H, septet, J=6.6 Hz), 4.57 (1H, br.), 4.33-4.29 (1H, m), 4.18-4.05 (2H, m), 2.79 (1H, t, J=11.8 Hz), 2.11-1.57 (5H, m), 1.62 (6H, d, J=6.6 Hz), 1.48 (9H, s), 1.29 (3H, s), 1.21 (3H, s).

A signal due to OH was not observed.

Step 7. N-[cis-6-(2-Hydroxy-2-methylpropyl)piperidin-3-yl]-1-isopropyl-1H-indazole-3-carboxamide The title compound was prepared according to the procedure described in step 7 of Example 2 from tert-butyl cis-2-(2-hydroxy-2-methylpropyl)-5-{[(1-isopropyl-1H-indazol-3-yl)carbonyl]amino}piperidine-1-carboxylate (step 6 of Example 3).

MS (ESI) m/z: 359 (M+H)$^+$, 357 (M−H)$^-$.

IR (KBr) ν: 3410, 1642, 1560, 1507, 1198, 1129, 776, 751 cm$^{-1}$ $^1$H NMR (CDCl$_3$) δ 8.37 (1H, d, J=8.1 Hz), 7.49-7.38 (2H, m), 7.29-7.25 (2H, m), 4.90 (1H, septet, J=6.6 Hz), 4.20-4.11 (1H, m), 3.17 (1H, dd, J=13.9, 3.7 Hz), 3.10-3.00 (1H, m), 2.95 (1H, dd, J=13.2, 2.9 Hz), 2.03-1.89 (2H, m), 1.78-1.59 (2H, m), 1.64 (6H, d, J=6.6 Hz), 1.52-1.40 (2H, m), 1.30 (3H, s), 1.24 (3H, s). A signal due to NH, OH was not observed.

Anal. Calcd. for C$_{20}$H$_{30}$N$_4$O$_2$.0.2 H$_2$O: C, 66.34; H, 8.46; N, 15.47. Found: C, 66.07; H, 8.36; N, 15.40.

The fraction-1 (7.0 mg) and fraction-2 (7.1 mg) were prepared from racemic N-{cis-6-[(4-hydroxytetrahydro-2H-pyran-4-yl)methyl]piperidin-3-yl}-1-isopropyl-1H-indazole-3-carboxamide (23 mg) by HPLC as follows.

Isolation Condition
Column: CHIRALPAK® AD-H (20 mm I.D.×250 mm, DAICEL)
Mobile phase: n-hexane/ethanol/diethylamine (90/10/0.1)
flow rate: 18.9 mL/min
(+)-N-{cis-6-[(4-hydroxytetrahydro-2H-pyran-4-yl)methyl]piperidin-3-yl}-1-isopropyl-1H-indazole-3-carboxamide (Fraction-1)
NMR: spectrum data were identical with those of the racemate
optical rotation: $[\alpha]_D^{22}$=+14.9° (C=0.33, Methanol)
retention time: 14 min
(−)-N-{cis-6-[(4-hydroxytetrahydro-2H-pyran-4-yl)methyl]piperidin-3-yl}-1-isopropyl-1H-indazole-3-carboxamide (Fraction-2)
NMR: spectrum data were identical with those of the racemate
optical rotation: $[\alpha]_D^{22}$=−21.6° (C=0.26, Methanol)
retention time: 17 min Example 4

1-Cyclobutyl-N-{CIS-6-[(4-Hydroxytetrahydro-2H-Pyran-4-YL)Methyl]Piperidin-3-YL}-1H-IndazolE-3-Carboxamide Ethanedioate

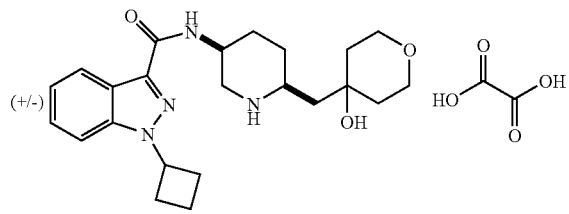

Step 1. Methyl 1-cyclobutyl-1H-indazole-3-carboxylate

To a suspension of sodium hydride (60% in mineral, 817 mg, 20.4 mmol) in N,N-dimethylformamide (30 mL) was added a solution of methyl 1H-indazole-3-carboxylate in N,N-dimethylformamide (20 mL) at room temperature. After stirring for 30 min, bromocyclobutane (3.45 g, 25.5 mmol) was added, and the mixture was stirred at 90° C. for 13 h. After cooling to room temperature, the mixture was poured onto saturated aqueous sodium hydrogencarbonate solution (200 mL), and the aqueous layer was extracted with ethyl acetate/toluene (3:1, 200 mL×2). The combined organic layer was dried over magnesium sulfate, and concentrated under reduced pressure. The residue was chromatographed on a column of silica gel eluting with ethyl acetate/n-hexane (1:6 then 1:5) to give 2.21 g (56%) of the title compound as a colorless oil.
MS (ESI) m/z: 199 (M-OMe)⁺.
¹H NMR (CDCl₃) δ8.23 (1H, d, J=10.3 Hz), 7.53 (1H, d, J=7.9 Hz), 7.44 (1H, t, J=7.3 Hz), 7.32 (1H, t, J=7.9 Hz), 5.17 (1H, t, J=7.9 Hz), 4.06 (3H, s), 3.00-2.81 (2H, m), 2.65-2.50 (2H, m), 2.06-1.90 (2H, m).

Step 2. 1-Cyclobutyl-1H-indazole-3-carboxylic acid

The mixture of methyl 1-cyclobutyl-1H-indazole-3-carboxylate (2.21 g, 9.60 mmol, step 1 of Example 4), 2 N aqueous sodium hydroxide solution (9.6 mL, 1.92 mmol), and ethanol (30 mL) was stirred at 60° C. for 2 h. After cooling to room temperature, 2 N hydrochloric acid (9.6 mL) was added, and the solvent was removed under reduced pressure. The residue was suspended in tetrahydrofuran (100 mL), and the solution was filtered through a pad of Celite. The filtrate was concentrated under reduced pressure to give 1.90 g (92%) of the title compound as a white solid. This material was used for the next step without further purification.
¹H NMR (CDCl₃) δ 8.09 (1H, d, J=7.9 Hz), 7.80 (1H, d, J=7.9 Hz), 7.47 (1H, t, J=7.3 Hz), 7.32 (1H, t, J=7.9 Hz), 5.39 (1H, t, J=8.6 Hz), 2.76-2.45 (4H, m), 1.99-1.83 (2H, m). A signal due to CO₂H was not observed.
MS (ESI) m/z: 217 (M+H)⁺.

Step 3. tert-Butyl cis-5-{[(1-cyclobutyl-1H-indazol-3-yl)carbonyl]amino}-2-[(4-hydroxytetrahydro-2H-pyran-4-yl)methyl]piperidine-1-carboxylate The mixture of 1-cyclobutyl-1H-indazole-3-carboxylic acid (135 mg, 0.63 mmol, step 2 of Example 4), tert-butyl cis-5-amino-2-[(4-hydroxytetrahydro-2H-pyran-4-yl)methyl]piperidine-1-carboxylate (197 mg, 6.27 mmol, step 5 of Example 2), diethyl cyanophosphonate (0.13 mL, 0.75 mmol), and N,N-diisopropylethylamine (0.16 mL, 0.94 mmol) in N,N-dimethylformamide (10 mL) was stirred at room temperature for 12 h. Then the mixture was poured onto aqueous saturated sodium hydrogencarbonate (100 mL), and the aqueous layer was extracted with ethyl acetate/toluene (3:1, 100 mL×3). The combined organic layer was concentrated under reduced pressure. The residue was chromatographed on a column of silica gel eluting with ethyl acetate/n-hexane (1:2) to give 112 mg (35%) of the title compound as a pale yellow amorphous.
¹H NMR (CDCl₃) δ 8.37 (1H, d, J=7.9 Hz), 7.48-7.37 (2H, m), 7.28 (1H, t, J=7.9 Hz), 6.92 (1H, d, J=8.6 Hz), 5.11 (1H, t, J=8.6 Hz), 4.67-4.55 (1H, m), 4.37-4.26 (1H, m), 4.20-4.05 (1H, m), 3.94-3.63 (5H, m), 2.90-2.72 (3H, m), 2.62-2.48 (2H, m), 2.18-1.85 (6H, m), 1.75-1.35 (5H, m), 1.47 (9H, s).
A signal due to OH was not observed.
MS (ESI) m/z: 413 (M-Boc)⁺.

Step 4. 1-Cylobutyl-N-{cis-6-[(4-hydroxytetrahydro-2H-pyran-4-yl)methyl]piperidin-3-yl}1H-indazole-3-carboxamide The mixture of tert-butyl cis-5-{[(1-cyclobutyl-1H-indazol-3-yl)carbonyl]amino}-2-[(4-hydroxytetrahydro-2H-pyran-4-yl)methyl]piperidine-1-carboxylate (112 mg, 0.22 mmol, step 3 of Example 4) and 10% hydrochloric acid in methanol (15 mL) was stirred at room temperature. After stirring for 1 h, the solvent was removed under reduced pressure. The residue was dissolved in methanol (2 mL), and this was poured onto saturated aqueous sodium hydrogencarbonate solution (50 mL). The aqueous layer was extracted with dichloromethane (50 mL×3). The combined organic layer was dried over magnesium sulfate, and concentrated under reduced pressure. The residue was chromatographed on a column of NH-silica gel eluting with ethyl acetate/n-hexane (5:1) to give 73 mg (81%) of the title compound as a colorless oil. This was treated with oxalic acid monohydrate (22 mg) in methanol (5 mL). The solvent was removed under reduced pressure to give 42 mg of the title compound as an ethanedioate salt as a white solid.
MS (ESI) m/z: 413 (M+H)⁺.
¹H NMR (CDC₃) δ8.44 (1H, d, J=7.9 Hz), 8.17 (1H, d, J=8.6 Hz), 7.80 (1H, d, J=8.6 Hz), 7.46 (1H, t, J=7.3 Hz), 7.29 (1H, t, J=7.9 Hz), 5.39 (1H, d, J=8.6 Hz), 4.42-4.32 (1H, m), 3.71-3.20 (7H, m), 2.82-2.66 (2H, m), 2.00-1.52 (14H, m). Signals due to OH, NH, and CO$_2$H were not observed.

Anal. Calcd. for C$_{23}$H$_{32}$N$_4$O$_3$·C$_2$H$_2$O$_4$·1.5 H$_2$O: C, 56.70; H, 7.04; N, 10.58. Found: C, 56.63; H, 6.88; N, 10.38.

Example 5

N-[Cis-6-(3-Hydroxypropyl)Piperidin-3-YL]-1-Isopropyl-1H-Indazole-3-Carboxamide Ethanedioate

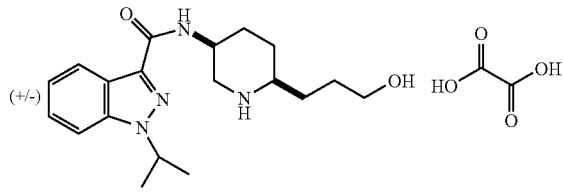

Step 1. Ethyl 3-(5-hydroxypyridin-2-yl)acrylate

The mixture of 6-bromopyridin-3-ol (5.22 g, 30.0 mmol), ethyl acrylate (4.51 g, 45.0 mmol), palladium acetate (175 mg, 0.78 mmol), tri-o-tolylphosphine (438 mg, 1.44 mmol), and triethylamine (4.55 g, 45.0 mmol) in N,N-dimethylformamide was placed in a sealed tube, and the mixture was stirred at 140° C. for 24 h. The mixture was quenched with water (100 mL), extracted with ethyl acetate (100 mL×3). The combined organic layer was washed with water (100 mL×4), brine (50 mL), dried over magnesium sulfate and concentrated under reduced pressure. The resulting residue was chromatographed on a column of silica gel eluting with n-hexane/ethyl acetate (1:1) to give 2.3 g (40%) of the title compound as a yellow oil. ((E), (Z) mixture)

MS (ESI) m/z: 192 (M−H)$^−$.

Step 2. Ethyl 3-(5-hydroxypyridin-2-yl)propanoate

The mixture of ethyl 3-(5-hydroxypyridin-2-yl)acrylate (2.30 g, 11.9 mmol, step 1 of Example 5) and 10 wt. % palladium on carbon (230 mg) in ethanol (5 mL) was stirred under hydrogen (1 atom) at room temperature for 24 h. The mixture was filtered through a pad of Celite, and washed with ethanol and the filtrate was concentrated under reduced pressure. The resulting residue was chromatographed on a column of silica gel eluting with n-hexane/ethyl acetate (1:1) to give 1.51 g (65%) of the title compound as a yellow crystal.

MS (ESI) m/z: 196 (M+H)$^+$, 194 (M−H)$^−$.

$^1$H NMR (CDCl$_3$) δ 8.19 (1H, d, J=2.6 Hz), 7.23 (1H, dd, J=8.6, 2.6 Hz), 7.15 (1H, d, J=8.6 Hz), 4.11 (2H, q, J=7.3 Hz), 3.06 (2H, t, J=7.3 Hz), 2.72 (2H, t, J=7.3 Hz), 1.21 (3H, t, J=7.3 Hz).

A signal due to OH was not observed.

Step 3. tert-Butyl trans-2-(3-ethoxy-3-oxopropyl)-5-hydroxypiperidine-1-carboxylate The mixture of ethyl 3-(5-hydroxypyridin-2-yl)propanoate (1.51 g, 7.73 mmol, step 2 of Example 5) and platinum oxide (300 mg) in acetic acid (67 mL) was stirred under hydrogen (4 atom) at room temperature for 11 h. The mixture was filtered through a pad of Celite washing with acetic acid and the filtrate was concentrated. The resulting residue was diluted with methanol (34 mL). To the resulting solution were added di-tert-butyl dicarbonate (2.53 g, 11.6 mmol), triethylamine (3.91 g, 38.7 mmol) at room temperature, and the resulting mixture was stirred at room temperature for 4 days. The resulting mixture was concentrated under reduced pressure. The resulting residue was chromatographed on a column of silica gel eluting with n-hexane/ethyl acetate (2:3 to 1:2) to give 625 mg (27%) of the title compound as a yellow oil. (cis isomer 500 mg, 21% yield)

MS (ESI) m/z: 202 (M+H)$^+$ (−BOC).

$^1$H NMR (CDCl$_3$) δ 4.27 (1H, br.), 4.13 (2H, q, J=6.6 Hz), 4.09-3.92 (2H, m), 3.00-2.94 (1H, m), 2.36-2.25 (2H, m), 2.13-2.00 (3H, m), 1.77-1.62 (3H, m), 1.45 (9H, s), 1.37-1.32 (1H, m), 1.25 (3H, t, J=7.3 Hz).

Step 4. tert-Butyl trans-2-(3-ethoxy-3-oxopropyl)-5-[(methylsulfonyl)oxy]piperidine-1-carboxylate To a stirred solution of tert-butyl trans-2-(3-ethoxy-3-oxopropyl)-5-hydroxypiperidine-1-carboxylate (625 mg, 2.07 mmol, step 3 of Example 5) and triethylamine (252 mg, 2.49 mmol) in dichloromethane (9.0 mL) was added methanesulfonyl chloride (285 g, 2.49 mmol) at 0° C. The resulting mixture was stirred at 0° C. for 2 h and then stirred at room temperature for 20 h. The mixture was quenched with water (30 mL), extracted with dichloromethane (30 mL×4). The combined organic layer was dried over magnesium sulfate and concentrated under reduced pressure to give 790 mg (quant.) of the title compound as a yellow oil. The resulting residue was used for the next reaction without purification.

$^1$H NMR (CDCl$_3$) δ 4.86 (1H, br.), 4.44-4.28 (2H, m), 4.13 (2H, q, J=6.6 Hz), 3.06 (3H, s), 3.04-2.92 (1H, m), 2.37-2.24 (2H, m), 2.15-1.80 (4H, m), 1.77-1.59 (2H, m), 1.46 (9H, s), 1.25 (3H, t, J=7.3 Hz).

Step 5. tert-Butyl cis-5-azido-2-(3-ethoxy-3-oxopropyl)piperidine-1-carboxylate

The title compound was prepared according to the procedure described in step 4 of Example 2 from tert-butyl trans-2-(3-ethoxy-3-oxopropyl)-5-[(methylsulfonyl)oxy]piperidine-1-carboxylate (step 4 of Example 5).

MS (ESI) m/z: 227 (M+H)$^+$ (−BOC).

$^1$H NMR (CDCl$_3$) δ 4.24 (2H, br.), 4.13 (2H, q, J=7.3 Hz), 3.32 (1H, br.), 2.60 (1H, br.), 2.31-2.25 (2H, m), 2.11-1.88 (2H, m), 1.75-1.57 (4H, m), 1.46 (9H, s), 1.26 (3H, t, J=7.3 Hz).

Step 6. tert-Butyl cis-5-amino-2-(3-ethoxy-3-oxopropyl)piperidine-1-carboxylate

The title compound was prepared according to the procedure described in step 5 of Example 2 from tert-butyl cis-5-azido-2-(3-ethoxy-3-oxopropyl)piperidine-1-carboxylate (step 5 of Example 5).

MS (ESI) m/z: 201 (M+H)$^+$ (−BOC).

$^1$H NMR (CDCl$_3$) δ 4.16 (2H, br.), 4.13 (2H, q, J=7.3 Hz), 2.78-2.61 (1H, m), 2.50-1.94 (4H, m), 1.84-1.54 (5H, m), 1.45 (9H, s), 1.39-1.30 (2H, m), 1.25 (3H, t, J=7.3 Hz).

Step 7. tert-Butyl cis-2-(3-ethoxy-3-oxopropyl)-5-{[(1-isopropyl-1H-indazol-3-yl)carbonyl]amino}piperidine-1-carboxylate The title compound was prepared according to the procedure described in step 6 of Example 2 from tert-butyl cis-5-amino-2-(3-ethoxy-3-oxopropyl)piperidine-1-carboxylate (step 6 of Example 5).

MS (ESI) m/z: 387 (M+H)$^+$ (−BOC), 386 (M−H)$^−$ (−BOC).

¹H NMR (CDCl₃) δ 8.38 (1H, d, J=8.1 Hz), 7.47-7.38 (2H, m), 7.30-7.25 (1H, m), 6.87 (1H, d, J=8.8 Hz), 4.88 (1H, septet, J=6.6 Hz), 4.33 (2H, br.), 4.14 (2H, q, J=7.3 Hz), 4.09-3.96 (1H, m), 2.73 (1H, t, J=12.5 Hz), 2.40-1.98 (4H, m), 1.94-1.66 (4H, m), 1.62 (6H, d, J=6.6 Hz), 1.47 (9H, s), 1.27 (3H, t, J=6.6 Hz).

Step 8. tert-Butyl cis-2-(3-hydroxypropyl)-5-{[(1-isopropyl-1H-indazol-3-yl)carbonyl]amino}piperidine-1-carboxylate To a stirred solution of tert-butyl cis-2-(3-ethoxy-3-oxopropyl)-5-{[(1-isopropyl-1H-indazol-3-yl) carbonyl]amino}piperidine-1-carboxylate (300 mg, 0.617 mmol, step 7 of Example 5) in tetrahydrofuran (7 mL) was added at 0° C. a solution of lithium borohydride (2M in tetrahydrofuran, 1.54 mL, 3.08 mmol), and the mixture was stirred at room temperature for 20 h. The mixture was quenched with water (20 mL), extracted with ethyl acetate (30 mL×3). The combined organic layer was washed with brine (20 mL), dried over magnesium sulfate and concentrated under reduced pressure to give 282 mg (quant.) of the title compound as a colorless oil. The resulting residue was used for the next reaction without purification.

MS (ESI) m/z: 345 (M+H)⁺ (−BOC).

¹H NMR (CDCl₃) δ 8.38 (1H, d, J=8.1 Hz), 7.47-7.38 (2H, m), 7.30-7.26 (1H, m), 6.86 (1H, d, J=8.1 Hz), 4.88 (1H, septet, J=6.6 Hz), 4.33 (2H, br.), 4.14-3.97 (1H, m), 3.80-3.65 (2H, m), 2.73 (1H, t, J=12.5 Hz), 2.08-1.55 (8H, m), 1.62 (6H, d, J=6.6 Hz), 1.48 (9H, s).

A signal due to OH was not observed.

Step 9. N-[cis-6-(3-hydroxypropyl)piperidin-3-yl]-1-isopropyl-1H-indazole-3-carboxamide ethanedioate The title compound was prepared according to the procedure described in step 4 of Example 4 from tert-butyl cis-2-(3-hydroxypropyl)-5-{[(1-isopropyl-1H-indazol-3-yl)carbonyl]amino}piperidine-1-carboxylate (step 8 of Example 5).

MS (ESI) m/z: 345 (M+H)⁺.

IR (KBr) ν: 3350, 1654, 1599, 1560, 1330, 1205, 750 cm⁻¹ ¹H NMR (DMSO-d₆) δ 8.19-8.17 (2H, m), 7.82 (1H, d, J=8.8 Hz), 7.47-7.42 (1H, m), 7.30-7.25 (1H, m), 5.10 (1H, septet, J=6.6 Hz), 4.23 (1H, br.), 3.44-3.38 (2H, m), 3.18-2.81 (3H, m), 1.96-1.35 (9H, m), 1.55 (6H, d, J=6.6 Hz). A signal due to OH was not observed.

Anal. Calcd. for C₂₀.₅H₂₉.₅N₄O₅·0.75 C₂H₂O₄·1.5 H₂O: C, 56.09; H, 7.46; N, 12.76. Found: C, 56.10; H, 7.61; N, 12.78.

Example 6

N-[Cis-6-(3-Hydroxy-3-Methylbutyl)Piperidin-3-YL]-1-Isopropyl-1H-Indazole-3-Carboxamide Step 1. tert-Butyl cis-2-(3-hydroxy-3-methylbutyl)-5-{[(1-isopropyl-1H-indazol-3-yl)carbonyl]amino}piperidine-1-carboxylate To a stirred solution of tert-butyl cis-2-(3-ethoxy-3-oxopropyl)-5-{[(1-isopropyl-1H-indazol-3-yl) carbonyl]amino}piperidine-1-carboxylate (320 mg, 0.658 mmol, step 7 of example 5) in tetrahydrofuran (14.6 mL) was added methylmagnesium bromide (0.84 M in tetrahydrofuran, 7.8 mL, 6.58 mmol) at 0° C., and the mixture was allowed to warm to room temperature over 4 h. The mixture was quenched with saturated ammonium chloride aqueous solution (15 mL) and diluted with water (15 mL). The aqueous solution was extracted with dichloromethane (30 mL×3). The combined organic layer was dried over magnesium sulfate and concentrated under reduced pressure. The resulting residue was chromatographed on a column of silica gel eluting with n-hexane/ethyl acetate (1:1) to give 297 mg (96%) of the title compound as a colorless oil.

MS (ESI) m/z: 373 (M+H)⁺ (−BOC).

¹H NMR (CDCl₃) δ 8.38 (1H, d, J=8.1 Hz), 7.48-7.38 (2H, m), 7.30-7.25 (1H, m), 6.85 (1H, d, J=8.1 Hz), 4.88 (1H, septet, J=6.6 Hz), 4.31 (2H, br.), 4.13-3.98 (1H, m), 2.71 (1H, t, J=12.5 Hz), 2.09-1.67 (6H, m), 1.62 (6H, d, J=6.6 Hz), 1.55-1.40 (2H, m), 1.48 (9H, s), 1.25 (6H, s). A signal due to OH was not observed.

Step 2. N-[cis-6-(3-Hydroxy-3-methylbutyl)piperidin-3-yl]-1-isopropyl-1H-indazole-3-carboxamide The title compound was prepared according to the procedure described in step 7 of Example 2 from tert-butyl(2S,5S)-2-(3-hydroxy-3-methylbutyl)-5-{[(1-isopropyl-1H-indazol-3-yl)carbonyl]amino}piperidine-1-carboxylate (step 1 of Example 6).

MS (ESI) m/z: 373 (M+H)⁺.

IR (KBr) ν: 3450, 2950, 1650, 1530, 1192, 1058, 888, 806, 601 cm⁻¹

¹H NMR (CDCl₃) δ 8.38 (1H, d, J=7.9 Hz), 7.63 (1H, d, J=7.3 Hz), 7.48-7.36 (2H, m), 7.29-7.23 (1H, m), 4.90 (1H, septet, J=6.6 Hz), 4.29-4.24 (1H, m), 3.21-3.15 (1H, m), 2.95 (1H, dd, J=12.5, 2.6 Hz), 2.69-2.54 (1H, m), 2.44-1.94 (3H, m), 1.83-1.27 (5H, m), 1.64 (6H, d, J=6.6 Hz), 1.24 (6H, s). Signals due to NH, OH were not observed.

Anal. Calcd. for C₂₁H₃₂N₄O₂: C, 67.71; H, 8.66; N, 15.04. Found: C, 67.49; H, 8.79; N, 14.72.

Example 7

N-[(3S,5S)-5-(Hydroxymethyl)Pyrrolidin-3-YL]-1-Isopropyl-1H-Indazole-3-Carboxamide

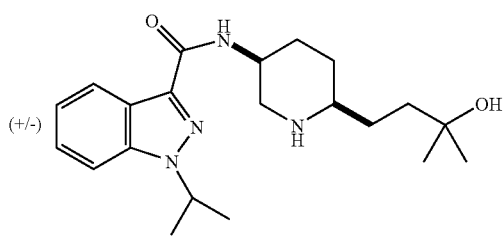

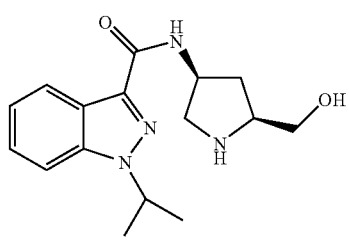

Step 1. 1-tert-Butyl 2-methyl (2S,4S)-4-{[(1-isopropyl-1H-indazol-3-yl)carbonyl]amino}pyrrolidine-1,2-dicarboxylate To a stirred solution of 1-isopropyl-1H-indazole-3-carboxylic acid (300 mg, 1.47 mmol) and 1-tert-butyl 2-methyl (2S,4S)-4-aminopyrrolidine-1,2-dicarboxylate (396 mg, 1.62 mmol, *Bioorg. Med. Chem.*, 2002, 10, 1399-1415) in N,N-dimethylformamide (15 mL) were added diethyl cyanophosphonate (0.27 mL, 1.76 mmol) and N,N-diisopropylethylamine (0.31 mL, 1.76 mmol) at room temperature. The resulting mixture was stirred for 14 h at the same temperature and concentrated under reduced pressure. The resulting residue was diluted with ethyl acetate (200 mL), and the solution was washed with water (50 mL×2), brine (50 mL), dried over sodium sulfate, and concentrated under reduced pressure. The resulting residue was chromatographed on a column of silica gel eluting with n-hexane/ethyl acetate (3:1) to give 618 mg (98%) of the title compound as a white amorphous solid.

MS (ESI) m/z: 331 (M+H)$^+$ (−BOC).

$^1$H NMR (CDCl$_3$) δ 8.35 (1H, d, J=8.3 Hz), 7.74-7.65 (1H, m), 7.48-7.38 (2H, m), 7.30-7.25 (1H, m), 4.95-4.84 (2H, m), 4.48-4.35 (1H, m), 3.90-3.55 (5H, m), 2.70-2.57 (1H, m), 2.21-2.18 (1H, m), 1.65-1.60 (6H, m), 1.48-1.45 (9H, m).

Step 2. tert-Butyl (2S,4S)-2-(hydroxymethyl)-4-{[(1-isopropyl-1H-indazol-3-yl)carbonyl]amino}pyrrolidine-1-carboxylate To a stirred solution of 1-tert-butyl 2-methyl (2S,4S)-4-{[(1-isopropyl-1H-indazol-3-yl)carbonyl]amino}pyrrolidine-1,2-dicarboxylate (135 mg, 0.313 mmol, step 1 of Example 7) in tetrahydrofuran-methanol (2 mL-2 mL) were added lithium chloride (81 mg, 1.92 mmol) and sodium borohydride (73 mg, 1.92 mmol) at room temperature. The resulting mixture was stirred at the same temperature for 20 h. Another lithium chloride (81 mg, 1.92 mmol) and sodium borohydride (73 mg, 1.92 mmol) were added to the mixture at room temperature. After stirring for 3 h, the mixture was quenched with water (10 mL), extracted with ethyl acetate (100 mL). The organic layer was washed with brine (10 mL), dried over sodium sulfate, and concentrated under reduced pressure. The resulting residue was chromatographed on a column of silica gel eluting with n-hexane/ethyl acetate (1:1) to give 117 mg (93%) of the title compound as a colorless oil.

MS (ESI) m/z: 403 (M+H)$^+$, 401 (M−H)$^-$.

$^1$H NMR (CDCl$_3$) δ 8.36 (1H, d, J=8.1 Hz), 7.48-4.25 (4H, m), 4.92-4.83 (1H, m), 4.74-4.62 (1H, m), 4.33-4.25 (1H, m), 2.14-3.91 (4H, m), 3.73-3.65 (1H, m), 3.36-3.28 (1H, m), 2.60-2.51 (1H, m), 1.61-1.59 (6H, m), 1.48 (9H, s).

Step 3. N-[(3S,5S)-5-(Hydroxymethyl)pyrrolidin-3-yl]-1-isopropyl-1H-indazole-3-carboxamide The mixture of tert-butyl (2S,4S)-2-(hydroxymethyl)-4-{[(1-isopropyl-1H-indazol-3-yl)carbonyl]amino}pyrrolidine-1-carboxylate (115 mg, 0.286 mmol, step 2 of Example 7) and 10% hydrochloric acid in methanol (5 mL) was stirred at room temperature for 14 h and concentrated under reduced pressure. The resulting residue was basified with saturated sodium hydrogencarbonate aqueous solution, extracted with dichloromethane (100 mL). The organic layer was separated, dried over sodium sulfate, and concentrated under reduced pressure. The resulting residue was recrystallized from isopropyl ether to give 79 mg (91%) of the title compound as a white crystal.

MS (ESI) m/z: 303 (M+H)$^+$.

IR (KBr) ν: 3347, 2982, 1665, 1539, 1491, 1221, 1199, 1088, 763 cm$^{-1}$ $^1$H NMR (CDCl$_3$) δ 8.37 (1H, d, J=8.1 Hz), 7.47-7.37 (3H, m), 7.29-7.24 (1H, m), 4.91-4.83 (1H, m), 4.69-4.58 (1H, m), 3.70 (1H, dd, J=10.3, 2.9 Hz), 3.57-3.43 (2H, m), 3.32 (1H, dd, J=11.0, 5.9 Hz), 2.99 (1H, dd, J=11.0, 4.4 Hz), 2.40 (1H, dt, J=13.2, 8.2 Hz), 1.89-1.59 (7H, m). Signals due to NH and OH were not observed.

Anal. Calcd. for C$_{16}$H$_{22}$N$_4$O$_2$·0.05 C$_6$H$_{14}$O·0.2 H$_2$O: C, 62.93; H, 7.48; N, 18.01. Found: C, 62.68; H, 7.38; N, 17.65.

[α]$_D^{22}$=+28.1° (C=0.25, Methanol).

Example 8

N-[(3S,5R)-5-(3-Hydroxypropyl)Pyrrolidin-3-Yl]-1-Isopropyl-1H-Indazole-3-Carboxamide and its Ethanedioate

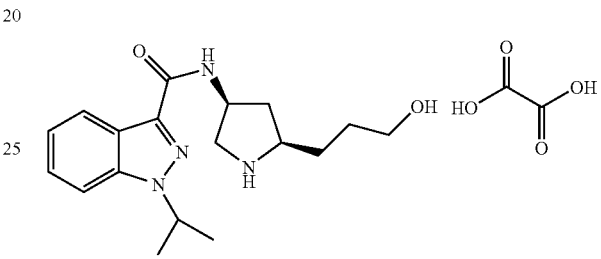

Step 1. tert-Butyl (2R,4R)-4-{[tert-butyl(dimethyl)silyl]oxy}-2-(3-ethoxy-3-oxopropyl)pyrrolidine-1-carboxylate To a stirred solution of tert-butyl (2S,4R)-4-{[tert-butyl(dimethyl)silyl]oxy}-2-[(1E)-3-ethoxy-3-oxoprop-1-en-1-yl]pyrrolidine-1-carboxylate (1.37 g, 3.4 mmol, *J. Antibiotics*, 1997, 50, 567-585) in ethanol (30 mL) was added 10 wt. % palladium on carbon (140 mg). The resulting mixture was stirred under hydrogen (4 atom) at room temperature for 3 h. The mixture was filtered through a pad of Celite and the filter cake was washed with ethanol. The combined filtrate was concentrated to give 1.34 g (97%) of the title compound as a colorless oil.

MS (ESI) m/z: 302 (M+H)$^+$ (−BOC).

$^1$H NMR (CDCl$_3$) δ 4.36-4.30 (1H, m), 4.12 (2H, q, J=6.9 Hz), 3.94 (1H, br s), 3.54-3.30 (2H, m), 2.28 (2H, br s), 2.12-1.92 (2H, m), 1.80-1.65 (2H, m), 1.46 (9H, s), 1.25 (3H, t, J=7.3 Hz), 0.86 (9H, s), 0.05 (6H, s).

Step 2. tert-Butyl (2R,4R)-2-(3-ethoxy-3-oxopropyl)-4-hydroxypyrrolidine-1-carboxylate To a stirred solution of tert-butyl (2R,4R)-4-{[tert-butyl(dimethyl)silyl]oxy}-2-(3-ethoxy-3-oxopropyl)pyrrolidine-1-carboxylate (500 mg, 1.2 mmol, step 1 of Example 8) in tetrahydrofuran (5 mL) was added tetrabutylammonium fluoride solution (1.0 M in tetrahydrofuran, 1.36 mL, 1.4 mmol) at 0° C. The resulting mixture was allowed to warm to room temperature and stirred for 6 h. The mixture was diluted with ethyl acetate (100 mL), washed with water (20 mL), brine (20 mL). The organic layer was separated, dried over sodium sulfate, and concentrated under reduced pressure. The resulting residue was chromatographed on a column of silica gel eluting with n-hexane/ethyl acetate (2:1) to give 338 mg (95%) of the title compound as a colorless oil.

MS (ESI) m/z: 188 (M+H)⁺ (−BOC).
¹H NMR (CDCL₃) δ 4.45-3.38 (1H, m), 4.12 (2H, q, J=7.3 Hz), 4.03-3.94 (1H, m), 3.66-3.36 (2H, m), 2.32-2.25 (2H, m), 2.19-2.01 (2H, m), 1.82-1.71 (3H, m), 1.47 (9H, s), 1.26 (3H, t, J=7.3 Hz).

Step 3. tert-Butyl (2R,4R)-2-(3-ethoxy-3-oxopropyl)-4-[(methylsulfonyl)oxy]pyrrolidine-1-carboxylate To a stirred mixture of tert-butyl (2R,4R)-2-(3-ethoxy-3-oxopropyl)-4-hydroxypyrrolidine-1-carboxylate (335 mg, 1.2 mmol, step 2 of Example 8) and triethylamine (0.25 mL, 1.8 mmol) in dichloromethane (5 mL) at 0° C. was added methanesulfonyl chloride (0.14 mL, 1.8 mmol). The resulting mixture was allowed to warm to room temperature and stirred for 3 h. To the mixture was added water (10 mL) and extracted with dichloromethane (100 mL). The organic layer was dried over sodium sulfate, and concentrated under reduced pressure to give 462 mg (100%) of the title compound as a yellow oil, which was used for the next step without further purification.
¹H NMR (CDCl₃) δ 5.27-5.16 (1H, m), 4.23-4.84 (4H, m), 3.58-3.42 (1H, m), 3.04 (3H, s), 2.51-1.75 (4H, m), 1.48 (9H, s), 1.26 (3H, t, J=6.6 Hz).

Step 4. tert-Butyl (2R,4S)-4-azido-2-(3-ethoxy-3-oxopropyl)pyrrolidine-1-carboxylate The mixture of tert-butyl (2R,4R)-2-(3-ethoxy-3-oxopropyl)-4-[(methylsulfonyl)oxy]pyrrolidine-1-carboxylate (462 mg, 1.20 mmol, step 3 of Example 8) and sodium azide (228 mg, 3.5 mmol) in N,N-dimethylformamide (10 mL) was stirred at 80° C. for 14 h. After cooling to room temperature, the mixture was diluted with ethyl acetate (150 mL), washed with water (50 mL×2) and brine (50 mL). The organic layer was separated, dried over sodium sulfate, and concentrated under reduced pressure to give 562 mg (100%) of the title compound as a colorless oil, which was used for the next step without further purification.
¹H NMR (CDCl₃) δ 4.17-4.09 (2H, m), 3.95-3.68 (2H, m), 3.26 (1H, dd, J=11.7, 4.4 Hz), 2.37-2.23 (4H, m), 1.91-1.73 (3H, m), 1.47 (9H, s), 1.26 (3H, t, J=7.0 Hz).

Step 5. tert-Butyl (2R,4S)-4-amino-2-(3-ethoxy-3-oxopropyl)pyrrolidine-1-carboxylate To a stirred solution of tert-butyl (2R,4S)-4-azido-2-(3-ethoxy-3-oxopropyl)pyrrolidine-1-carboxylate (562 mg, 1.20 mmol, step 4 of Example 8) in ethanol (10 mL) was added 10 wt. % palladium on carbon (50 mg). The resulting mixture was stirred under hydrogen (4 atom) at room temperature for 3 h. The mixture was filtered through a pad of Celite and the filter cake was washed with ethanol. The combined filtrate was concentrated to give 352 mg (97%) of the title compound as a colorless oil.
¹H NMR (CDCl₃) δ 4.12 (2H, q, J=7.3 Hz), 3.81 (2H, br s), 3.48-3.38 (1H, m), 2.89-2.87 (1H, m), 2.37-2.15 (4H, m), 1.91-1.80 (1H, m), 1.67-1.34 (10H, m), 1.26 (3H, t, J=7.0 Hz). Signals due to NH₂ were not observed.

Step 6. tert-Butyl (2R,4S)-2-(3-ethoxy-3-oxopropyl)-4-{[(1-isopropyl-1H-indazol-3-yl)carbonyl]amino}pyrrolidine-1-carboxylate The title compound was prepared according to the procedure described in step 1 of Example 7 from tert-butyl (2R,4S)-4-amino-2-(3-ethoxy-3-oxopropyl)pyrrolidine-1-carboxylate (step 5 of Example 8).
MS (ESI) m/z: 373 (M+H)⁺ (−BOC).
¹H NMR (CDCl₃) δ 8.36 (1H, d, J=8.1 Hz), 7.48-7.39 (2H, m), 7.31-7.26 (1H, m), 7.20 (1H, br s), 4.93-4.84 (1H, m), 4.64-4.56 (1H, m), 4.17-4.05 (3H, m), 3.93 (1H, br s), 3.21 (1H, dd, J=11.0, 7.3 Hz), 2.59-2.50 (1H, m), 2.42-2.29 (3H, m), 1.95-1.68 (2H, m), 1.66-1.60 (6H, m), 1.48 (9H, s), 1.25 (3H, t, J=7.3 Hz).

Step 7. tert-Butyl (2R,4S)-2-(3-hydroxypropyl)-4-{[(1-isopropyl-1H-indazol-3-yl)carbonyl]amino}pyrrolidine-1-carboxylate The title compound was prepared according to the procedure described in step 2 of Example 7 from tert-butyl (2R,4S)-2-(3-ethoxy-3-oxopropyl)-4-{[(1-isopropyl-1H-indazol-3-yl)carbonyl]amino}pyrrolidine-1-carboxylate (step 6 of Example 8).
MS (ESI) m/z: 331 (M+H)⁺ (−BOC).
¹H NMR (CDCl₃) δ 8.36 (1H, d, J=8.1 Hz), 7.48-7.38 (2H, m), 7.31-7.26 (1H, m), 7.11 (1H, d, J=7.3 Hz), 4.93-4.84 (1H, m), 4.66-4.54 (1H, m), 4.09-4.03 (1H, m), 3.93 (1H, br s), 3.69 (2H, br s), 3.22 (1H, dd, J=11.0, 7.3 Hz), 2.60-2.51 (1H, m), 2.21-2.00 (1H, m), 1.84-1.66 (4H, m), 1.61 (6H, d, J=6.6 Hz), 1.47 (9H, s). A signal due to OH was not observed.

Step 8. N-[(3S,5R)-5-(3-Hydroxypropyl)pyrrolidin-3-yl]-1-isopropyl-1H-indazole-3-carboxamide The title compound was prepared according to the procedure described in step 3 of Example 7 from tert-butyl (2R,4S)-2-(3-hydroxypropyl)-4-{[(1-isopropyl-1H-indazol-3-yl)carbonyl]amino}pyrrolidine-1-carboxylate (step 7 of Example 8).
MS (ESI) m/z: 331 (M+H)⁺.
¹H NMR (CDCl₃) δ 8.37 (1H, d, J=8.1 Hz), 7.47-7.37 (2H, m), 7.29-7.23 (2H, m), 4.92-4.83 (1H, m), 4.66-4.55 (1H, m), 3.65 (2H, t, J=4.8 Hz), 3.33 (1H, dd, J=11.7, 7.3 Hz), 3.24-3.16 (1H, m), 3.00 (1H, dd, J=11.7, 5.1 Hz), 2.52-2.43 (1H, m), 1.86-1.63 (4H, m), 1.61 (6H, d, J=6.6 Hz), 1.54-1.44 (1H, m).
Signals due to NH and OH were not observed.

Step 9. N-[(3S,5R)-5-(3-Hydroxypropyl)pyrrolidin-3-yl]-1-isopropyl-1H-indazole-3-carboxamide ethanedioate A mixture of N-[(3S,5R)-5-(3-hydroxypropyl)pyrrolidin-3-yl]-1-isopropyl-1H-indazole-3-carboxamide (39 mg, 0.12 mmol, step 8 of Example 8) and oxalic acid (11 mg, 0.12 mmol) in dichloromethane-methanol (5 mL-1 mL) was stirred for 1 h. The mixture was concentrated to give 40 mg (81%) of the title compound as a white amorphous solid.
MS (ESI) m/z: 331 (M+H)⁺.
IR (KBr) ν: 1647, 1540, 1491, 1201, 722 cm⁻¹
¹H NMR (DMSO-d₆) δ 8.50 (1H, d, J=8.1 Hz), 8.17 (1H, d, J=8.1 Hz), 7.82 (1H, d, J=8.1 Hz), 7.48-7.43 (1H, m), 7.30-7.25 (1H, m), 5.15-5.56 (1H, m), 4.71-4.63 (1H, m), 3.50-3.40 (2H, m), 3.24-3.17 (2H, m), 2.53-2.44 (2H, m), 1.80-1.67 (3H, m), 1.56-1.46 (8H, m). Signals due to NH and OH were not observed.
Anal. Calcd. for $C_{18}H_{26}N_4O_2 \cdot C_2H_2O_4 \cdot 0.1 H_2O$: C, 56.89; H, 6.73; N, 13.27. Found: C, 56.67; H, 6.99; N, 13.12.
$[\alpha]_D^{22}$=+7.2° (C=0.25, Methanol).

Example 9

N-[(3S,5S)-5-(2-Hydroxyethyl)Pyrrolidin-3-Yl]-1-Isopropyl-1H-Indazole-3-Carboxamide and its Ethanedioate

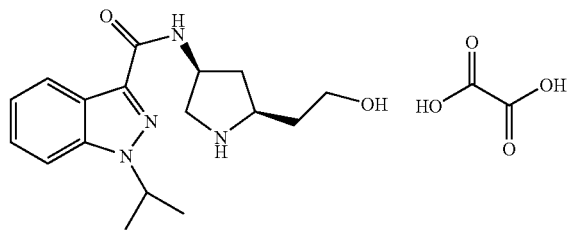

Step 1. tert-Butyl (2R,4R)-4-{[tert-butyl(dimethyl)silyl]oxy}-2-(cyanomethyl)pyrrolidine-1-carboxylate The mixture of tert-butyl (2S,4R)-4-{[tert-butyl(dimethyl)silyl]oxy}-2-{[(methylsulfonyl)oxy]methyl}pyrrolidine-1-carboxylate (13.95 g, 32.6 mmol, *J. Med. Chem.* 1988, 31, 1598-611) and sodium cyanide (3.20 g, 65.2 mmol) in dimethylsulfoxide (100 mL) was stirred at 80° C. for 20 h. After cooling to room temperature, water (200 mL) was added to the mixture. The resulting mixture was extracted with ethyl acetate (400 mL×2). The combined organic layer was washed with water (200 mL), brine (200 mL), dried over sodium sulfate, and concentrated under reduced pressure. The resulting residue was chromatographed on a column of silica gel eluting with n-hexane/ethyl acetate (5:1) to give 7.81 g (70%) of the title compound as a colorless oil.

$^1$H NMR (CDCl$_3$) δ 4.41 (1H, br s), 4.21-4.05 (1H, m), 3.61-3.40 (2H, m), 3.15-3.05 (1H, m), 2.78-2.65 (1H, m), 2.23-1.92 (2H, m), 1.47 (9H, s), 0.86 (9H, s), 0.07 (6H, s).

Step 2. tert-Butyl (2S,4R)-4-hydroxy-2-(2-methoxy-2-oxoethyl)pyrrolidine-1-carboxylate The solution of tert-butyl (2R,4R)-4-{[tert-butyl(dimethyl)silyl]oxy}-2-(cyanomethyl)pyrrolidine-1-carboxylate (7.81 g, 22.9 mmol, step 1 of Example 9) in concentrated hydrochloric acid-acetic acid (50 mL-50 mL) was refluxed for 15 h and concentrated under reduced pressure. The resulting residue was dissolved in 10% hydrochloric acid in methanol (50 mL). The mixture was refluxed for 18 h and concentrated under reduced pressure. To the suspension of resulting residue in dichloromethane (100 mL) were added triethylamine (9.58 mL, 68.7 mmol) and di-tert-butyl dicarbonate (7.50 g, 34.4 mmol) at 0° C. The mixture was allowed to warm to room temperature and stirred for 14 h. To the mixture was added water (100 mL). The organic layer was separated, dried over sodium sulfate, and concentrated under reduced pressure. The resulting residue was chromatographed on a column of silica gel eluting with n-hexane/ethyl acetate (1:1) to give 4.23 g (71%) of the title compound as a colorless oil.

MS (ESI) m/z: 160 (M+H)$^+$ (−BOC).

$^1$H NMR (CDCl$_3$) δ 4.49-4.37 (1H, m), 4.33-4.21 (1H, m), 3.67 (3H, s), 3.61-3.41 (2H, m), 3.13-2.86 (1H, m), 2.48-2.40 (1H, m), 2.29-2.16 (1H, m), 2.08-1.89 (1H, m), 1.47 (9H, s). A signal due to OH was not observed.

Step 3. tert-Butyl (2S,4S)-4-azido-2-(2-methoxy-2-oxoethyl)pyrrolidine-1-carboxylate To a stirred mixture of tert-butyl (2S,4R)-4-hydroxy-2-(2-methoxy-2-oxoethyl)pyrrolidine-1-carboxylate (3.00 g, 11.6 mmol, step 2 of Example 9) in tetrahydrofuran (50 mL) were added triphenylphosphine (4.55 g, 17.4 mmol) and diethyl azodicarboxylate solution (50% in toluene, 7.56 mL, 17.36 mmol) at room temperature. After stirring for 15 min, diphenyl phosphoryl azide (3.74 mL, 17.36 mmol) was added to the mixture. The resulting mixture was stirred at room temperature for 40 h and concentrated under reduced pressure. The resulting residue was chromatographed on a column of silica gel eluting with n-hexane/ethyl acetate (4:1) to give 2.53 g (77%) of the title compound as a pale yellow oil.

$^1$H NMR (CDCl$_3$) δ 4.28-4.11 (2H, m), 3.78-3.58 (4H, m), 3.46-3.34 (1H, m), 3.17-2.87 (1H, m), 2.72-2.54 (1H, m), 2.40-2.30 (1H, m), 2.01-1.92 (1H, m), 1.47 (9H, s).

Step 4. tert-Butyl (2S,4S)-4-amino-2-(2-methoxy-2-oxoethyl)pyrrolidine-1-carboxylate The title compound was prepared according to the procedure described in step 5 of Example 8 from tert-butyl (2S,4S)-4-azido-2-(2-methoxy-2-oxoethyl)pyrrolidine-1-carboxylate (step 3 of Example 9).

$^1$H NMR (CDCl$_3$) δ 4.19-4.04 (1H, m), 3.68 (3H, s), 3.56-3.46 (1H, m), 3.23-2.94 (2H, m), 2.74-2.58 (1H, m), 2.45-2.36 (1H, m), 1.46 (9H, s), 1.29-1.18 (2H, m). Signals due to NH$_2$ were not observed.

Step 5. tert-Butyl (2S,4S)-4-{[(1-isopropyl-1H-indazol-3-yl)carbonyl]amino}-2-(2-methoxy-2-oxoethyl)pyrrolidine-1-carboxylate The title compound was prepared according to the procedure described in step 1 of Example 7 from tert-butyl (2S,4S)-4-amino-2-(2-methoxy-2-oxoethyl)pyrrolidine-1-carboxylate (step 4 of Example 9).

MS (ESI) m/z: 345 (M+H)$^+$ (−BOC).

$^1$H NMR (CDCl$_3$) δ 8.36 (1H, d, J=8.1 Hz), 7.48-7.39 (2H, m), 7.31-7.25 (1H, m), 7.13 (1H, d, J=5.9 Hz), 4.93-4.84 (1H, m), 4.68-4.56 (1H, m), 4.29-4.02 (2H, m), 3.68 (3H, s), 3.34-2.96 (2H, m), 2.72-2.58 (2H, m), 2.03-1.87 (1H, m), 1.62 (6H, d, J=6.6 Hz), 1.48 (9H, s).

Step 6. tert-Butyl (2S,4S)-2-(2-hydroxyethyl)-4-{[(1-isopropyl-1H-indazol-3-yl)carbonyl]amino}pyrrolidine-1-carboxylate To a solution of tert-butyl (2S,4S)-4-{[(1-isopropyl-1H-indazol-3-yl)carbonyl]amino}-2-(2-methoxy-2-oxoethyl)pyrrolidine-1-carboxylate (200 mg, 0.45 mmol, step 5 of Example 9) in tetrahydrofuran (5 mL) was added lithium borohydride solution (2 M in tetrahydrofuran, 1.13 mL, 2.25 mmol) at room temperature. The mixture was stirred at room temperature for 20 h. To the resulting mixture water (10 mL) was added. The mixture was extracted with ethyl acetate (100 mL). The organic layer was washed with brine (10 mL). The organic layer was separated, dried over sodium sulfate, and concentrated under reduced pressure. The resulting residue was chromatographed on a column of silica gel eluting with n-hexane/ethyl acetate (1:1) to give 182 mg (97%) of the title compound as a white amorphous solid.

MS (ESI) m/z: 317 (M+H)$^+$ (−BOC), 415 (M−H)$^-$.

$^1$H NMR (CDCl$_3$) δ 8.36 (1H, d, J=8.1 Hz), 7.49-7.39 (2H, m), 7.30 (1H, d, J=8.1 Hz), 7.16 (1H, d, J=7.3 Hz), 4.93-4.84

(1H, m), 4.66-4.55 (1H, m), 4.30-4.19 (1H, m), 4.16-4.00 (2H, m), 3.74-3.62 (2H, m), 3.28 (1H, dd, J=11.7, 5.9 Hz), 2.63 (1H, dt, J=13.2, 8.1 Hz), 1.96-1.74 (2H, m), 1.61 (6H, d, J=6.6 Hz), 1.48 (9H, s). A signal due to O$\underline{H}$ was not observed.

Step 7. N-[(3S,5S)-5-(2-hydroxyethyl)pyrrolidin-3-yl]-1-isopropyl-1H-indazole-3-carboxamide The title compound was prepared according to the procedure described in step 3 of Example 7 from tert-butyl (2S, 4S)-2-(2-hydroxyethyl)-4-{[(1-isopropyl-1H-indazol-3-yl)carbonyl]amino}pyrrolidine-1-carboxylate (step 6 of Example 9).

MS (ESI) m/z: 317 (M+H)$^+$.

$^1$H NMR (CDCl$_3$) δ 8.37 (1H, d, J=8.1 Hz), 7.48-7.38 (2H, m), 7.30-7.20 (2H, m), 4.95-4.81 (1H, m), 4.66-4.54 (1H, m), 3.93-3.78 (2H, m), 3.53-3.17 (3H, m), 2.94 (1H, dd, J=11.7, 5.9 Hz), 2.51 (1H, dt, J=13.2, 7.7 Hz), 1.91-1.69 (3H, m), 1.61 (6H, d, J=6.6 Hz), 1.60-1.49 (1H, m).

Step 8. N-[(3S,5S)-5-(2-Hydroxyethyl)pyrrolidin-3-yl]-1-isopropyl-1H-indazole-3-carboxamide ethanedioate The title compound was prepared according to the procedure described in step 9 of Example 8 from N-[(3S,5S)-5-(2-hydroxyethyl)pyrrolidin-3-yl]-1-isopropyl-1H-indazole-3-carboxamide (step 7 of Example 9).

MS (ESI) m/z: 317 (M+H)$^+$.

IR (KBr) ν: 1636, 1539, 1490, 1392, 1280, 1201, 752, 721 cm$^{-1}$ $^1$H NMR (DMSO-d$_6$) δ 8.58 (1H, d, J=7.3 Hz), 8.12 (1H, d, J=8.1 Hz), 7.82 (1H, d, J=8.1 Hz), 7.46 (1H, t, J=7.7 Hz), 7.28 (1H, t, J=7.7 Hz), 5.16-5.03 (1H, m), 4.77-4.65 (1H, m), 3.68-3.45 (4H, m), 3.27 (1H, dd, J=11.7, 5.9 Hz), 2.57-2.48 (1H, m), 2.02-1.79 (3H, m), 1.55 (6H, d, J=6.6 Hz). Signals due to NH and OH were not observed.

Anal. Calcd. for C$_{17}$H$_{24}$N$_4$O$_2$.C$_2$H$_2$O$_4$.0.5 H$_2$O: C, 54.93; H, 6.55; N, 13.49. Found: C, 54.56; H, 6.61; N, 13.26.

[α]$_D^{22}$=−3.7° (C=0.26, Methanol).

Example 10

N-[(3S,5S)-5-(2-Hydroxy-2-Methylpropyl)Pyrrolidin-3-Yl]-1-Isopropyl-1H-Indazole-3-Carboxamide and its Ethanedioate

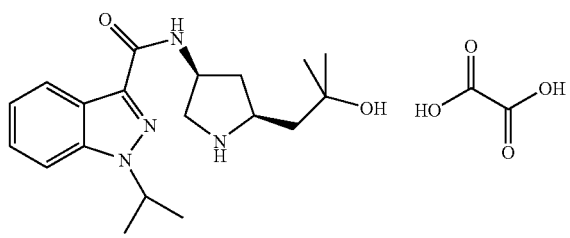

Step 1. tert-Butyl (2S,4S)-2-(2-hydroxy-2-methylpropyl)-4-{[(1-isopropyl-1H-indazol-3-yl)carbonyl]amino}pyrrolidine-1-carboxylate To a stirred solution of tert-butyl (2S,4S)-4-{[(1-isopropyl-1H-indazol-3-yl)carbonyl]amino}-2-(2-methoxy-2-oxoethyl)pyrrolidine-1-carboxylate (200 mg, 0.45 mmol, step 5 of Example 9) in tetrahydrofuran (10 mL) was added methylmagnesium bromide solution (0.84 M in tetrahydrofuran, 5.4 mL, 4.5 mmol) at 0° C. The resulting mixture was allowed to warm to room temperature and stirred for 2 h. To the resulting residue were added saturated ammonium chloride aqueous solution (10 mL) and water (10 mL). The mixture was extracted with dichloromethane (50 mL×2). The combined organic layer was dried over sodium sulfate, and concentrated under reduced pressure. The resulting residue was chromatographed on a column of silica gel eluting with n-hexane/ethyl acetate (1:1) to give 177 mg (88%) of the title compound as a colorless oil.

MS (ESI) m/z: 345 (M+H)$^+$ (−BOC).

$^1$H NMR (CDCl$_3$) δ 8.37 (1H, d, J=8.1 Hz), 7.48-7.39 (2H, m), 7.31-7.26 (2H, m), 4.93-4.84 (1H, m), 4.66-4.55 (1H, m), 4.27-4.17 (1H, m), 4.01 (1H, dd, J=11.4, 7.0 Hz), 3.91 (1H, br s), 3.32 (1H, dd, J=11.7, 5.1 Hz), 2.64-2.54 (1H, m), 2.19 (1H, dd, J=14.3, 5.5 Hz), 1.73 (1H, dd, J=14.3, 6.2 Hz), 1.62-1.59 (6H, m), 1.47 (9H, s), 1.29-1.26 (6H, m). A signal due to O$\underline{H}$ was not observed.

Step 2. N-[(3S,5S)-5-(2-Hydroxy-2-methylpropyl)pyrrolidin-3-yl]-1-isopropyl-1H-indazole-3-carboxamide The title compound was prepared according to the procedure described in step 3 of Example 7 from tert-butyl (2S, 4S)-2-(2-hydroxy-2-methylpropyl)-4-{[(1-isopropyl-1H-indazol-3-yl)carbonyl]amino}pyrrolidine-1-carboxylate (step 1 of Example 10).

MS (ESI) m/z: 345 (M+H)$^+$.

$^1$H NMR (CDCl$_3$) δ 8.37 (1H, d, J=8.1 Hz), 7.48-7.37 (2H, m), 7.30-7.25 (1H, m), 7.12 (1H, d, J=7.3 Hz), 4.93-4.84 (1H, m), 4.60-4.46 (1H, m), 3.68-3.59 (1H, m), 3.42 (1H, dd, J=12.5, 7.3 Hz), 2.91 (1H, dd, J=12.1, 7.0 Hz), 2.59 (1H, dt, J=13.2, 8.1 Hz), 1.81-1.73 (1H, m), 1.66 (1H, d, J=3.7 Hz), 1.62 (6H, d, J=6.6 Hz), 1.51-1.42 (1H, m), 1.29 (3H, s), 1.24 (3H, s). Signals due to N$\underline{H}$ and O$\underline{H}$ were not observed.

Step 3. N-[(3S,5S)-5-(2-Hydroxy-2-methylpropyl)pyrrolidin-3-yl]-1-isopropyl-1H-indazole-3-carboxamide ethanedioate The title compound was prepared according to the procedure described in step 9 of Example 8 from N-[(3S,5S)-5-(2-hydroxy-2-methylpropyl)pyrrolidin-3-yl]-1-isopropyl-1H-indazole-3-carboxamide (step 2 of Example 10).

MS (ESI) m/z: 345 (M+H)$^+$.

IR (KBr) ν: 2977, 2936, 1648, 1540, 1491, 1406, 1391, 1369, 1281, 1198, 721 cm$^{-1}$ $^1$H NMR (DMSO-d$_6$) δ 8.54 (1H, d, J=7.3 Hz), 8.17 (1H, d, J=8.1 Hz), 7.82 (1H, d, J=8.1 Hz), 7.45 (1H, t, J=7.7 Hz), 7.28 (1H, t, J=7.3 Hz), 5.15-5.04 (1H, m), 4.69-4.59 (1H, m), 3.67-3.66 (1H, m), 3.49-3.42 (1H, m), 3.23 (1H, dd, J=11.7, 6.6 Hz), 2.56-2.48 (1H, m), 1.95-1.76 (3H, m), 1.55 (6H, d, J=6.6 Hz), 1.20 (6H, s). Signals due to N$\underline{H}$ and O$\underline{H}$ were not observed.

Anal. Calcd. for C$_{19}$H$_{28}$N$_4$O$_2$.C$_2$H$_2$O$_4$.0.2 H$_2$O: C, 57.57; H, 6.99; N, 12.79. Found: C, 57.22; H, 6.92; N, 12.44.

[α]$_D^{22}$=+1.8° (C=0.25, Methanol).

Example 11

5-Fluoro-N-[(3S,5S)-5-(2-Hydroxy-2-Methylpropyl)Pyrrolidin-3-YL]-1-Isopropyl-1H-Indazole-3-Carboxamide and its Ethanedioate

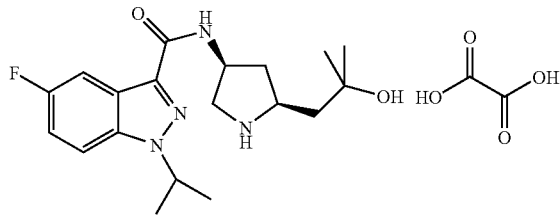

Step 1. Ethyl 5-fluoro-1-isopropyl-1H-indazole-3-carboxylate

To a stirred solution of ethyl 5-fluoro-1H-indazole-3-carboxylate (487 mg, 2.3 mmol, *J. Heterocycl. Chem.* 1964, 1, 239-241) in tetrahydrofuran (4 mL) was added potassium tert-butoxide (289 mg, 2.57 mmol) at 0° C. After stirring at 0° C. for 1 h, 2-iodopropane (438 mg, 2.57 mmol) was added to the mixture. The resulting mixture was stirred at room temperature for 20 h and concentrated under reduced pressure. The mixture was diluted with ethyl acetate (50 mL), washed with water (30 mL) and brine (30 mL). The organic layer was separated, dried over magnesium sulfate, and concentrated under reduced pressure. The resulting residue was chromatographed on a column of silica gel eluting with n-hexane/ethyl acetate (10:1 to 2:1) to give 205 mg (35%) of the title compound as a yellow crystal.

$^1$H NMR (CDCl$_3$) δ 7.84 (1H, dd, J=8.6, 2.6 Hz), 7.48 (1H, dd, J=8.9, 4.3 Hz), 7.20 (1H, dt, J=8.9, 2.6 Hz), 4.94 (1H, septet, J=6.6 Hz), 4.52 (2H, q, J=7.3 Hz), 1.66 (6H, d, J=7.3 Hz), 1.48 (3H, t, J=7.3 Hz).

Step 2. 5-Fluoro-1-isopropyl-1H-indazole-3-carboxylic acid

To a stirred solution of ethyl 5-fluoro-1-isopropyl-1H-indazole-3-carboxylate (125 mg, 0.5 mmol, step 1 of Example 11) in tetrahydrofuran (8 mL) was added 1N aqueous sodium hydroxide solution (1.0 mL, 1.0 mmol) at room temperature. The resulting mixture was stirred at 60° C. for 20 h. The mixture was acidified with 2 N hydrochloric acid (1 mL) and extracted with ethyl acetate (50 mL×3). The combined organic layer was dried over sodium sulfate, and concentrated under reduced pressure to give 106 mg (95%) of the title compound as a white amorphous solid.

MS (ESI) m/z: 223 (M+H)$^+$.

$^1$H NMR (CDCl$_3$) δ 11.31 (1H, br s), 7.88 (1H, dd, J=9.2, 2.6 Hz), 7.51 (1H, dd, J=8.6, 4.6 Hz), 7.23 (1H, dt, J=9.2, 2.6 Hz), 5.06-4.85 (1H, m), 1.68 (6H, d, J=6.6 Hz).

Step 3. tert-Butyl (2S,4S)-4-{[(5-fluoro-1-isopropyl-1H-indazol-3-yl)carbonyl]amino}-2-(2-methoxy-2-oxoethyl)pyrrolidine-1-carboxylate The title compound was prepared according to the procedure described in step 1 of Example 7 from 5-fluoro-1-isopropyl-1H-indazole-3-carboxylic acid (step 2 of Example 11) and tert-butyl (2S,4S)-4-amino-2-(2-methoxy-2-oxoethyl)pyrrolidine-1-carboxylate (step 4 of Example 9).

MS (ESI) m/z: 363 (M+H)$^+$ (−BOC).

$^1$H NMR (CDCl$_3$) δ 7.99 (1H, dd, J=8.4, 2.6 Hz), 7.41 (1H, dd, J=9.2, 4.0 Hz), 7.19 (1H, dt, J=8.8, 2.2 Hz), 7.09 (1H, d, J=6.6 Hz), 4.89-4.81 (1H, m), 4.67-4.57 (1H, m), 4.27-4.01 (2H, m), 3.68 (3H, s), 3.31-2.99 (2H, m), 2.71-2.58 (2H, m), 2.01-1.88 (1H, m), 1.61 (6H, d, J=6.6 Hz), 1.48 (9H, s).

Step 4. tert-Butyl (2S,4S)-4-{[(5-fluoro-1-isopropyl-1H-indazol-3-yl)carbonyl]amino}-2-(2-hydroxy-2-methylpropyl)pyrrolidine-1-carboxylate The title compound was prepared according to the procedure described in step 1 of Example 10 from tert-butyl (2S,4S)-4-{[(5-fluoro-1-isopropyl-1H-indazol-3-yl)carbonyl]amino}-2-(2-methoxy-2-oxoethyl)pyrrolidine-1-carboxylate (step 3 of Example 11).

MS (ESI) m/z: 362 (M+H)$^+$ (−BOC), 461 (M−H)$^−$.

$^1$H NMR (CDCl$_3$) δ 8.00 (1H, dd, J=9.2, 1.8 Hz), 7.41 (1H, dd, J=8.8, 3.7 Hz), 7.31-7.16 (2H, m), 4.89-4.80 (1H, m), 4.65-4.54 (1H, m), 4.28-4.14 (1H, m), 4.00 (1H, dd, J=11.4, 7.0 Hz), 3.90-3.79 (1H, m), 3.31 (1H, dd, J=11.7, 5.9 Hz), 2.63-2.54 (1H, m), 2.19 (1H, dd, J=14.3, 5.5 Hz), 2.01-1.88 (1H, m), 1.73 (1H, dd, J=14.7, 6.6 Hz), 1.61-1.59 (6H, m), 1.48 (9H, m), 1.29 (3H, s), 1.27 (3H, s).

Step 5. 5-Fluoro-N-[(3S,5S)-5-(2-hydroxy-2-methylpropyl)pyrrolidin-3-yl]-1-isopropyl-1H-indazole-3-carboxamide The title compound was prepared according to the procedure described in step 3 of Example 7 from tert-butyl (2S,4S)-4-{[(5-fluoro-1-isopropyl-1H-indazol-3-yl)carbonyl]amino}-2-(2-hydroxy-2-methyl propyl)pyrrolidine-1-carboxylate (step 4 of Example 11).

MS (ESI) m/z: 363 (M+H)$^+$.

$^1$H NMR (CDCl$_3$) δ 8.00 (1H, dd, J=8.4, 2.6 Hz), 7.41 (1H, dd, J=9.2, 4.0 Hz), 7.18 (1H, dt, J=8.8, 2.2 Hz), 7.03 (1H, d, J=7.3 Hz), 4.93-4.80 (1H, m), 4.57-4.46 (1H, m), 3.67-3.56 (1H, m), 3.39 (1H, dd, J=12.1, 7.0 Hz), 2.85 (1H, dd, J=12.5, 7.3 Hz), 2.63-2.53 (1H, m), 1.76-1.64 (1H, m), 1.61 (6H, d, J=6.6 Hz), 1.46-1.37 (2H, m), 1.28 (3H, s), 1.24 (3H, s). Signals due to NH and OH were not observed.

Step 6. 5-Fluoro-N-[(3S,5S)-5-(2-hydroxy-2-methylpropyl)pyrrolidin-3-yl]-1-isopropyl-1H-indazole-3-carboxamide ethanedioate The title compound was prepared according to the procedure described in step 9 of Example 8 from 5-fluoro-N-[(3S,5S)-5-(2-hydroxy-2-methylpropyl)pyrrolidin-3-yl]-1-isopropyl-1H-indazole-3-carboxamide (step 5 of Example 11).

MS (ESI) m/z: 363 (M+H)$^+$.

IR (KBr) ν: 2975, 1648, 1543, 1495, 1410, 1258, 1197, 809 cm$^{-1}$ $^1$H NMR (DMSO-d$_6$) δ 8.48 (1H, d, J=7.3 Hz), 7.90 (1H, dd, J=9.2, 4.0 Hz), 7.80 (1H, dd, J=9.2, 2.6 Hz), 7.38 (1H, dt, J=9.2, 2.2 Hz), 5.16-5.07 (1H, m), 4.84-4.51 (1H, m), 3.68-3.57 (1H, m), 3.35 (1H, dd, J=11.0, 8.1 Hz), 3.11 (1H, dd, J=11.7, 6.6 Hz), 2.51-2.44 (1H, m), 1.88-1.66 (3H, m), 1.54 (6H, d, J=6.6 Hz), 1.18 (6H, s). Signals due to NH and OH were not observed.

Anal. Calcd. for C$_{19}$H$_{27}$N$_4$O$_2$F—C$_2$H$_2$O$_4$: C, 55.74; H, 6.46; N, 12.38. Found: C, 56.08; H, 6.78; N, 12.37.

[α]$_D^{22}$=+7.8° (C=0.25, Methanol).

Example 12

N-{(3S,5S)-5-[(2-Hydroxy-2-Methylpropoxy)Methyl]Pyrrolidin-3-YL}-1-Isopropyl-1H-Indazole-3-Carboxamide and its Ethanedioate

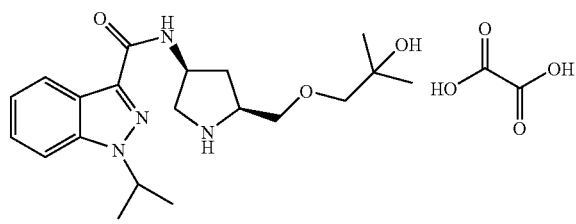

Step 1. tert-Butyl (2S,4S)-2-[(2-ethoxy-2-oxoethoxy)methyl]-4-{[(1-isopropyl-1H-indazol-3-yl)carbonyl]amino}pyrrolidine-1-carboxylate To a stirred solution of tert-butyl (2S,4S)-2-(hydroxymethyl)-4-{[(1-isopropyl-1H-indazol-3-yl)carbonyl]amino}pyrrolidine-1-carboxylate (358 mg, 0.89 mmol, step 2 of Example 7) in tetrahydrofuran (7 mL) was added sodium hydride (60% dispersion in mineral oil, 90 mg, 2.2 mmol) at 0° C. Then to the solution was added 18-crown-6 (164 mg, 0.45 mmol) and a solution of ethyl bromoacetate (446 mg, 2.67 mmol) in tetrahydrofuran (5 mL) at 0° C. It was stirred overnight rising to room temperature. The resulting mixture was quenched by addition of water and it was extracted with ethyl acetate (10 mL×3). The organic layer was washed with brine, dried over sodium sulfate and concentrated. The resulting residue was chromatographed on a column of silica gel eluting with n-hexane/ethyl acetate (2:1 to 1:1) to give 310 mg (71%) of the title compound as a colorless oil.

MS (ESI) m/z: 389 (M+H)+ (−BOC), 487 (M−H)−.

$^1$H NMR (CDCl$_3$) δ 8.44-8.30 (1H, m), 8.40 (1H, d, J=7.9 Hz), 7.48-7.34 (2H, m), 7.31-7.22 (1H, m), 4.95-4.74 (2H, m), 4.44 (1H, d, J=16.5 Hz), 4.26-4.03 (5H, m), 3.91-3.66 (2H, m), 3.47 (1H, dd, J=11.5, 2.3 Hz), 2.67-2.45 (1H, m), 2.17 (1H, d, J=13.8 Hz), 1.61-1.53 (6H, m), 1.46 (9H, s), 1.26 (3H, t, J=7.3 Hz).

Step 2. tert-Butyl (2S,4S)-2-[(2-hydroxy-2-methylpropoxy)methyl]-4-{[(1-isopropyl-1H-indazol-3-yl)carbonyl]amino}pyrrolidine-1-carboxylate The title compound was prepared according to the procedure described in step 1 of Example 10 from tert-butyl (2S,4S)-2-[(2-ethoxy-2-oxoethoxy)methyl]-4-{[(1-isopropyl-1H-indazol-3-yl)carbonyl]amino}pyrrolidine-1-carboxylate (step 1 of Example 12).

MS (ESI) m/z: 375 (M+H)+ (−BOC), 473 (M−H)−.

$^1$H NMR (CDCl$_3$) δ 8.40 (1H, J=7.9 Hz), 7.67 (1H, br s), 7.52-7.34 (2H, m), 7.32-7.21 (1H, m), 5.02-4.65 (2H, m), 4.17-3.88 (2H, m), 3.79-3.65 (1H, m), 3.53-3.25 (3H, m), 2.66-2.46 (1H, m), 1.66-1.54 (8H, m), 1.47 (9H, s), 1.21 (6H, s). A signal due to OH was not observed.

Step 3. N-[(3S,5S)-5-[(2-Hydroxy-2-methylpropoxy)methyl]pyrrolidin-3-yl]-1-isopropyl-1H-indazole-3-carboxamide The title compound was prepared according to the procedure described in step 3 of Example 7 from tert-butyl (2S, 4S)-2-[(2-hydroxy-2-methylpropoxy)methyl]-4-{[(1-isopropyl-1H-indazol-3-yl)carbonyl]amino}pyrrolidine-1-carboxylate (step 2 of Example 12).

MS (ESI) m/z: 375 (M+H)+.

$^1$H NMR (CDCl$_3$) δ 8.39 (1H, J=7.9 Hz), 7.51-7.34 (2H, m), 7.33-7.20 (1H, m), 4.98-4.82 (1H, m), 4.74-4.57 (1H, m), 3.71 (1H, dd, J=9.6, 3.6 Hz), 3.64-3.54 (1H, m), 3.53-3.40 (1H, m), 3.40 (2H, s), 3.29 (1H, dd, J=11.2, 6.6 Hz), 3.03 (1H, dd, J=11.2, 4.3 Hz), 2.50-2.35 (1H, m), 1.64-1.52 (1H, m), 1.61 (6H, d, J=6.6 Hz), 1.21 (6H, s). Signals due to CONH, NH and OH were not observed.

Step 4. N-{(3S,5S)-5-[(2-Hydroxy-2-methylpropoxy)methyl]pyrrolidin-3-yl}-1-isopropyl-1H-indazole-3-carboxamide ethanedioate The title compound was prepared according to the procedure described in step 9 of Example 8 from N-{(3S,5S)-5-[(2-hydroxy-2-methylpropoxy)methyl]pyrrolidin-3-yl}-1-isopropyl-1H-indazole-3-carboxamide (step 3 of Example 12).

MS (ESI) m/z: 375 (M+H)+.

$^1$H NMR (CDCl$_3$) δ 8.30 (1H, J=7.9 Hz), 7.99 (1H, J=7.3 Hz), 7.51-7.34 (2H, m), 7.32-7.23 (1H, m), 4.95-4.75 (2H, m), 4.62-4.20 (3H, m), 4.15-3.58 (4H, m), 3.39 (2H, s), 2.75-2.50 (1H, m), 2.42-2.20 (1H, m), 1.60 (6H, d, J=6.6 Hz), 1.20 (3H, s), 1.16 (3H, s).

Anal. Calcd. for $C_{20}H_{30}N_4O_3 \cdot 1.5\ C_2H_2O_4 \cdot 1.0\ H_2O$: C, 52.36; H, 6.69; N, 10.62. Found: C, 52.20; H, 6.73; N, 10.89.

$[α]_D^{25}$=+43.1° (C=0.12, Methanol).

Example 13

1-Isopropyl-N-{(3S,5S)-5-[2-(Methylamino)-2-Oxoethyl]Pyrrolidin-3-YL}-1H-Indazole-3-Carboxamide

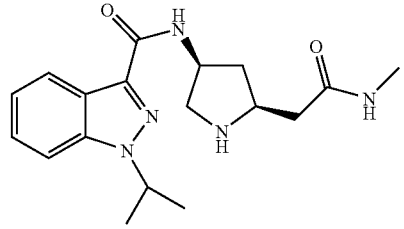

Step 1. ((2S,4S)-1-(tert-Butoxycarbonyl)-4-{[(1-isopropyl-1H-indazol-3-yl)carbonyl]amino}pyrrolidin-2-yl)acetic acid To a stirred solution of tert-butyl (2S,4S)-4-{[(1-isopropyl-1H-indazol-3-yl)carbonyl]amino}-2-(2-methoxy-2-oxoethyl)pyrrolidine-1-carboxylate (0.65 g, 1.46 mmol, step 5 of Example 9) in methanol (10 mL) was added 2N sodium hydroxide aqueous solution (10 mL) at room temperature and the mixture was stirred for 2.5 h. The resulting solution was acidified with 2N hydrochloric acid to be pH 3. Then the mixture was extracted with dichloromethane (10 mL×3). The organic layer was dried over sodium sulfate and concentrated to give 0.62 g (98%) of the title compound as a colorless oil. The residue was used for the next step without further purification.

MS (ESI) m/z: 331 (M+H)+ (−BOC), 429 (M−H)−.

$^1$H NMR (CDCl$_3$) δ 8.35 (1H, J=7.9 Hz), 7.52-7.34 (2H, m), 7.34-7.20 (1H, m), 7.11 (1H, d, J=7.3 Hz), 4.97-4.78 (1H, m), 4.70-4.50 (1H, m), 4.30-4.13 (1H, m), 4.04 (1H, dd,

J=11.2, 7.3 Hz), 3.37-3.00 (2H, m), 2.77-2.55 (2H, m) 2.06-1.80 (1H, m), 1.61 (6H, J=5.9 Hz), 1.48 (9H, s). A signal due to CO$_2$H was not observed.

Step 2. tert-Butyl (2S,4S)-4-{[(1-isopropyl-1H-indazol-3-yl)carbonyl]amino}-2-[2-(methylamino)-2-oxoethyl]pyrrolidine-1-carboxylate The title compound was prepared according to the procedure described in step 1 of Example 7 from ((2S,4S)-1-(tert-butoxycarbonyl)-4-{[(1-isopropyl-1H-indazol-3-yl)carbonyl]amino}pyrrolidin-2-yl)acetic acid (step 1 of Example 13) and methylamine.

MS (ESI) m/z: 344 (M+H)$^+$ (−BOC), 442 (M−H)$^-$.

$^1$H NMR (CDCl$_3$) δ 8.36 (1H, J=7.9 Hz), 7.50-7.35 (2H, m), 7.35-7.21 (1H, m), 6.05 (1H, br s), 4.97-4.79 (1H, m), 4.69-4.50 (1H, m), 4.21-4.04 (1H, m), 4.04 (1H, dd, J=11.2, 7.3 Hz), 3.28-3.12 (1H, m), 2.85-2.65 (1H, m), 2.79 (3H, d, J=4.6 Hz) 2.65-2.50 (1H, m), 2.41-2.18 (1H, m), 1.80-1.68 (1H, m), 1.62 (6H, d, J=6.6 Hz), 1.47 (9H, s).

Signals due to CONH and CONH were not observed.

Step 3. 1-Isopropyl-N-{(3S,5S)-5-[2-(methylamino)-2-oxoethyl]pyrrolidin-3-yl}-1H-indazole-3-carboxamide The title compound was prepared according to the procedure described in step 3 of Example 7 from tert-butyl (2S,4S)-4-{[(1-isopropyl-1H-indazol-3-yl)carbonyl]amino}-2-[2-(methylamino)-2-oxoethyl]pyrrolidine-1-carboxylate (step 2 of Example 13).

MS (ESI) m/z: 344 (M+H)$^+$, 342 (M−H)$^-$.

$^1$H NMR (CDCl$_3$) δ 8.36 (1H, J=7.9 Hz), 7.50-7.35 (2H, m), 7.34-7.23 (1H, m), 7.00 (1H, br s), 4.95-4.79 (1H, m), 4.73-4.52 (1H, m), 3.62-3.45 (1H, m), 3.33 (1H, dd, J=11.2, 6.6 Hz), 3.09 (1H, dd, J=11.2, 4.0), 2.83 (3H, d, J=4.6 Hz), 2.66-2.39 (3H, m), 1.60 (6H, d, J=6.6 Hz), 1.64-1.48 (1H, m). Signals due to NH and CONH were not observed.

HRMS (FAB) m/z calcd for C$_{18}$H$_{26}$N$_5$O$_2$ ([M+H]$^+$) 344.2087, found 344.2112.

[α]$_D^{23}$=−34.0° (C=0.25, Methanol).

Example 14

1-Isopropyl-N-[(3S,5S)-5-(2-Morpholin-4-Yl-2-Oxoethyl)Pyrrolidin-3-Yl]-1H-Indazole-3-Carboxamide

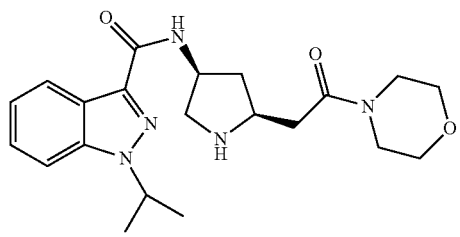

Step 1. tert-Butyl (2S,4S)-4-{[(1-isopropyl-1H-indazol-3-yl)carbonyl]amino}-2-(2-morpholin-4-yl-2-oxoethyl)pyrrolidine-1-carboxylate The title compound was prepared according to the procedure described in step 1 of Example 7 from ((2S,4S)-1-(tert-butoxycarbonyl)-4-{[(1-isopropyl-1H-indazol-3-yl)carbonyl]amino}pyrrolidin-2-yl)acetic acid (step 1 of Example 13) and morpholine.

MS (ESI) m/z: 400 (M+H)$^+$ (−BOC).

$^1$H NMR (CDCl$_3$) δ 8.36 (1H, J=7.9 Hz), 7.50-7.33 (3H, m), 7.32-7.23 (1H, m), 4.97-4.77 (1H, m), 4.70-4.48 (1H, m), 4.27-4.00 (2H, m), 3.75-3.45 (6H, m), 3.36-3.11 (2H, m), 2.70-2.52 (2H, m) 2.21-2.04 (1H, m), 1.86-1.65 (1H, m), 1.61 (6H, d, J=6.6 Hz), 1.47 (9H, s), 1.45-1.27 (1H, m).

Step 2. 1-Isopropyl-N-[(3S,5S)-5-(2-morpholin-4-yl-2-oxoethyl)pyrrolidin-3-yl]-1H-indazole-3-carboxamide The title compound was prepared according to the procedure described in step 3 of Example 7 from tert-butyl (2S,4S)-4-{[(1-isopropyl-1H-indazol-3-yl)carbonyl]amino}-2-(2-morpholin-4-yl-2-oxoethyl)pyrrolidine-1-carboxylate (step 1 of Example 14).

MS (ESI) m/z: 400 (M+H)$^+$, 398 (M−H)$^-$.

$^1$H NMR (CDCl$_3$) δ 8.37 (1H, J=8.6 Hz), 7.49-7.35 (3H, m), 7.31-7.23 (1H, m), 4.95-4.80 (1H, m), 4.78-4.63 (1H, m), 3.73-3.51 (7H, m), 3.51-3.43 (2H, m), 3.33 (1H, dd, J=10.9, 6.9 Hz), 3.09 (1H, dd, J=11.2, 3.3 Hz), 2.73-2.48 (3H, m), 1.60 (6H, d, J=6.6 Hz), 1.62-1.48 (1H, m).

A signal due to NH was not observed.

HRMS (FAB) m/z calcd for C$_{21}$H$_{30}$N$_5$O$_3$ ([M+H]$^+$) 400.2349, found 400.2334.

[α]$_D^{23}$=−21.6° (C=0.26, Methanol).

Example 15

1-Isopropyl-N-[(3S,5S)-5-(2-Oxo-2-Piperidin-1-Ylethyl)Pyrrolidin-3-Yl]-1H-Indazole-3-Carboxamide

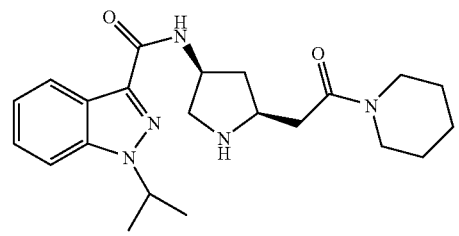

Step 1. tert-Butyl (2S,4S)-4-{[(1-Isopropyl-1H-indazol-3-yl)carbonyl])amino}-2-(2-oxo-2-piperidin-1-ylethyl)pyrrolidine-1-carboxylate The title compound was prepared according to the procedure described in step 1 of Example 7 from ((2S,4S)-1-(tert-butoxycarbonyl)-4-{[(1-isopropyl-1H-indazol-3-yl)carbonyl]amino}pyrrolidin-2-yl)acetic acid (step 1 of Example 13) and piperidine.

MS (ESI) m/z: 398 (M+H)$^+$.

$^1$H NMR (CDCl$_3$) δ 8.36 (1H, J=7.9 Hz), 7.55-7.35 (3H, m), 7.31-7.22 (1H, m), 4.97-4.77 (1H, m), 4.71-4.43 (1H, m), 3.66-3.35 (4H, m), 3.35-3.18 (2H, m) 3.15-3.03 (2H, m), 2.67-2.48 (2H, m), 2.20-2.04 (1H, m), 1.61 (6H, d, J=6.6 Hz), 1.60-1.44 (6H, m), 1.47 (9H, s).

Step 2. 1-Isopropyl-N-[(3S,5S)-5-(2-oxo-2-piperidin-1-ylethyl)pyrrolidin-3-yl]-1H-indazole-3-carboxamide The title compound was prepared according to the procedure described in step 3 of Example 7 from tert-butyl (2S,4S)-4-{[(1-isopropyl-1H-indazol-3-yl)carbonyl]amino}-2-(2-oxo-2-piperidin-1-ylethyl)pyrrolidine-1-carboxylate (step 1 of Example 15).

MS (ESI) m/z: 398 (M+H)$^+$, 396 (M−H)$^−$.
$^1$H NMR (CDCl$_3$) δ 8.37 (1H, J=7.9 Hz), 7.53 (1H, d, J=8.6 Hz), 7.49-7.32 (2H, m), 7.30-7.21 (1H, m), 4.93-4.80 (1H, m), 4.80-4.66 (1H, m), 3.66-3.50 (3H, m), 3.45-3.35 (2H, m), 3.33 (1H, dd, J=10.9, 6.9 Hz), 3.11 (1H, dd, J=11.2, 3.3 Hz), 2.76-2.46 (4H, m), 1.60 (6H, d, J=6.6 Hz), 1.70-1.46 (6H, m).
A signal due to NH was not observed.
HRMS (FAB) m/z calcd for C$_{22}$H$_{32}$N$_5$O$_2$ ([M+H]$^+$) 398.2556, found 398.2564.
[α]$_D^{23}$=−27.9° (C=0.25, Methanol).

Example 16

N-{(3S,5S)-5-[2-(Dim Ethylamino)-2-Oxoethyl] Pyrrolidin-3-Yl}-1-Isopropyl-1H-Indazole-3-Carboxamide

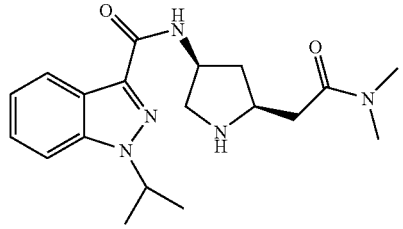

Step 1. tert-Butyl (2S,4S)-2-[2-(dimethylamino)-2-oxoethyl]-4-{[(1-isopropyl-1H-indazol-3-yl)carbonyl]amino}pyrrolidine-1-carboxylate The title compound was prepared according to the procedure described in step 1 of Example 7 from ((2S,4S)-1-(tert-butoxycarbonyl)-4-{[(1-isopropyl-1H-indazol-3-yl)carbonyl]amino}pyrrolidin-2-yl)acetic acid (step 1 of Example 13) and dimethylamine.

MS (ESI) m/z: 358 (M+H)$^+$ (−BOC).
$^1$H NMR (CDCl$_3$) δ 8.36 (1H, J=7.9 Hz), 7.50-7.33 (3H, m), 7.32-7.22 (1H, m), 4.96-4.80 (1H, m), 4.70-4.50 (1H, m), 4.30-4.14 (1H, m), 4.07 (1H, dd, J=11.2, 7.3 Hz), 3.35-3.15 (2H, m), 3.08 (3H, s) 2.94 (3H, s), 2.73-2.50 (2H, m), 2.20-2.00 (1H, m), 1.61 (6H, d, J=6.6 Hz), 1.47 (9H, s).

Step 2. N-[(3S,5S)-5-[2-(Dimethylamino)-2-oxoethyl]pyrrolidin-3-yl]-1-isopropyl-1H-indazole-3-carboxamide The title compound was prepared according to the procedure described in step 3 of Example 7 from tert-butyl (2S,4S)-2-[2-(dimethylamino)-2-oxoethyl]-4-{[(1-isopropyl-1H-indazol-3-yl)carbonyl]amino}pyrrolidine-1-carboxylate (step 1 of Example 16).

MS (ESI) m/z: 358 (M+H)$^+$
$^1$H NMR (CDCl$_3$) δ 8.38 (1H, J=7.9 Hz), 7.53 (1H, d, J=7.9 Hz), 7.49-7.35 (2H, m), 7.31-7.22 (1H, m), 4.94-4.80 (1H, m), 4.80-4.65 (1H, m), 3.68-3.51 (1H, m), 3.32 (1H, dd, J=10.9, 6.9 Hz), 3.11 (1H, dd, J=11.2, 3.3 Hz), 3.02 (3H, s) 2.97 (3H, s), 2.80-2.45 (3H, m), 1.61 (6H, d, J=6.6 Hz), 1.66-1.53 (1H, m).
A signal due to NH was not observed.
HRMS (FAB) m/z calcd for C$_{19}$H$_{28}$N$_5$O$_2$ ([M+H]$^+$) 358.2243, found 358.2254.
[α]$_D^{25}$=−13.9° (C=0.06, Methanol).

Example 17

N-{(3S,5S)-5-[(Acetylamino)Methyl]Pyrrolidin-3-Yl}-1-Isopropyl-1H-Indazole-3-Carboxamide and its Ethanedioate

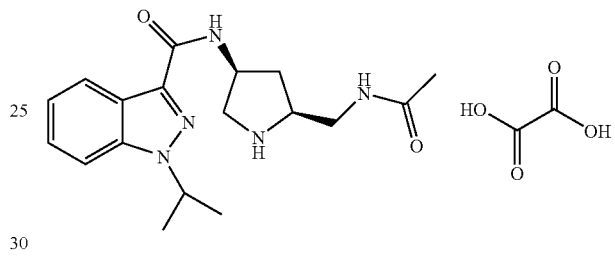

Step 1. tert-butyl (2S,4S)-4-{[(1-isopropyl-1H-indazol-3-yl)carbonyl]amino}-2-{[(methylsulfonyl)oxy]methyl}pyrrolidine-1-carboxylate To a stirred mixture of tert-butyl (2S,4S)-2-(hydroxymethyl)-4-{[(1-isopropyl-1H-indazol-3-yl) carbonyl]amino}pyrrolidine-1-carboxylate (2.00 g, 4.97 mmol, step 2 of Example 7) and triethylamine (1.4 mL, 9.94 mmol) in tetrahydrofuran (40 mL) was added methanesulfonyl chloride (0.46 mL, 5.96 mmol) at 0° C. The mixture was stirred at room temperature for 3 h. Then the reaction mixture was quenched by addition of water and extracted with ethyl acetate (20 mL×3). The organic layer was washed with brine, dried over sodium sulfate and concentrated to give the crude mesylate (2.44 g, quant) as a colorless gum.
$^1$H NMR (CDCl$_3$) δ 8.36 (1H, J=8.6 Hz), 7.51-7.36 (2H, m), 7.33-7.24 (1H, m), 7.20 (1H, d, J=7.3 Hz), 4.99-4.81 (1H, m), 4.79-4.60 (2H, m), 4.41-4.32 (1H, m), 4.24-4.00 (2H, m), 3.36-3.17 (1H, m), 3.03 (3H, s), 2.70-2.50 (1H, m), 2.20-2.00 (1H, m), 1.63 (6H, d, J=6.6 Hz), 1.48 (9H, s).

Step 2. tert-Butyl (2S,4S)-2-(aminomethyl)-4-{[(1-isopropyl-1H-indazol-3-yl)carbonyl]amino}pyrrolidine-1-carboxylate The mixture of tert-butyl (2S,4S)-4-{[(1-isopropyl-1H-indazol-3-yl)carbonyl]amino}-2-{[(methylsulfonyl)oxy]methyl}pyrrolidine-1-carboxylate (1.32 g, 2.7 mmol, step 1 of Example 17) and sodium azide (0.89 g, 13 mmol) in N,N-dimethylformamide (25 mL) was stirred at 60° C. for 24 h. The resulting mixture was added to water and extracted with diethyl ether (15 mL×3). The organic layer was washed with water (twice) and brine, dried over sodium sulfate and concentrated to give the crude azide (1.07 g, 91%) as a colorless gum.

To a stirred solution of the crude azide in methanol (30 mL) was added 10 wt. % palladium on carbon (150 mg). The resulting mixture was stirred under hydrogen (1 atom) at room temperature for 8 h. Then the reaction mixture was filtered off though a pad of Celite. The filtrate was concentrated to give 0.95 g (95%) of the title compound as a white solid. The residue was used for the next step without further purification.

MS (ESI) m/z: 400 (M+H)$^+$.

$^1$H NMR (CDCl$_3$) δ 8.39 (1H, J=7.9 Hz), 7.48-7.34 (2H, m), 7.31-7.21 (1H, m), 4.96-4.65 (2H, m), 4.13-3.92 (1H, m), 3.90-3.65 (1H, m), 3.60-3.30 (2H, m), 2.68 (1H, dd, J=12.9, 2.3 Hz), 2.66-2.46 (1H, m), 1.98-1.87 (1H, m), 1.58 (6H, d, J=6.6 Hz), 1.46 (9H, s). Signals due to N2 and CONH were not observed.

Step 3. tert-Butyl (2S,4S)-2-[(acetylamino)methyl]-4-{[(1-isopropyl-1H-indazol-3-yl)carbonyl]amino}pyrrolidine-1-carboxylate To the mixture of tert-butyl (2S,4S)-2-(aminomethyl)-4-{[(1-isopropyl-1H-indazol-3-yl)carbonyl]amino}pyrrolidine-1-carboxylate (202 mg, 0.5 mmol, step 2 of Example 17) and triethylamine (140 µL, 1.0 mmol) in dichloromethane (2 mL) was added acetyl chloride (43 µL, 0.55 mmol) at 0° C. The mixture was allowed to warm to room temperature and stirred for 2 h. The resulting solution was added to water and extracted with ethyl acetate (10 mL×3). The organic layer was washed with brine, dried over sodium sulfate and concentrated. The residue was PTLC eluting with dichloromethane/methanol (30:1 and 20:1 twice) to give 200 mg (90%) of the title compound as a colorless amorphous.

MS (ESI) m/z: 344 (M+H)$^+$ (−BOC), 442 (M+H)$^-$.

$^1$H NMR (CDCl$_3$) δ 8.35 (1H, d, J=7.9 Hz), 7.51-7.35 (3H, m), 7.33-7.24 (1H, m), 7.19 (1H, br s), 4.98-4.79 (1H, m), 4.66-4.49 (1H, m), 4.18-3.97 (2H, m), 3.75-3.57 (1H, m), 3.49-3.25 (1H, m), 3.28 (1H, dd, J=11.2, 6.6 Hz), 2.63-2.45 (1H, m), 2.01 (3H, s), 1.93-1.69 (1H, m), 1.66-1.58 (6H, m), 1.48 (9H, s).

Step 4. N-{(3S,5S)-5-[(Acetylamino)methyl]pyrrolidin-3-yl}-1-isopropyl-1H-indazole-3-carboxamide The title compound was prepared according to the procedure described in step 3 of Example 7 from tert-butyl (2S,4S)-2-[(acetylamino)methyl]-4-{[(1-isopropyl-1H-indazol-3-yl)carbonyl]amino}pyrrolidine-1-carboxylate (step 3 of Example 17).

MS (ESI) m/z: 344 (M+H)$^+$, 342 (M−H)$^-$.

$^1$H NMR (CDCl$_3$) δ 8.37 (1H, d, J=7.9 Hz), 7.50-7.36 (2H, m), 7.32-7.23 (1H, m), 7.16 (1H, d, J=7.3 Hz), 6.12 (1H, br s), 4.96-4.80 (1H, m), 4.64-4.48 (1H, m), 3.54-3.21 (4H, m), 2.95 (1H, dd, J=11.2, 5.3 Hz), 2.53-2.38 (1H, m), 2.01 (3H, s), 1.61 (6H, d, J=6.6 Hz), 1.63-1.43 (1H, m). A signal due to NH was not observed.

Step 5. N-{(3S,5S)-5-[(Acetylamino)methyl]pyrrolidin-3-yl}-1-isopropyl-1H-indazole-3-carboxamide ethanedioate The title compound was prepared according to the procedure described in step 9 of Example 8 from N-{(3S,5S)-5-[(acetylamino)methyl]pyrrolidin-3-yl}-1-isopropyl-1H-indazole-3-carboxamide (step 4 of Example 17).

MS (ESI) m/z: 344 (M+H)$^+$, 342 (M−H)$^-$.

IR (KBr) v: 2982, 1719, 1646, 1540, 1405, 1280, 1198, 721 cm$^{-1}$ $^1$H NMR (CD$_3$OD) δ 8.23 (1H, J=8.0 Hz), 7.68 (1H, J=8.0 Hz), 7.45 (1H, t, J=8.0 Hz), 7.28 (1H, t, J=8.0 Hz), 5.14-4.98 (1H, m), 4.77-4.60 (1H, m), 3.90-3.74 (1H, m), 3.74-3.50 (4H, m), 2.71-2.55 (1H, m), 2.17-1.98 (1H, m), 2.04 (3H, s), 1.61 (6H, d, J=6.6 Hz). Signals due to CONH and NH were not observed.

Anal. Calcd. for C$_{18}$H$_{25}$N$_5$O$_2$.1.5 C$_2$H$_2$O$_4$.0.1 H$_2$O: C, 52.52; H, 5.92; N, 14.58. Found: C, 52.26; H, 6.08; N, 14.34.

$[α]_D^{25}$=+33.5° (C=0.26, Methanol).

Example 18

1-Isopropyl-N-((3S,5S)-5-{[(Methylsulfonyl)Amino]Methyl}Pyrrolidin-3-YL)-1H-Indazole-3-Carboxamide and its Ethanedioate

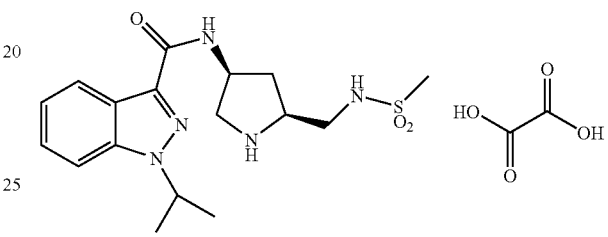

Step 1. tert-Butyl (2S,4S)-4-{[(1-isopropyl-1H-indazol-3-yl)carbonyl]amino}-2-{[(methylsulfonyl)amino]methyl}pyrrolidine-1-carboxylate The title compound was prepared according to the procedure described in step 3 of Example 17 from tert-butyl (2S,4S)-2-(aminomethyl)-4-{[(1-isopropyl-1H-indazol-3-yl)carbonyl]amino}pyrrolidine-1-carboxylate (step 2 of Example 17) and methanesulfonyl chloride.

MS (ESI) m/z: 380 (M+H)$^+$ (−BOC), 478 (M+H)$^-$.

$^1$H NMR (CDCl$_3$) δ 8.35 (1H, d, J=8.6 Hz), 7.51-7.35 (2H, m), 7.33-7.23 (1H, m), 7.18 (1H, d, J=7.3 Hz), 5.78 (1H, br s), 4.98-4.80 (1H, m), 4.69-4.51 (1H, m), 4.17-3.98 (2H, m), 3.61-3.44 (1H, m), 3.41-3.19 (2H, m), 2.97 (3H, s), 2.64-2.47 (1H, m), 2.08-1.85 (1H, m), 1.62 (6H, d, J=6.6 Hz), 1.48 (9H, s).

Step 2. 1-isopropyl-N-((3S,5S)-5-{[(methylsulfonyl)amino]methyl}pyrrolidin-3-yl)-1H-indazole-3-carboxamide The title compound was prepared according to the procedure described in step 3 of Example 7 from tert-butyl (2S,4S)-4-{[(1-isopropyl-1H-indazol-3-yl)carbonyl]amino}-2-{[(methylsulfonyl)amino]methyl}pyrrolidine-1-carboxylate (step 1 of Example 18).

MS (ESI) m/z: 380 (M+H)$^+$, 378 (M−H)$^-$.

$^1$H NMR (CDCl$_3$) δ 8.36 (1H, d, J=7.9 Hz), 7.50-7.36 (2H, m), 7.31-7.23 (1H, m), 7.19 (1H, d, J=7.3 Hz), 4.98-4.80 (1H, m), 4.69-4.51 (1H, m), 3.59-3.45 (1H, m), 3.38 (1H, dd, J=11.2, 6.6 Hz), 3.28 (1H, dd, J=12.5, 4.6 Hz), 3.13 (1H, dd, J=12.5, 6.3 Hz), 3.00 (3H, s), 2.91 (1H, dd, J=11.2, 5.9 Hz), 2.47 (1H, td, J=13.2, 7.9 Hz), 1.69-1.57 (1H, m), 1.62 (6H, d, J=7.3 Hz).

Signals due to (SO$_2$NH or CONH) and NH were not observed.

Step 3. 1-Isopropyl-N-((3S,5S)-5-{[(methylsulfonyl) amino]methyl}pyrrolidin-3-yl)-1H-indazole-3-carboxamide ethanedioate The title compound was prepared according to the procedure described in step 9 of Example 8 from 1-isopropyl-N-((3S,5S)-5-{[(methylsulfonyl)amino]methyl}pyrrolidin-3-yl)-1H-indazole-3-carboxamide (step 2 of Example 18).

MS (ESI) m/z: 380 (M+H)$^+$, 378 (M−H)$^-$.
IR (KBr) ν: 3266, 2983, 1719, 1654, 1534, 1406, 1310, 1206, 1143, 980, 721 cm$^{-1}$
$^1$H NMR (CD$_3$OD) δ 8.23 (1H, J=7.8 Hz), 7.68 (1H, J=7.8 Hz), 7.45 (1H, t, J=7.8 Hz), 7.28 (1H, t, J=7.8 Hz), 5.12-4.97 (1H, m), 4.83-4.65 (1H, m), 3.94-3.75 (1H, m), 3.75-3.40 (4H, m), 3.04 (3H, s), 2.77-2.59 (1H, m), 2.11-1.96 (1H, m), 1.61 (6H, d, J=7.3 Hz). Signals due to CONH and NH were not observed.
Anal. Calcd. for C$_{17}$H$_{25}$N$_5$O$_3$S.1.0 C$_2$H$_2$O$_4$.0.1 C$_4$H$_{10}$O.0.1 H$_2$O: C, 48.67; H, 5.94; N, 14.63. Found: C, 48.27; H, 5.89; N, 14.25.
[α]$_D^{24}$=+10.9° (C=0.25, Methanol).

Example 19

N-{(3S,5R)-5-[2-(Acetylamino)Ethyl]Pyrrolidin-3-Yl}-1-Isopropyl-1H-Indazole-3-Carboxamide Ethanedioate

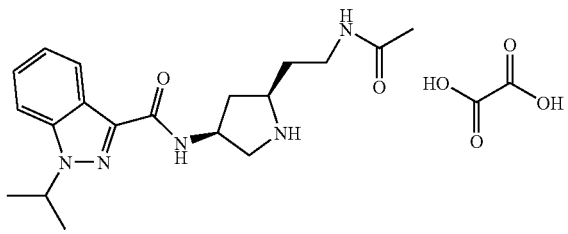

Step 1: tert-Butyl (2S,4S)-2-(cyanomethyl)-4-{[(1-isopropyl-1H-indazol-3-yl)carbonyl] amino}pyrrolidine-1-carboxylate The title compound was prepared according to the procedure described in Step 1 of Example 9 from tert-butyl (2S,4S)-4-{[(1-isopropyl-1H-indazol-3-yl)carbonyl]amino}-2-{[(methylsulfonyl)oxy]methyl}pyrrolidine-1-carboxylate (Step 1 of Example 17).
$^1$H NMR (CDCl$_3$) δ8.36 (1H, d, J=8.6 Hz), 7.52-7.22 (3H, m), 7.11 (1H, d, J=7.9 Hz), 4.98-4.59 (2H, m), 4.19-4.01 (2H, m), 3.82-3.19 (2H, m), 2.82-2.65 (1H, m), 2.13-1.88 (1H, m), 1.69-1.34 (16H, m).

Step 2: tert-Butyl (2R,4S)-2-(2-aminoethyl)-4-{[(1-isopropyl-1H-indazol-3-yl)carbonyl] amino}pyrrolidine-1-carboxylate The mixture of tert-butyl (2S,4S)-2-(cyanomethyl)-4-{[(1-isopropyl-1H-indazol-3-yl)carbonyl]amino}pyrrolidine-1-carboxylate (0.40 g, 0.97 mmol, Step 1 of Example 19) and catalytic Raney-Ni in methanol (16 mL) and 25% ammonium hydroxide (4.0 mL) was stirred under hydrogen (4 atom) at room temperature for 7 h. The mixture was filtered through a pad of Celite. The filtrate was concentrated under reduced pressure. The residue was purified by silica gel column chromatography (n-hexane/ethyl acetate 1:1 to dichloromethane/methanol 10:1) to give 115 mg (65%) of the title compound as a colorless oil.
$^1$H NMR (CDCl$_3$) δ 8.37 (1H, d, J=7.9 Hz), 7.51-7.22 (3H, m), 6.70 (1H, br), 4.97-4.80 (1H, m), 4.69-4.51 (1H, m), 4.19-3.90 (2H, m), 3.34-3.19 (1H, m), 2.78 (2H, t, J=6.6 Hz), 2.64-2.49 (1H, m), 2.23-2.00 (1H, m), 1.93-1.14 (17H, m). Signals due to NH$_2$ were not observed.

Step 3: tert-Butyl (2R,4S)-2-[2-(acetylamino)ethyl]-4-{[(1-isopropyl-1H-indazol-3-yl)carbonyl] amino}pyrrolidine-1-carboxylate The title compound was prepared according to the procedure described in Step 3 of Example 17 from tert-butyl (2R,4S)-2-(2-aminoethyl)-4-{[(1-isopropyl-1H-indazol-3-yl)carbonyl]amino}pyrrolidine-1-carboxylate (Step 2 of Example 19).
$^1$H NMR (CDCl$_3$) δ 8.36 (1H, d, J=7.9 Hz), 7.51-7.23 (3H, m), 7.06 (1H, d, J=6.6 Hz), 6.70 (1H, br), 4.97-4.80 (1H, m), 4.68-4.49 (1H, m), 4.18-3.95 (2H, m), 3.69-2.94 (2H, m), 2.68-2.52 (1H, m), 2.00 (3H, s), 1.95-1.35 (19H, m).

Step 4: N-{(3S,5R)-5-[2-(Acetylamino)ethyl]pyrrolidin-3-yl}-1-isopropyl-1H-indazole-3-carboxamide ethanedioate The title compound was prepared according to the procedure described in step 4 of Example 4 from tert-butyl (2R,4S)-2-[2-(acetylamino)ethyl]-4-{[(1-isopropyl-1H-indazol-3-yl)carbonyl]amino}pyrrolidine-1-carboxylate (Step 3 of Example 19).
MS (ESI) m/z: 358 (M+H)$^+$.
IR (KBr) ν: 3340, 2942, 1654, 1540, 1206 cm$^{-1}$
$^1$H NMR (DMSO-d$_6$) δ 8.53 (1H, d, J=7.9 Hz), 8.17 (1H, d, J=8.6 Hz), 8.08-8.00 (1H, m), 7.82 (1H, d, J=8.6 Hz), 7.50-7.40 (1H, m), 7.32-7.24 (1H, m), 5.18-5.01 (1H, m), 4.77-4.60 (1H, m), 3.60-3.40 (2H, m), 3.34-3.05 (3H, m), 2.62-2.50 (1H, m), 2.02-1.71 (6H, m), 1.55 (6H, d, J=6.6 Hz). Signals due to NH and CO$_2$H were not observed.
Anal. Calcd. for C$_{19}$H$_{27}$N$_5$O$_2$.1.5 C$_2$H$_2$O$_4$.1.0 H$_2$O: C, 51.76; H, 6.32; N, 13.72. Found: C, 51.61; H, 6.45; N, 14.02.
[α]$_D^{23}$=−17.1° (C=0.25, Methanol).

Example 20

N-{(3S,5R)-5-[2-(Isobutyrylamino)Ethyl]Pyrrolidin-3-Yl}-1-Isopropyl-1H-Indazole-3-Carboxamide Ethanedioate

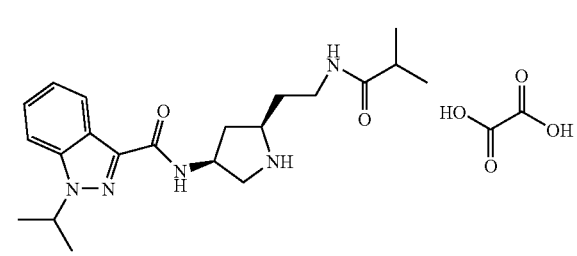

Step 1: tert-Butyl (2R,4S)-2-[2-(isobutyrylamino) ethyl]-4-{[(1-isopropyl-1H-indazol-3-yl)carbonyl] amino}pyrrolidine-1-carboxylate The title compound was prepared according to the procedure described in Step 3 of Example 17 from tert-butyl (2R, 4S)-2-(2-aminoethyl)-4-{[(1-isopropyl-1H-indazol-3-yl)carbonyl]amino}pyrrolidine-1-carboxylate (Step 2 of Example 19) and isobutyryl chloride.

$^1$H NMR (CDCl$_3$) δ 8.36 (1H, d, J=7.9 Hz), 7.51-7.23 (3H, m), 7.06 (1H, d, J=7.3 Hz), 6.68 (1H, br), 4.97-4.80 (1H, m), 4.68-4.49 (1H, m), 4.18-3.95 (2H, m), 3.69-2.94 (2H, m), 2.68-2.52 (1H, m), 2.48-2.27 (1H, m), 1.95-1.35 (25H, m).

Step 2: N-{(3S,5R)-5-[2-(Isobutyrylamino)ethyl]pyrrolidin-3-yl}-1-isopropyl-1H-indazole-3-carboxamide ethanedioate The title compound was prepared according to the procedure described in Step 4 of Example 4 from tert-butyl (2R,4S)-2-[2-(isobutyrylamino)ethyl]-4-{[(1-isopropyl-1H-indazol-3-yl)carbonyl]amino}pyrrolidine-1-carboxylate (Step 1 of Example 20).

MS (ESI) m/z: 386 (M+H)$^+$.

IR (KBr) ν: 3314, 2978, 1644, 1529, 1186 cm$^{-1}$ $^1$H NMR (DMSO-d$_6$) δ 8.53 (1H, d, J=7.9 Hz), 8.17 (1H, d, J=8.6 Hz), 8.08-8.00 (1H, m), 7.82 (1H, d, J=8.6 Hz), 7.50-7.40 (1H, m), 7.32-7.24 (1H, m), 5.18-5.01 (1H, m), 4.77-4.60 (1H, m), 3.60-3.40 (2H, m), 3.34-3.05 (3H, m), 2.62-2.50 (1H, m), 2.42-2.28 (1H, m), 2.02-1.71 (3H, m), 1.55 (6H, d, J=6.6 Hz), 1.01 (6H, d, J=7.3 Hz). Signals due to NH and CO$_2$H were not observed.

Anal. Calcd. for C$_{21}$H$_{31}$N$_5$O$_2$·1.0 C$_2$H$_2$O$_4$·0.8 H$_2$O: C, 56.38; H, 7.12; N, 14.29. Found: C, 56.46; H, 7.09; N, 14.26.

[α]$_D^{23}$=−8.1° (C=0.25, Methanol).

Example 21

N-((3S,5S)-5-{[2-(Dimethylamino)-2-Oxoethoxy]Methyl}Pyrrolidin-3-Yl)-1-Isopropyl-1H-Indazole-3-Carboxamide

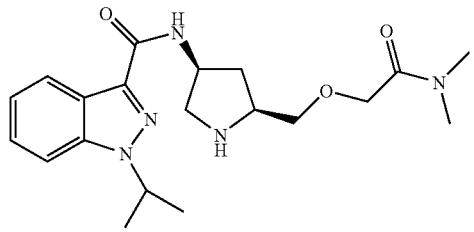

Step 1. [((2S,4S)-1-(tert-butoxycarbonyl)-4-{[(1-isopropyl-1H-indazol-3-yl)carbonyl]amino}pyrrolidin-2-yl)methoxy]acetic acid The title compound was prepared according to the procedure described in step 1 of Example 13 from tert-butyl (2S,4S)-2-[(2-ethoxy-2-oxoethoxy)methyl]-4-{[(1-isopropyl-1H-indazol-3-yl)carbonyl]amino}pyrrolidine-1-carboxylate (step 1 of Example 12).

MS (ESI) m/z: 361 (M+H)$^+$ (−BOC), 459 (M−H)$^-$.

Step 2. tert-Butyl (2S,4S)-2-{[2-(dimethylamino)-2-oxoethoxy]methyl}-4-{[(1-isopropyl-1H-indazol-3-yl)carbonyl]amino}pyrrolidine-1-carboxylate The title compound was prepared according to the procedure described in step 1 of Example 7 from [((2S,4S)-1-(tert-Butoxycarbonyl)-4-{[(1-isopropyl-1H-indazol-3-yl)carbonyl]amino}pyrrolidin-2-yl)methoxy]acetic acid (step 1 of Example 21) and dimethylamine.

MS (ESI) m/z: 388 (M+H)$^+$ (−BOC), 486 (M−H)$^-$.

$^1$H NMR (CDCl$_3$) δ 8.40 (1H, J=8.6 Hz), 8.41-8.10 (1H, m), 7.48-7.32 (2H, m), 7.31-7.20 (1H, m), 4.96-4.65 (2H, m), 4.38 (2H, d, J=4.0 Hz), 4.18-3.95 (2H, m), 3.59-3.75 (1H, m), 3.70 (1H, dd, J=10.4, 2.3 Hz), 3.43 (1H, dd, J=10.4, 2.3 Hz) 2.98 (3H, s), 2.94 (3H, s), 2.65-2.45 (1H, m), 2.30-2.10 (1H, m), 1.59 (6H, d, J=6.6 Hz), 1.46 (9H, s).

Step 3. N-((3S,5S)-5-{[2-(Dimethylamino)-2-oxoethoxy]methyl}pyrrolidin-3-yl)-1-isopropyl-1H-indazole-3-carboxamide The title compound was prepared according to the procedure described in step 3 of Example 7 from tert-butyl (2S,4S)-2-{[2-(dimethylamino)-2-oxoethoxy]methyl}-4-{[(1-isopropyl-1H-indazol-3-yl)carbonyl]amino}pyrrolidine-1-carboxylate (step 2 of Example 21).

MS (ESI) m/z: 388 (M+H)$^+$.

IR (KBr) ν: 3356, 2843, 1661, 1538, 1449, 1284, 1196, 1116, 1095, 880, 757 cm$^{-1}$ $^1$H NMR (CDCl$_3$) δ 8.39 (1H, J=7.9 Hz), 7.57 (1H, d, J=7.9 Hz), 7.48-7.35 (2H, m), 7.30-7.21 (1H, m), 4.95-4.79 (1H, m), 4.75-4.61 (1H, m), 4.30 (2H, s), 3.73-3.58 (2H, m), 3.55-3.42 (1H, m), 3.23-3.06 (2H, m), 3.00 (3H, s), 2.96 (3H, s), 2.46-2.30 (1H, m), 1.78-1.65 (1H, m), 1.59 (6H, d, J=6.6 Hz).

A signal due to NH was not observed.

Anal. Calcd. for C$_{20}$H$_{29}$N$_5$O$_3$·0.2 H$_2$O: C, 61.42; H, 7.58; N, 17.91. Found: C, 61.20; H, 7.49; N, 17.52.

[α]$_D^{25}$=−18.6° (C=0.25, Methanol).

Example 22

N-[(3S,5S)-5-(2-Ethyl-2-Hydroxybutyl)Pyrrolidin-3-Yl]-1-Isopropyl-1H-Indazole-3-Carboxamide and its Ethanedioate

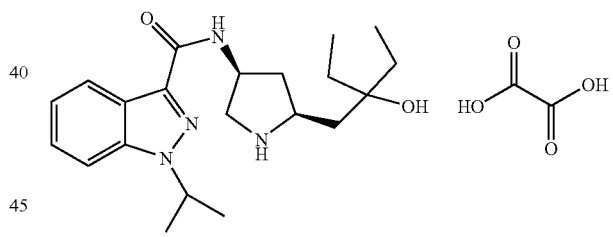

Step 1. tert-Butyl (2S,4S)-2-(2-ethyl-2-hydroxybutyl)-4-{[(1-isopropyl-1H-indazol-3-yl)carbonyl]amino}pyrrolidine-1-carboxylate The title compound was prepared according to the procedure described in step 1 of Example 10 using ethylmagnesium bromide instead of methylmagnesium bromide.

MS (ESI) m/z: 373 (M+H)$^+$ (−BOC), 471 (M−H)$^-$.

$^1$H NMR (CDCl$_3$) δ 8.37 (1H, d, J=8.1 Hz), 7.48-7.27 (4H, m), 4.89-4.80 (1H, m), 4.93-4.84 (1H, m), 4.66-4.57 (1H, m), 4.25-4.09 (1H, m), 3.98 (1H, dd, J=11.4, 7.0 Hz), 3.72 (1H, br s), 3.34 (1H, dd, J=11.7, 5.1 Hz), 2.59-2.41 (1H, m), 2.17-1.94 (2H, m), 1.75-1.47 (19H, m), 0.93-0.84 (6H, m).

Step 2. N-[(3S,5S)-5-(2-Ethyl-2-hydroxybutyl)pyrrolidin-3-yl]-1-isopropyl-1H-indazole-3-carboxamide The title compound was prepared according to the procedure described in step 3 of Example 7 from tert-butyl (2S, 4S)-2-(2-ethyl-2-hydroxybutyl)-4-{[(1-isopropyl-1H-indazol-3-yl)carbonyl]amino}pyrrolidine-1-carboxylate (step 1 of Example 22).

MS (ESI) m/z: 373 (M+H)$^+$.

$^1$H NMR (CDCl$_3$) δ 8.37 (1H, d, J=7.3 Hz), 7.48-7.38 (2H, m), 7.30-7.25 (1H, m), 7.10 (1H, d, J=7.3 Hz), 4.95-4.82 (1H, m), 4.58-4.45 (1H, m), 3.62-3.49 (1H, m), 3.38 (1H, dd, J=12.1, 7.0 Hz), 2.86 (1H, dd, J=12.1, 7.0 Hz), 2.75-2.41 (2H, m), 1.69-1.38 (6H, m), 1.61 (6H, d, J=6.6 Hz), 1.92-1.83 (6H, m).

Signals due to N$\underline{H}$ and O$\underline{H}$ were not observed.

Step 3. N-[(3S,5S)-5-(2-Ethyl-2-hydroxybutyl)pyrrolidin-3-yl]-1-isopropyl-1H-indazole-3-carboxamide ethanedioate The title compound was prepared according to the procedure described in step 9 of Example 8 from N-[(3S,5S)-5-(2-ethyl-2-hydroxybutyl)pyrrolidin-3-yl]-1-isopropyl-1H-indazole-3-carboxamide (step 2 of Example 22).

MS (ESI) m/z: 373 (M+H)$^+$.

IR (KBr) ν: 2974, 1649, 1540, 1492, 1463, 1405, 1280, 1204, 720 cm$^{-1}$ $^1$H NMR (DMSO-d$_6$) δ 8.53 (1H, d, J=8.1 Hz), 8.17 (1H, d, J=8.1 Hz), 7.82 (1H, d, J=8.8 Hz), 7.45 (1H, t, J=7.7 Hz), 7.28 (1H, t, J=7.7 Hz), 5.15-5.06 (1H, m), 4.72-4.58 (1H, m), 3.73-3.63 (1H, m), 3.48-3.51 (1H, m), 3.22 (1H, dd, J=11.0, 6.6 Hz), 2.60-2.48 (1H, m), 1.77-1.74 (3H, m), 1.55 (6H, d, J=6.6 Hz), 1.54-1.39 (4H, m), 0.85-0.77 (6H, m). Signals due to N$\underline{H}$ and O$\underline{H}$ were not observed.

Anal. Calcd. for C$_{21}$H$_{32}$N$_4$O$_2$.C$_2$H$_2$O$_4$.0.8 H$_2$O: C, 57.92; H, 7.52; N, 11.75. Found: C, 57.58; H, 7.42; N, 11.70.

[α]$_D^{22}$=+8.6° (C=0.25, Methanol).

Example 23

N-{(3S,5S)-5-[(1-Hydroxycyclohexyl)Methyl]Pyrrolidin-3-Yl}-1-Isopropyl-1H-Indazole-3-Carboxamide and its Ethanedioate

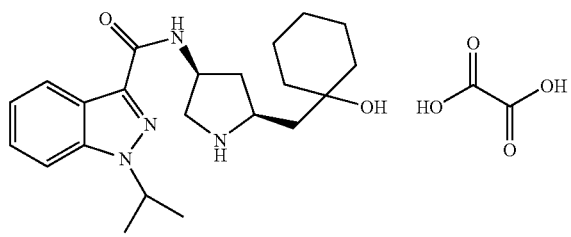

Step 1. tert-Butyl (2S,4S)-2-[(1-hydroxycyclohexyl)methyl]-4-{[(1-isopropyl-1H-indazol-3-yl)carbonyl]amino}pyrrolidine-1-carboxylate The title compound was prepared according to the procedure described in step 1 of Example 10 using pentamethylenebis(magnesium bromide) instead of methylmagnesium bromide.

MS (ESI) m/z: 385 (M+H)$^+$ (−BOC), 483 (M−H)$^-$.

$^1$H NMR (CDCl$_3$) δ 8.37 (1H, d, J=8.8 Hz), 7.48-7.26 (4H, m), 4.93-4.84 (1H, m), 4.65-4.55 (1H, m), 4.24 (1H, br s), 3.98 (1H, dd, J=11.7, 7.3 Hz), 3.82 (1H, br s), 3.33 (1H, dd, J=11.7, 5.1 Hz), 2.59-2.50 (1H, m), 2.17 (1H, dd, J=14.3, 5.5 Hz), 2.01-1.91 (1H, m), 1.80-1.38 (25H, m). Signal due to O$\underline{H}$ was not observed.

Step 2. N-{(3S,5S)-5-[(1-Hydroxycyclohexyl)methyl]pyrrolidin-3-yl}-1-isopropyl-1H-indazole-3-carboxamide The title compound was prepared according to the procedure described in step 3 of Example 7 from tert-butyl (2S,4S)-2-[(1-hydroxycyclohexyl)methyl]-4-{[(1-isopropyl-1H-indazol-3-yl)carbonyl]amino}pyrrolidine-1-carboxylate (step 1 of Example 23).

MS (ESI) m/z: 385 (M+H)$^+$, 383 (M−H)$^-$.

$^1$H NMR (CDCl$_3$) δ 8.37 (1H, d, J=8.1 Hz), 7.48-7.38 (2H, m), 7.30-7.25 (1H, m), 7.10 (1H, d, J=7.3 Hz), 4.93-4.84 (1H, m), 4.58-4.45 (1H, m), 3.67-3.54 (1H, m), 3.38 (1H, dd, J=12.1, 7.0 Hz), 2.86 (1H, dd, J=12.1, 7.0 Hz), 2.57 (1H, dt, J=13.2, 8.1 Hz), 1.77-1.26 (19H, m). Signals due to N$\underline{H}$ and O$\underline{H}$ were not observed.

Step 3. N-{(3S,5S)-5-[(1-Hydroxycyclohexyl)methyl]pyrrolidin-3-yl}-1-isopropyl-1H-indazole-3-carboxamide ethanedioate The title compound was prepared according to the procedure described in step 9 of Example 8 from N-{(3S,5S)-5-[(1-hydroxycyclohexyl)methyl]pyrrolidin-3-yl}-1-isopropyl-1H-indazole-3-carboxamide (step 2 of Example 23).

MS (ESI) m/z: 385 (M+H)$^+$, 383 (M−H)$^-$.

IR (KBr) ν: 2932, 1636, 1533, 1491, 1448, 1394, 1280, 1202, 1156, 753, 720 cm$^{-1}$ $^1$H NMR (DMSO-d$_6$) δ 8.53 (1H, d, J=8.1 Hz), 8.17 (1H, d, J=8.1 Hz), 7.82 (1H, d, J=8.1 Hz), 7.46 (1H, t, J=7.7 Hz), 7.28 (1H, t, J=7.3 Hz), 5.15-5.06 (1H, m), 4.70-4.58 (1H, m), 3.77-3.63 (1H, m), 3.45 (1H, dd, J=11.7, 8.1 Hz), 3.23 (1H, dd, J=11.7, 6.6 Hz), 2.61-2.47 (1H, m), 1.91-1.24 (19H, m). Signals due to N$\underline{H}$ and O$\underline{H}$ were not observed.

Anal. Calcd. for C$_{22}$H$_{32}$N$_4$O$_2$.C$_2$H$_2$O$_4$.0.3 H$_2$O: C, 60.06; H, 7.27; N, 11.67. Found: C, 59.75; H, 7.34; N, 11.64.

[α]$_D^{22}$=+6.4° (C=0.25, Methanol).

Example 24

N-[(3S,5R)-5-(3-Hydroxy-3-Methylbutyl)Pyrrolidin-3-Yl]-1-Isopropyl-1H-Indazole-3-Carboxamide and its Ethanedioate

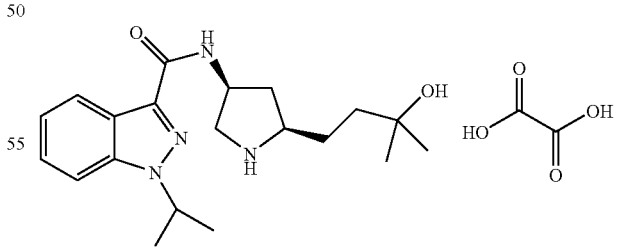

Step 1. tert-Butyl (2R,4S)-2-(3-hydroxy-3-methylbutyl)-4-{[(1-isopropyl-1H-indazol-3-yl)carbonyl]amino}pyrrolidine-1-carboxylate The title compound was prepared according to the procedure described in step 1 of Example 10 from tert-butyl (2R, 4S)-2-(3-ethoxy-3-oxopropyl)-4-{[(1-isopropyl-1H-indazol-3-yl)carbonyl]amino}pyrrolidine-1-carboxylate (step 6 of example 8).

MS (ESI) m/z: 359 (M+H)$^+$ (−BOC), 457 (M−H)$^-$.

$^1$H NMR (CDCl$_3$) δ 8.35 (1H, d, J=8.1 Hz), 7.46-7.37 (2H, m), 7.29-7.24 (1H, m), 7.11 (1H, d, J=7.3 Hz), 4.91-4.82 (1H, m), 4.62-4.55 (1H, m), 4.05 (1H, dd, J=11.0, 7.3 Hz), 3.89 (1H, br s), 3.21 (1H, dd, J=11.1, 7.3 Hz), 2.56-2.47 (1H, m), 2.14-1.70 (3H, m), 1.60-1.54 (8H, m), 1.46 (9H, m), 1.21 (6H, s).

A signal due to OH was not observed.

Step 2. N-[(3S,5R)-5-(3-Hydroxy-3-methylbutyl)pyrrolidin-3-yl]-1-isopropyl-1H-indazole-3-carboxamide The title compound was prepared according to the procedure described in step 3 of Example 7 from tert-butyl (2R,4S)-2-(3-hydroxy-3-methylbutyl)-4-{[(1-isopropyl-1H-indazol-3-yl)carbonyl]amino}pyrrolidine-1-carboxylate (step 1 of Example 24).

MS (ESI) m/z: 359 (M+H)$^+$.

$^1$H NMR (CDCl$_3$) δ 8.37 (1H, d, J=8.1 Hz), 7.47-7.37 (2H, m), 7.29-7.24 (2H, m), 4.92-4.83 (1H, m), 4.68-4.66 (1H, m), 3.31 (1H, dd, J=11.7, 7.3 Hz), 3.24-3.14 (1H, m), 2.99 (1H, dd, J=11.4, 4.8 Hz), 2.47 (1H, dt, J=13.2, 7.7 Hz), 1.83-1.65 (3H, m), 1.61 (6H, d, J=6.6 Hz), 1.54-1.45 (2H, m), 1.24 (3H, s), 1.23 (3H, s). Signals due to NH and OH were not observed.

Step 3. N-[(3S,5R)-5-(3-Hydroxy-3-methylbutyl)pyrrolidin-3-yl]-1-isopropyl-1H-indazole-3-carboxamide ethanedioate The title compound was prepared according to the procedure described in step 9 of Example 8 from N-[(3S,5R)-5-(3-hydroxy-3-methylbutyl)pyrrolidin-3-yl]-1-isopropyl-1H-indazole-3-carboxamide (step 2 of Example 24).

MS (ESI) m/z: 359 (M+H)$^+$.

IR (KBr) ν: 2936, 1644, 1539, 1491, 1280, 1203, 753, 721 cm$^{-1}$ $^1$H NMR (DMSO-d$_6$) δ 8.49 (1H, d, J=8.1 Hz), 8.17 (1H, d, J=8.1 Hz), 7.82 (1H, d, J=8.8 Hz), 7.45 (1H, t, J=7.3 Hz), 7.28 (1H, t, J=7.7 Hz), 5.15-5.06 (1H, m), 4.73-4.61 (1H, m), 3.46-3.39 (2H, m), 3.22 (1H, dd, J=11.4, 6.2 Hz), 2.52-2.44 (1H, m), 1.83-1.67 (3H, m), 1.55 (6H, d, J=6.6 Hz), 1.47-1.38 (2H, m), 1.10 (6H, s). Signals due to NH and OH were not observed.

Anal. Calcd. for C$_{20}$H$_{30}$N$_4$O$_2$·C$_2$H$_2$O$_4$·0.1 H$_2$O: C, 56.68; H, 7.21; N, 12.44. Found: C, 58.34; H, 7.43; N, 12.18.

[α]$_D^{22}$=−4.9° (C=0.25, Methanol).

Example 25

N-{(3S,5S)-5-[2-(Dim Ethylamino)-2-Oxoethyl]Pyrrolidin-3-Yl}-5-Fluoro-1-Isopropyl-1H-Indazole-3-Carboxamide and its Ethanedioate Step 1. tert-Butyl (2S,4S)-4-{[(5-fluoro-1H-indazol-3-yl)carbonyl]amino}-2-(2-methoxy-2-oxoethyl)pyrrolidine-1-carboxylate The title compound was prepared according to the procedure described in step 1 of Example 7 from 5-fluoro-1H-indazole-3-carboxylic acid (J. Heterocyclic Chem. 1964, 1, 239) and tert-butyl (2S,4S)-4-amino-2-(2-methoxy-2-oxoethyl)pyrrolidine-1-carboxylate (step 4 of Example 9).

MS (ESI) m/z: 321 (M+H)$^+$ (−BOC), 419 (M−H)$^-$.

$^1$H NMR (CDCl$_3$) δ 8.01 (1H, dd, J=8.9, 2.3 Hz), 7.48 (1H, dd, J=9.2, 4.0 Hz), 7.29-7.16 (2H, m), 4.72-4.54 (1H, m), 4.33-4.11 (1H, m), 4.11-3.90 (1H, m), 3.66 (3H, s), 3.45-2.85 (2H, m), 2.75-2.55 (2H, m), 2.10-1.84 (1H, m), 1.48 (9H, s). A signal due to NH was not observed.

Step 2. tert-Butyl (2S,4S)-4-{[(5-fluoro-1-isopropyl-1H-indazol-3-yl)carbonyl]amino}-2-(2-methoxy-2-oxoethyl)pyrrolidine-1-carboxylate The title compound was prepared according to the procedure described in step 1 of Example 4 from tert-butyl (2S,4S)-4-{[(5-fluoro-1H-indazol-3-yl)carbonyl]amino}-2-(2-methoxy-2-oxoethyl)pyrrolidine-1-carboxylate (step 1 of Example 25) and 2-iodopropane.

MS (ESI) m/z: 363 (M+H)$^+$ (−BOC).

$^1$H NMR (CDCl$_3$) δ 7.99 (1H, dd, J=8.9, 2.4 Hz), 7.41 (1H, dd, J=8.9, 4.3 Hz), 7.89 (1H, dt, J=8.9, 2.4 Hz), 7.09 (1H, d, J=7.3 Hz), 4.93-4.74 (1H, m), 4.68-4.54 (1H, m), 4.24-3.95 (2H, m), 3.68 (3H, s), 3.34-3.13 (2H, m), 2.74-2.54 (2H, m), 2.01-1.89 (1H, m), 1.61 (6H, d, J=7.3 Hz), 1.48 (9H, s).

Step 3. ((2S,4S)-1-(tert-Butoxycarbonyl)-4-{[(5-fluoro-1-isopropyl-1H-indazol-3-yl)carbonyl]amino}pyrrolidin-2-yl)acetic acid The title compound was prepared according to the procedure described in step 1 of Example 13 from tert-butyl (2S,4S)-4-{[(5-fluoro-1-isopropyl-1H-indazol-3-yl)carbonyl]amino}-2-(2-methoxy-2-oxoethyl)pyrrolidine-1-carboxylate (step 2 of Example 25).

MS (ESI) m/z: 349 (M+H)$^+$ (−BOC), 447 (M−H)$^-$.

$^1$H NMR (CDCl$_3$) δ 7.98 (1H, dd, J=8.6, 2.6 Hz), 7.41 (1H, dd, J=9.2, 4.0 Hz), 7.18 (1H, dt, J=9.2, 2.6 Hz), 7.07 (1H, d, J=7.3 Hz), 4.93-4.76 (1H, m), 4.69-4.50 (1H, m), 4.30-4.14 (1H, m), 4.03 (1H, dd, J=11.2, 6.6 Hz) 3.38-3.00 (2H, m), 2.77-2.54 (2H, m), 2.05-1.78 (1H, m), 1.60 (6H, d, J=6.6 Hz), 1.48 (9H, s). A signal due to CO$_2$H was not observed.

Step 4. tert-Butyl (2S,4S)-2-[2-(dimethylamino)-2-oxoethyl]-4-{[(5-fluoro-1-isopropyl-1H-indazol-3-yl)carbonyl]amino}pyrrolidine-1-carboxylate The title compound was prepared according to the procedure described in step 1 of Example 7 from ((2S,4S)-1-(tert-butoxycarbonyl)-4-{[(5-fluoro-1-isopropyl-1H-indazol-3-yl)carbonyl]amino}pyrrolidin-2-yl)acetic acid (step 3 of Example 25) and dimethylamine.

MS (ESI) m/z: 376 (M+H)$^+$ (−BOC).

¹H NMR (CDCl₃) δ 7.99 (1H, dd, J=8.9, 2.5 Hz), 7.47-7.34 (2H, m), 7.18 (1H, dt, J=8.9, 2.5 Hz), 4.94-4.74 (1H, m), 4.70-4.47 (1H, m), 4.30-3.99 (2H, m), 3.36-3.15 (2H, m), 3.08 (3H, s), 2.94 (3H, s), 2.71-2.51 (2H, m), 2.21-1.98 (1H, m), 1.60 (6H, d, J=6.6 Hz), 1.47 (9H, s).

Step 5. N-{(3S,5S)-5-[2-(Dimethylamino)-2-oxoethyl]pyrrolidin-3-yl}-5-fluoro-1-isopropyl-1H-indazole-3-carboxamide The title compound was prepared according to the procedure described in step 3 of Example 7 from tert-butyl (2S,4S)-2-[2-(dimethylamino)-2-oxoethyl]-4-{[(5-fluoro-1-isopropyl-1H-indazol-3-yl)carbonyl]amino}pyrrolidine-1-carboxylate (step 4 of Example 25).
MS (ESI) m/z: 376 (M+H)⁺, 374 (M−H)⁻.
¹H NMR (CDCl₃) δ 8.01 (1H, dd, J=8.9, 2.3 Hz), 7.47-7.35 (2H, m), 7.17 (1H, dt, J=8.9, 2.3 Hz), 4.92-4.75 (1H, m), 4.75-4.60 (1H, m), 3.60-3.45 (1H, m), 3.27 (1H, dd, J=10.6, 6.6 Hz) 3.05 (1H, dd, J=10.6, 3.3 Hz), 3.01 (3H, s), 2.96 (3H, s), 2.66 (1H, dd, J=16.5, 4.0 Hz), 2.61-2.45 (3H, m), 1.59 (6H, d, J=6.6 Hz), 1.61-1.44 (1H, m).

Step 6. N-{(3S,5S)-5-[2-(Dimethylamino)-2-oxoethyl]pyrrolidin-3-yl}-5-fluoro-1-isopropyl-1H-indazole-3-carboxamide ethanedioate The title compound was prepared according to the procedure described in step 9 of Example 8 from N-{(3S,5S)-5-[2-(dimethylamino)-2-oxoethyl]pyrrolidin-3-yl}-5-fluoro-1-isopropyl-1H-indazole-3-carboxamide (step 5 of Example 25).
MS (ESI) m/z: 376 (M+H)⁺, 374 (M−H)⁻.
¹H NMR (CDCl₃) δ 8.12 (1H, d, J=4.0 Hz), 7.92 (1H, dd, J=8.9, 2.5 Hz), 7.40 (1H, dd, J=8.9, 4.3 Hz), 7.16 (1H, dt, J=8.9, 2.5 Hz), 5.10-4.93 (1H, m), 4.91-4.75 (1H, m), 4.17-3.93 (1H, m), 3.83-3.50 (2H, m) 3.24-3.00 (1H, m), 3.00 (3H, s), 2.94 (3H, s), 2.85-2.55 (2H, m), 2.21-2.00 (1H, m), 1.60 (6H, d, J=6.6 Hz). A signal due to NH was not observed.
Anal. Calcd. for C₁₉H₂₆FN₅O₂·1.0 C₂H₂O₄·0.8 Dichloromethane-0.5 CH₃OH: C, 48.75; H, 5.80; N, 12.75. Found: C, 48.60; H, 6.08; N, 12.70.
[α]$_D^{22}$=−1.7° (C=0.26, Methanol).

Example 26

1-Isopropyl-N-((3S,5S)-5-{[Methyl(Methylsulfonyl)Amino]Methyl}Pyrrolidin-3-YL)-1H-Indazole-3-Carboxamide and its Ethanedioate

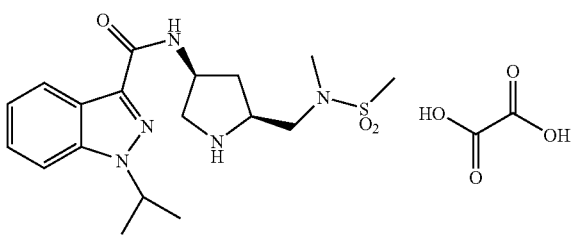

Step 1. tert-Butyl (2S,4S)-4-{[(1-isopropyl-1H-indazol-3-yl)carbonyl]amino}-2-[(methylamino)methyl]pyrrolidine-1-carboxylate The mixture of tert-butyl (2S,4S)-4-{[(1-isopropyl-1H-indazol-3-yl)carbonyl]amino}-2-{[(methylsulfonyl)oxy]methyl}pyrrolidine-1-carboxylate (197 mg, 0.41 mmol, step 1 of Example 17) and 40% monomethylamine aqueous solution (3 mL) in tetrahydrofuran (2 mL) was stirred at 80° C. for 32 h. After cooling to room temperature, the mixture was added to saturated sodium hydrogencarbonate aqueous solution. The organic phase was extracted with ethyl acetate (10 mL×3). The organic layer was washed with brine, dried over sodium sulfate and concentrated. The residue was chromatographed on a column of NH gel eluting with n-hexane/ethyl acetate (4:1 to 2:1) to give 66 mg (39%) of the title compound as a white solid.
MS (ESI) m/z: 316 (M+H)⁺ (−BOC), 414 (M−H)⁻.
¹H NMR (CDCl₃) δ 10.04-9.65 (1H, br), 8.41 (1H, d, J=7.9 Hz), 7.50-7.34 (2H, m), 7.32-7.22 (1H, m), 4.96-4.68 (2H, m), 4.18-3.94 (1H, m), 3.89-3.62 (1H, m), 3.53-3.15 (2H, m), 2.59 (3H, s), 2.62-2.47 (2H, m), 1.92 (1H, d, J=13.2 Hz), 1.61 (6H, d, J=6.6 Hz), 1.45 (9H, s). A signal due to CONH was not observed.

Step 2. tert-Butyl (2S,4S)-4-{[(1-isopropyl-1H-indazol-3-yl)carbonyl]amino}-2-{[methyl(methylsulfonyl)amino]methyl}pyrrolidine-1-carboxylate The title compound was prepared according to the procedure described in step 3 of Example 17 from tert-butyl (2S,4S)-4-{[(1-isopropyl-1H-indazol-3-yl)carbonyl]amino}-2-[(methylamino)methyl]pyrrolidine-1-carboxylate (step 1 of Example 26) and methanesulfonyl chloride.
MS (ESI) m/z: 394 (M+H)⁺ (−BOC), 492 (M−H)⁻.
¹H NMR (CDCl₃) δ 8.35 (1H, d, J=8.6 Hz), 7.56-7.34 (3H, m), 7.33-7.20 (1H, m), 4.98-4.78 (1H, m), 4.67-4.50 (1H, m), 4.20-3.93 (2H, m), 3.58-3.33 (3H, m), 2.97 (3H, s), 2.83 (3H, s), 2.54-2.36 (1H, m), 2.35-2.22 (1H, m), 1.63 (6H, d, J=6.6 Hz), 1.46 (9H, s).

Step 3. 1-isopropyl-N-((3S,5S)-5-{[methyl(methylsulfonyl)amino]methyl}pyrrolidin-3-yl)-1H-indazole-3-carboxamide The title compound was prepared according to the procedure described in step 3 of Example 7 from tert-butyl (2S,4S)-4-{[(1-isopropyl-1H-indazol-3-yl)carbonyl]amino}-2-{[methyl(methylsulfonyl)amino]methyl}pyrrolidine-1-carboxylate (step 2 of Example 26).
MS (ESI) m/z: 394 (M+H)⁺ 392 (M−H)⁻.
¹H NMR (CDCl₃) δ 8.37 (1H, d, J=7.9 Hz), 7.50-7.32 (2H, m), 7.32-7.20 (2H, m), 4.95-4.79 (1H, m), 4.72-4.55 (1H, m), 3.57-3.42 (1H, m), 3.41-3.08 (3H, m), 3.05-2.94 (1H, m), 2.98 (3H, s), 2.85 (3H, s), 2.55-2.38 (1H, m), 1.61 (6H, d, J=6.6 Hz), 1.63-1.48 (1H, m). A signal due to NH was not observed.

Step 4. 1-Isopropyl-N-((3S,5S)-5-{[methyl(methylsulfonyl)amino]methyl}pyrrolidin-3-yl)-1H-indazole-3-carboxamide ethanedioate The title compound was prepared according to the procedure described in step 9 of Example 8 1-isopropyl-N-((3S,5S)-5-{[methyl(methylsulfonyl)amino]methyl}pyrrolidin-3-yl)-1H-indazole-3-carboxamide (step 3 of Example 26).
MS (ESI) m/z: 394 (M+H)⁺ 392 (M−H)⁻.
¹H NMR (DMSO-d₆) δ 8.54 (1H, d, J=7.3 Hz), 8.18 (1H, d, J=7.3 Hz), 7.83 (1H, d, J=8.6 Hz), 7.46 (1H, t, J=7.3 Hz), 7.27 (1H, t, J=7.3 Hz), 5.19-5.03 (1H, m), 4.85-4.65 (1H, m), 3.91-3.74 (1H, m), 3.59-3.24 (4H, m), 2.99 (3H, s), 2.86 (3H, s), 2.64-2.44 (1H, m), 1.91-1.71 (1H, m), 1.55 (6H, d, J=6.6 Hz).
Anal. Calcd. for C₁₈H₂₇N₅O₃S·1.5 C₂H₂O₄·1.0 H₂O: C, 46.15; H, 5.90; N, 12.81. Found: C, 46.14; H, 6.07; N, 12.77.
[α]$_D^{22}$=−7.5° (C=0.26, Methanol).

Example 27

(+)-1-Ethyl-N-{Cis-6-[(4-Hydroxytetrahydro-2H-Pyran-4-Yl)Methyl]Piperidin-3-Yl}-1H-Indazole-3-Carboxamide

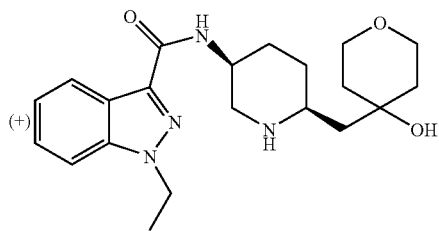

Step 1. (+)-tert-butyl cis-5-amino-2-[(4-hydroxytetrahydro-2H-pyran-4-yl)methyl]piperidine-1-carboxylate The fraction-1 (650 mg) and fraction-2 (650 mg) were prepared from racemic tert-butyl cis-5-amino-2-[(4-hydroxytetrahydro-2H-pyran-4-yl)methyl]piperidine-1-carboxylate (2.0 g, step 5 of Example 2) by HPLC as follows.
Isolation Condition
Column: CHIRALPAK® AD-H (20 mm I.D.×250 mm, DAICEL)
Mobile phase: n-hexane/2-propanol/diethylamine (93/7/0.1)
flow rate: 18.9 mL/min
(+)-tert-butyl cis-5-amino-2-[(4-hydroxytetrahydro-2H-pyran-4-yl)methyl]piperidine-1-carboxylate (Fraction-1)
NMR: spectrum data were identical with those of the racemate
optical rotation: $[\alpha]_D^{23}=+10.7°$ (C=0.25, Methanol)
retention time: 16 min
(−)-tert-butyl cis-5-amino-2-[(4-hydroxytetrahydro-2H-pyran-4-yl)methyl]piperidine-1-carboxylate (Fraction-2)
NMR: spectrum data were identical with those of the racemate
optical rotation: $[\alpha]_D^{23}=-9.0°$ (C=0.25, Methanol)
retention time: 30 min

Step 2. (+)-tert-Butyl cis-5-{[(1-ethyl-1H-indazol-3-yl)carbonyl]-amino}-2-[(4-hydroxytetrahydro-2H-pyran-4-yl)methyl]piperidine-1-carboxylate The title compound was prepared according to the procedure described in step 6 of Example 2 from 1-ethyl-1H-indazole-3-carboxylic acid (Chemical & Pharmaceutical Bulletin, 1995, 43, 1912-1930) and (+)-tert-butyl cis-5-amino-2-[(4-hydroxytetrahydro-2H-pyran-4-yl)methyl]piperidine-1-carboxylate (step 1 of Example 27).

MS (ESI) m/z: 487 (M+H)+, 485 (M−H)−.
$^1$H NMR (CDCl$_3$) δ 8.38 (1H, d, J=8.1 Hz), 7.51-7.37 (2H, m), 7.35-7.24 (1H, m), 6.88 (1H, d, J=8.8 Hz), 4.67-4.53 (1H, m), 4.45 (2H, dd, J=14.7, 7.3 Hz), 4.37-4.24 (1H, m), 4.20-4.01 (1H, m), 3.93-3.61 (5H, m), 2.77 (1H, t, J=12.1 Hz), 2.13-1.98 (2H, m), 1.98-1.82 (1H, m), 1.76-1.35 (18H, m) (including 1.55 (3H, t, J=7.3 Hz), 1.47 (9H, s)).
A signal due to OH was not observed.

Step 3. (+)-1-Ethyl-N-{cis-6-[(4-hydroxytetrahydro-2H-pyran-4-yl)methyl]piperidin-3-yl}-1H-indazole-3-carboxamide The title compound was prepared according to the procedure described in step 7 of Example 2 from tert-butyl cis-5-{[(1-ethyl-1H-indazol-3-yl)carbonyl]amino}-2-[(4-hydroxytetrahydro-2H-pyran-4-yl)methyl]piperidine-1-carboxylate (chiral, step 2 of Example 27).

IR (KBr) v: 3406, 2939, 1653, 1533, 1491, 1204, 1099, 752 cm$^{-1}$.
MS (ESI) m/z: 387 (M+H)+, 385 (M−H)−.
$^1$H NMR (CDCl$_3$) δ 8.36 (1H, d, J=8.1 Hz), 7.50-7.36 (2H, m), 7.34-7.24 (1H, m), 7.20 (1H, d, J=7.3 Hz), 5.82 (1H, br s), 4.47 (2H, dd, J=14.7, 7.3 Hz), 4.20-4.05 (1H, m), 3.91-3.64 (4H, m), 3.25-3.02 (2H, m), 2.93 (1H, dd, J=13.9, 2.9 Hz), 2.05-1.88 (2H, m), 1.81-1.35 (12H, m).
Anal. Calcd. for $C_{21}H_{30}N_4O_3 \cdot 0.4\,H_2O$: C, 64.07; H, 7.89; N, 14.23. Found: C, 63.88; H, 7.93; N, 14.04. $[\alpha]_D^{23}=+13.5°$ (C=0.25, Methanol).

All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The invention claimed is:
1. A compound of the formula (I):

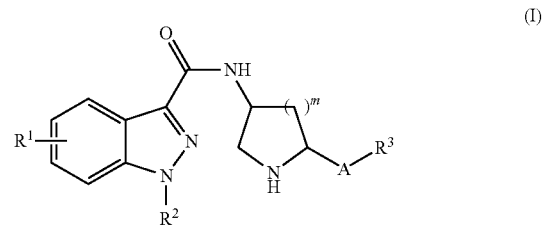

wherein:
$R^1$ is hydrogen, halogen, or $C_1$-$C_6$ alkyl;
$R^2$ is $C_1$-$C_6$ alkyl or $C_3$-$C_6$ cycloalkyl;
$R^3$ is hydroxy, mercapto, —C(=O)—NR$^4$R$^5$, —NR$^6$—R$^7$, $C_1$-$C_6$ alkoxy, $C_3$-$C_6$ cycloalkyl, or heterocyclyl; the said $C_1$-$C_6$ alkoxy, $C_3$-$C_6$ cycloalkyl, and heterocyclyl being unsubstituted or substituted with 1 to 2 substituents independently selected from hydroxy, mercapto, —C(=O)—NR$^4$R$^5$, or —NR$^6$—R$^7$;
$R^4$ and $R^5$ are independently hydrogen, $C_1$-$C_6$ alkyl, or hydroxy $C_1$-$C_6$ alkyl; or $R^4$ and $R^5$ being taken together with the nitrogen to which they are attached form a 3 to 6 membered heterocyclic ring;
$R^6$ is hydrogen, $C_1$-$C_6$ alkyl, or hydroxy $C_1$-$C_6$ alkyl;
$R^7$ is $C_1$-$C_6$ alkyl, hydroxy $C_1$-$C_6$ alkyl, ($C_1$-$C_6$ alkyl)carbonyl, or ($C_1$-$C_6$ alkyl)sulfonyl;
A is $C_1$-$C_6$ alkylene; and
m is 1 or 2;
or a pharmaceutically acceptable salt thereof.

2. The compound of claim 1, wherein:
R¹ is hydrogen or halogen;
R² is $C_2$-$C_4$ alkyl;
R³ is hydroxy, $C_3$-$C_6$ cycloalkyl, or heterocyclyl; the said $C_3$-$C_6$ cycloalkyl and heterocyclyl being unsubstituted or substituted with 1 to 2 substituents independently selected from hydroxy or mercapto;
or a pharmaceutically acceptable salt thereof.

3. The compound of claim 2, wherein:
R¹ is hydrogen or fluorine;
R² is ethyl or isopropyl;
R³ is hydroxy, $C_3$-$C_6$ cycloalkyl, or heterocyclyl; the said $C_3$-$C_6$ cycloalkyl and heterocyclyl being substituted with a hydroxy;
or a pharmaceutically acceptable salt thereof.

4. A pharmaceutical composition comprising the compound of claim 1 or a pharmaceutically acceptable salt thereof, and a pharmaceutically acceptable carrier.

5. A pharmaceutical composition comprising the compound of claim 1 or a pharmaceutically acceptable salt thereof, a pharmaceutically acceptable carrier, and a pharmacologically active agent.

6. A method for alleviating or inhibiting the progress of a condition mediated by 5-$HT_4$ receptor activity in a mammalian subject, including a human, which comprises administering to a mammal in need of such alleviating or inhibiting a therapeutically effective amount of the compound of claim 1 or a pharmaceutically acceptable salt thereof, wherein said condition is gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageal disease, or nausea.

7. A compound which is
N-[cis-6-(2-hydroxyethyl)piperidin-3-yl]-1-isopropyl-1H-indazole-3-carboxamide;
N-{cis-6-[(4-hydroxytetrahydro-2H-pyran-4-yl)methyl]piperidin-3-yl}-1-isopropyl-1H-indazole-3-carboxamide;
N-[cis-6-(2-hydroxy-2-methylpropyl)piperidin-3-yl]-1-isopropyl-1H-indazole-3-carboxamide;
1-cyclobutyl-N-{cis-6-[(4-hydroxytetrahydro-2H-pyran-4-yl)methyl]piperidin-3-yl}-1H-indazole-3-carboxamide;
N-[cis-6-(3-hydroxypropyl)piperidin-3-yl]-1-isopropyl-1H-indazole-3-carboxamide;
N-[cis-6-(3-hydroxy-3-methylbutyl)piperidin-3-yl]-1-isopropyl-1H-indazole-3-carboxamide;
N-[(3S,5S)-5-(hydroxymethyl)pyrrolidin-3-yl]-1-isopropyl-1H-indazole-3-carboxamide;
N-[(3S,5R)-5-(3-hydroxypropyl)pyrrolidin-3-yl]-1-isopropyl-1H-indazole-3-carboxamide;
N-[(3S,5S)-5-(2-hydroxyethyl)pyrrolidin-3-yl]-1-isopropyl-1H-indazole-3-carboxamide;
N-[(3S,5S)-5-(2-hydroxy-2-methylpropyl)pyrrolidin-3-yl]-1-isopropyl-1H-indazole-3-carboxamide;
5-fluoro-N-[(3S,5S)-5-(2-hydroxy-2-methylpropyl)pyrrolidin-3-yl]-1-isopropyl-1H-indazole-3-carboxamide;
N-{(3S,5S)-5-[(2-hydroxy-2-methylpropoxy)methyl]pyrrolidin-3-yl}-1-isopropyl-1H-indazole-3-carboxamide;
1-isopropyl-N-{(3S,5S)-5-[2-(methylamino)-2-oxoethyl]pyrrolidin-3-yl}-1H-indazole-3-carboxamide;
1-isopropyl-N-[(3S,5S)-5-(2-morpholin-4-yl-2-oxoethyl)pyrrolidin-3-yl]-1H-indazole-3-carboxamide;
1-isopropyl-N-[(3S,5S)-5-(2-oxo-2-piperidin-1-ylethyl)pyrrolidin-3-yl]-1H-indazole-3-carboxamide;
N-{(3S,5S)-5-[2-(dimethylamino)-2-oxoethyl]pyrrolidin-3-yl}-1-isopropyl-1H-indazole-3-carboxamide;
N-{(3S,5S)-5-[(acetylamino)methyl]pyrrolidin-3-yl}-1-isopropyl-1H-indazole-3-carboxamide;
1-isopropyl-N-((3S,5S)-5-{[(methylsulfonyl)amino]methyl}pyrrolidin-3-yl)-1H-indazole-3-carboxamide;
N-{(3S,5R)-5-[2-(acetylamino)ethyl]pyrrolidin-3-yl}-1-isopropyl-1H-indazole-3-carboxamide;
N-{(3S,5R)-5-[2-(isobutyrylamino)ethyl]pyrrolidin-3-yl}-1-isopropyl-1H-indazole-3-carboxamide;
N-((3S,5S)-5-{[2-(dimethylamino)-2-oxoethoxy]methyl}pyrrolidin-3-yl)-1-isopropyl-1H-indazole-3-carboxamide;
N-[(3S,5S)-5-(2-ethyl-2-hydroxybutyl)pyrrolidin-3-yl]-1-isopropyl-1H-indazole-3-carboxamide;
N-{(3S,5S)-5-[(1-hydroxycyclohexyl)methyl]pyrrolidin-3-yl}-1-isopropyl-1H-indazole-3-carboxamide;
N-[(3S,5R)-5-(3-hydroxy-3-methylbutyl)pyrrolidin-3-yl]-1-isopropyl-1H-indazole-3-carboxamide;
N-{(3S,5S)-5-[2-(dimethylamino)-2-oxoethyl]pyrrolidin-3-yl}-5-fluoro-1-isopropyl-1H-indazole-3-carboxamide;
1-isopropyl-N-((3S,5S)-5-{[methyl(methylsulfonyl)amino]methyl}-pyrrolidin-3-yl)-1H-indazole-3-carboxamide; or
(+)-1-ethyl-n-{cis-6-[(4-hydroxytetrahydro-2H-pyran-4-yl)methyl]piperidin-3-yl}-1H-indazole-3-carboxamide;
or a pharmaceutically acceptable salt thereof.

\* \* \* \* \*